United States Patent
Natesan et al.

(10) Patent No.: US 7,030,148 B2
(45) Date of Patent: Apr. 18, 2006

(54) HETEROCYCLIC COMPOUNDS HAVING ANTIBACTERIAL ACTIVITY: PROCESS FOR THEIR PREPARATION AND PHARMACEUTICAL COMPOSITIONS CONTAINING THEM

(75) Inventors: Selvakumar Natesan, Andhra Pradesh (IN); Jagattaran Das, Andhra Pradesh (IN); Javed Iqbal, Adhra Pradesh (IN); Sitaram Kumar Magadi, Adhra Pradesh (IN); Srinivasa Rao Naga Venkata Mamidi, Adhra Pradesh (IN); Rajagopalan Ramanujam, Andhra Pradesh (IN); Baskaran Sundarababu, Andhra Pradesh (IN); Braj Bhushan Lohray, Andhra Pradesh (IN)

(73) Assignee: Dr. Reddy's Research Foundation, Andhra Pradesh (IN)

( * ) Notice: Subject to any disclaimer, the term of this patent is extended or adjusted under 35 U.S.C. 154(b) by 97 days.

(21) Appl. No.: 10/032,392

(22) Filed: Dec. 21, 2001

(65) Prior Publication Data

US 2003/0065175 A1    Apr. 3, 2003

(30) Foreign Application Priority Data

Dec. 26, 2000   (IN)   ........................ 1124/MAS/2000
Jan. 4, 2001   (IN)   .............................. 15/MAS/01

(51) Int. Cl.
*A61K 31/421*    (2006.01)
*C07D 263/04*    (2006.01)

(52) U.S. Cl. ...................... 514/376; 548/229; 544/106; 544/358; 546/184

(58) Field of Classification Search ................ 514/365, 514/376, 375; 548/187, 189, 221, 232, 229; 546/184; 544/106, 358
See application file for complete search history.

(56) References Cited

U.S. PATENT DOCUMENTS 2,987,505 A * 6/1961 Werner et al. ............. 560/77.5
3,651,079 A    3/1972 Skorez et al.
4,174,958 A   11/1979 Pilgram 6,124,334 A    9/2000 Hutchinson

FOREIGN PATENT DOCUMENTS

DE   2357591   11/1973
DE   3536066   10/1985
WO   95/07271   3/1995
WO   96/13502   5/1996
WO   97/27188   7/1997
WO   01/09107   2/2001

OTHER PUBLICATIONS

Braun, et al 1979, Liebigs, Annalen der Chemie, 2, 200-9.*
Sorokin, et al, 1987, Khimicheskaya Tekhnologiya, 24(5), 561-5.*
Braun et al (1979): STN International, CAPLUS database, Columbus, Ohio, Accession No.: 1979: 168494.*
Abstract of Japanese Patent dated Feb. 29, 2000, vol. 2000 No. 2, Feb. 29, 2000, JP 11 322729.
Melissaris A P et al., "Thermally Stable Ploymers Based on Bismaleimides Containing Amide, Imide, and Ester Linkages", Journal of Polymer Science, (1989), vol. 27, No. 1, pp. 245-262.
Marino Artico, et al., "Compounds with Antiblastic Activity. XXXIV. Derivatives of 3-(p-aminophenyl)-2-oxazolidinone: synthesis and antineoplastic activities", FARMACO ED SCI.(1969), vol. 24, No. 2, pp. 179-190.

* cited by examiner

*Primary Examiner*—Golam M. M. Shameem

(57) ABSTRACT

The present invention relates to novel oxazolidinone compounds of the general formula (I)

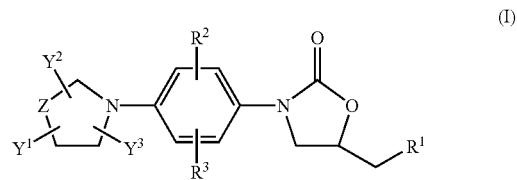

where $R^1$, $R^2$, $R^3$, $Y^1$, $Y^2$, $Y^3$, and Z are as defined in the description; their derivatives, their analogs, their tautomeric forms, their stereoisomers, their polymorphs, their pharmaceutical acceptable salts, their pharmaceutically acceptable solvates and pharmaceutical compositions containing them.

23 Claims, No Drawings

HETEROCYCLIC COMPOUNDS HAVING ANTIBACTERIAL ACTIVITY: PROCESS FOR THEIR PREPARATION AND PHARMACEUTICAL COMPOSITIONS CONTAINING THEM

FIELD OF THE INVENTION

The present invention relates to novel oxazolidinone compounds, their derivatives, their analogs, their tautomeric forms, their stereoisomers, their polymorphs, their pharmaceutically acceptable salts, their pharmaceutically acceptable solvates and pharmaceutical compositions containing them. More particularly, the present invention relates to novel oxazolidinones of the general formula (I).

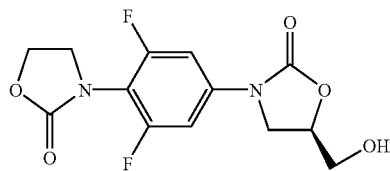

their derivatives, their analogs, their tautomeric forms, their stereoisomers, their polymorphs, their pharmaceutically acceptable salts, their pharmaceutically acceptable solvates and pharmaceutical compositions containing them.

The present invention also relates to a process for the preparation of the above said novel compounds, their derivatives, their analogs, their tautomeric forms, their stereoisomers, their polymorphs, their pharmaceutically acceptable salts, their pharmaceutically acceptable solvates and pharmaceutical compositions containing them.

The present invention also relates to novel intermediates, methods for their preparation and their use in the preparation of compounds of formula (I).

Oxazolidinones are useful as antibacterials (J. Med. Chem., 1996, 39, 673), antihistamines and anti allergic agents (EP 291,244), anticonvulsants (DE 3,915,184), for treating cognition disorders, as anti psychotics, anti platelet aggregators, antidepressants, sedatives, hypnotics, monoamine oxidase inhibitors (WO 97/13768) and as chiral auxiliaries (Aldrichimica Acta, 1982, 15 23) in asymmetric synthesis.

BACKGROUND OF THE INVENTION

Since the discovery of penicillin, pharmaceutical companies have produced more than one hundred antibacterial agents to combat a wide variety of bacterial infections. In the past several years, due to the misuse of these antibiotics there has been rapid emergence of bacterial resistance to several of these antibiotics. The multidrug resistance among these bacterial pathogens may also be due to mutation leading to more virulent clinical isolation, the most disturbing milestone has been the acquisition of resistance to vancomycin, an antibiotic generally regarded as the agent of last resort for serious Gram-positive infections. This growing multidrug resistance has recently rekindled interest in the search for a new structural class of antibiotics that inhibit or kill these bacteria possibly by novel mechanisms.

A problem of larger dimension is the increasing incidence of the more virulent, methicillin-resistant *Staphylococcus aureas* (MRSA) among clinical isolates found worldwide. As with vancomycin resistant organisms, many MRSA strains are resistant to most of the known antibiotics, but MRSA strains have remained sensitive to vancomycin. However, in view of the increasing reports of vancomycin resistant clinical isolates and growing problem of bacterial resistance, there is an urgent need for new molecular entities effective against the emerging and currently problematic Gram-positive organisms.

Recently, several oxazolidinones have been discovered, which inhibit protein synthesis by binding to the 50S-ribosomal subunit which is close to the site to which chloramphenicol and lincomycin bind but their mode of action is mechanistically distinct from these two antibiotics.

The new class of oxazolidinones of the present invention is useful for the treatment of a number of resistant and sensitive gram-positive strains both in vitro and in vivo. Some of the hitherto known compounds described in the prior art are outlined below:

(i) International Patent Application WO 93/23384 discloses compounds of formula (IIa)

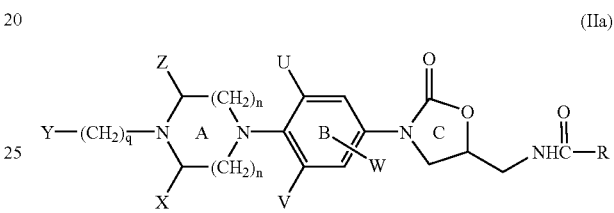

where

Y represents a hydrogen atom, $(C_1-C_6)$alkyl or aryl, OH, $O(C_1-C_6)$alkyl, O-vinyl, O-phenyl, $O-C(=O)(C_1-C_6)$alkyl, $-O-C(=O)$-phenyl (phenyl can be substituted with one to three F, Cl, $OCH_3$, OH, $NH_2$, or $(C_1-C_4)$alkyl) or $O-C(=O)-O-CH_3$, $S-(C_1-C_6)$alkyl, $SO_2-(C_1-C_6)$alkyl, $-SO_2-N(R^3)_2$, (where $R^3$ is independently hydrogen, $(C_1-C_4)$alkyl or phenyl which can be substituted with one to three F, Cl, $OCH_3$, OH, $NH_2$, or $(C_1-C_4)$alkyl); $-C(=O)-(C_1-C_6)$alkyl, $-C(=O)-O-(C_1-C_6)$alkyl, $-C(=O)-N(R^3)_2$, $-C(=O)-CH(R^4)N(R^3)_2$, $-C(=O)-CH(R^4)-NH-C(NH)-NH_2$ (where $R^4$ is an amino acid side chain); $-N(R^3)_2$, $-N(CH_2)_m$ (where m is 2–6 and forms a cyclic structure with the nitrogen atom and where one or more carbon atoms can be replaced with S, O or $NR^3$), $-C(CH_3)=N-OR$ or Y represents any of the groups given below:

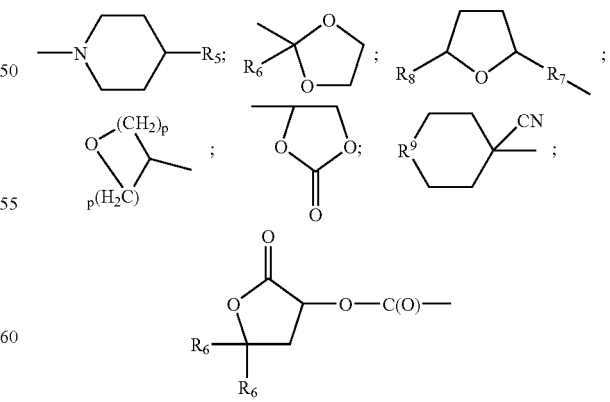

where $R^5$ is OH, $OCH_3$, $CH_2OH$, $CH_2OCH_3$, $CO_2CH_3$, $CO_2C_2H_5$, $R^6$ represents $CH_3$ or hydrogen, $R^7$ represents CH$_2$ or C(=O), R$^8$ represents hydrogen or =O, p is 1 or 2, R$^9$ represents O, S, S(O), SO$_2$, CH$_2$, NH, NCH$_3$, NC$_2$H$_5$, NCHO, NCOCH$_3$ or NCO$_2$CH$_3$, wherein each occurrence of said (C$_1$–C$_6$)alkyl may be substituted with one or more F, Cl, Br, I, OR$^1$, COOR$^1$, CN, SR$^1$ or R$^1$ (where R$^1$ is a hydrogen or (C$_1$–C$_4$)alkyl); X and Z are independently (C$_1$–C$_6$) alkyl, (C$_3$–C$_{12}$)cycloalkyl or hydrogen or X and Z form a (C$_0$–C$_3$) bridging group, preferably X and Z are hydrogen;

U, V and W are independently (C$_1$–C$_6$)alkyl, F, Cl, Br, hydrogen or a (C$_1$–C$_6$)alkyl substituted with one or more of F, Cl, Br or I, preferably U and V are F and W is hydrogen;

R is hydrogen, (C$_1$–C$_{12}$)alkyl, (C$_3$–C$_{12}$)cycloalkyl, (C$_1$–C$_6$)alkoxy, (C$_1$–C$_6$)alkyl substituted with one or more F, Cl, Br, I or OH, n is 1 or 2; and q is 0–4 inclusive.

An example of this class of compounds is shown in formula (IIb)

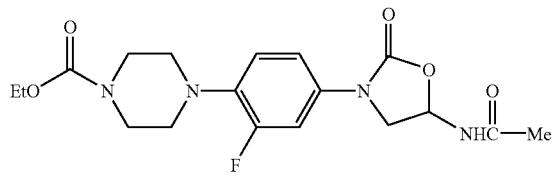

(IIb)

(ii) International Patent Application WO 98/01447 discloses compounds of formula (IIc)

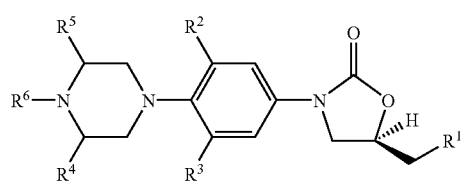

(IIc)

wherein

R$^1$ represents —NHC(=O)R$^a$ wherein R$^a$ represents (C$_1$–C$_4$)alkyl;

R$^2$ and R$^3$ represent hydrogen or fluoro;

R$^4$ and R$^5$ are independently hydrogen or methyl;

R$^6$ represent pyridyl, optionally substituted by substituents selected from (C$_1$–C$_4$)alkyl (optionally substituted), halo, trifluoromethyl, (C$_1$–C$_4$)alkyl-S(O)$_n$— (wherein n is 0, 1 or 2), (C$_1$–C$_4$)alkyl SO$_2$amino, (C$_1$–C$_4$)alkanoylamino, carboxy, hydroxy, amino, (C$_1$–C$_4$)alkylamino, di-(C$_1$–C$_4$) alkylamino, (C$_1$–C$_4$) alkoxycarbonyl, carbamoyl, N—(C$_1$–C$_4$)alkylcarbamoyl, di-(N—(C$_1$–C$_4$)alkyl)carbamoyl (wherein the (C$_1$–C$_4$)alkyl group on groups in the last two mentioned carbamoyl groups is optionally substituted by hydroxy, (C$_1$–C$_4$)alkoxy or (C$_1$–C$_4$)alkoxycarbonyl), (C$_2$–C$_4$)alkenyl (optionally substituted by carboxy or (C$_1$–C$_4$)alkoxycarbonyl), (C$_1$–C$_4$)alkoxy, cyano, or nitro groups.

An example of this class of compounds is shown in formula (IId)

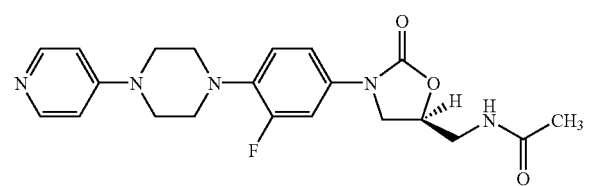

(IId)

(iii) International Patent Application No. WO 95/07271 discloses compounds of formula (IIe)

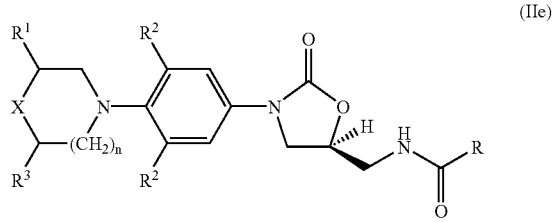

(IIe)

wherein

X represents O, S, SO, SO$_2$, SNR$^{10}$ or SONR$^{10}$;

R represents hydrogen, (C$_1$–C$_8$)alkyl optionally substituted with one or more of the following: F, Cl, hydroxy, (C$_1$–C$_8$)alkoxy, (C$_1$–C$_8$)acyloxy or —OCH$_2$Ph or R represents (C$_3$–C$_6$)cycloalkyl, amino, (C$_1$–C$_8$)alkylamino, (C$_1$–C$_8$)dialkylamino or (C$_1$–C$_8$)alkoxy;

R$^1$ represents hydrogen except when X is O, then R$^1$ can be hydrogen, CH$_3$, cyano, —CO$_2$H, CO$_2$R or (CH$_2$)$_m$R$^{11}$ (m is 1 or 2);

R$^2$ represents independently hydrogen, F or Cl; R$^3$ represents hydrogen or CH$_3$;

R$^{10}$ independently represents hydrogen, (C$_1$–C$_4$)alkyl (optionally substituted with chloro, fluoro, hydroxy, (C$_1$–C$_8$) alkoxy, amino, (C$_1$–C$_8$)alkylamino, or (C$_1$–C$_8$)dialkylamino) or p-toluenesulfonyl;

R$^{11}$ represents hydrogen, hydroxy, OR, OCOR, NH$_2$, NHCOR or N(R$^{10}$)$_2$; and n is 0, 1 or 2.

An example of this class of compounds is shown in formula (IIf)

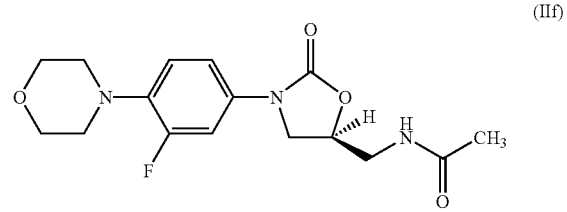

(IIf)

(iv) International Patent Application WO 95/25106 discloses compounds of formula (IIg)

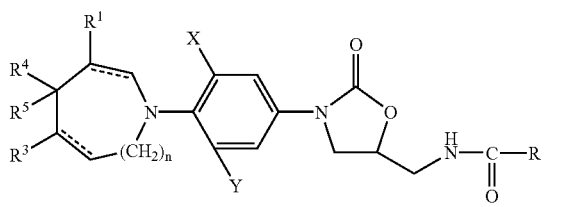

(IIg)

where

R is hydrogen atom, (C$_1$–C$_8$)alkyl, (C$_3$–C$_6$)cycloalkyl, amino, (C$_1$–C$_8$)alkylamino, (C$_1$–C$_8$)dialkylamino, (C$_1$–C$_8$) alkoxy or (C$_1$–C$_8$)halogen alkyl;

R$^1$ and R$^3$ are each and independently represents hydrogen atom, halogen atom, (C$_1$C$_8$)alkyl, (C$_3$–C$_6$)cycloalkyl, —(CH$^2$)$_m$—OR$^{11}$ or —C(=O)—R$^{41}$;

X and Y are each and independently represents hydrogen atom, halogen atom;

R$^4$ and R$^5$ are each and independently represents hydrogen atom, (C$_1$–C$_8$)alkyl, (C$_1$–C$_8$)alkoxy, (C$_1$–C$_8$)alkylthio, —(CH$_2$)$_m$—OR$^{51}$, —O—(CH$_2$)$_m$—OR$^{51}$, —NR$^{42}$R$^{52}$, —N=CH—NR$^{42}$R$^{55}$, —C(=O)—NR$^{42}$R$^{52}$ or —(CH$_2$)$_m$—C(=A)—R$^{41}$ or they may combine together to form =O, =NR$^{43}$, =S, =CR$^{44}$R$^{54}$ or an optionally substituted, unsaturated or saturated 5 or 6 membered hetero ring having 1–3 hetero atoms selected from the group consisting of a nitrogen atom, an oxygen atom and a sulfur atom;

R$^{11}$ and R$^{12}$ are each and independently represents hydrogen atom, (C$_1$–C$_8$)alkyl or methoxymethyl; R$^{41}$ is hydrogen atom, —(CH$_2$)$_m$—OH, (C$_1$–C$_8$)alkyl, (C$_1$–C$_8$)alkoxy, —O—CH$^2$—O—C(=O)—R$^{11}$ or —(CH$_2$)$_m$—C(=O)—OR$^{11}$;

R$^{42}$ and R$^{52}$ are each and independently represents hydrogen atom, —(CH$_2$)$_m$—OR$^{11}$, (C$_1$–C$_8$)alkyl, —C(=O)—R$^{41}$ —C(=O)—NR$^{11}$R$^{12}$, —(CH$_2$)$_p$-phenyl, thiazol-2-yl or they may combine together to form a pyrrolidino group, a piperidino group, a piperazino group, a morpholino group or a thiomorpholino group, each of which may be substituted by (C$_1$–C$_8$)alkyl or —(CH$_2$)$_m$—OH;

R$^{43}$ is hydrogen atom, —OR$^{51}$, (C$_1$–C$_8$)alkyl, (C$_1$–C$_8$)alkoxy, —(CH$_2$)$_p$-phenyl, NR$^{42}$R$^{52}$, —NH—C(=NH)—NH$_2$, [1,2,4]triazol-4-yl or cyano;

R$^{44}$ and R$^{55}$ are each and independently represents hydrogen atom, (C$_1$–C$_8$)alkyl, —C(=O)—R$^{41}$ or —(CH$_2$)$_p$-phenyl;

R$^{51}$ is hydrogen atom, (C$_1$–C$_8$)alkyl substituted by one or more hydroxy; (C$_2$–C$_8$)alkenyl, (C$_1$–C$_8$)halogenalkyl, —(CH$_2$)$_m$—OR$^{11}$, —(CH$_2$)$_m$—C(=O)—R$^{41}$, —C(=O)—(CH$^2$)$_m$—OR$^4$ or tosyl; A is oxygen atom or ethyleneketal;

is a double bond or a simple bond; m's are each and independently 0, 1 or 2; n is 0 or 1; p's are each and independently 1, 2, 3 or 4.

An example of this class of compounds is shown in formula (IIh)

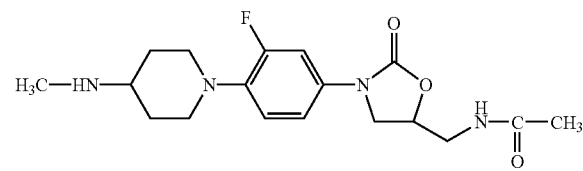

(IIh)

(v) International Patent Application WO 96/13502 discloses compounds of formula (IIi)

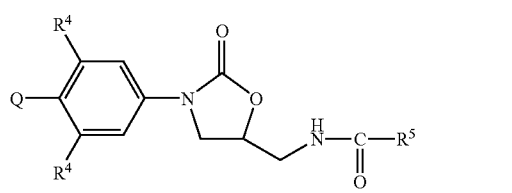

(IIi)

Q is selected from the structures (a), (b), (c), (d) and (e);

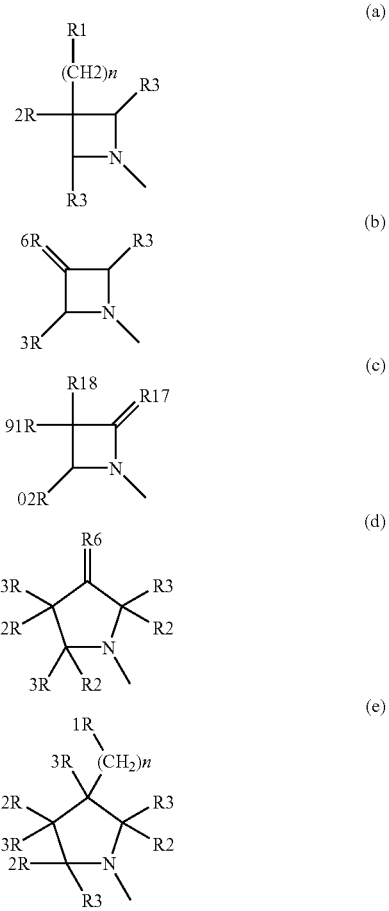

R$^1$ is H or F, OR$^7$, SR$^7$, NR$^8$R$^9$, CN, (C$_1$–C$_4$)alkoxycarbonyl, carboxamide, (C$_1$–C$_4$)acyl optionally substituted with one or more of the following: fluorine, hydroxy, (C$_1$–C$_4$)alkoxy, (C$_1$–C$_4$)acyloxy; NHO(C$_1$–C$_6$)alkyl or NHOCH$_2$Ph, NSO$_2$R where R is (C$_1$–C$_6$)alkyl optionally substituted with one or more F, Cl, (C$_1$–C$_6$)alkoxy or phenyl;

R$^2$ is independently selected from hydrogen or fluorine, hydroxy, OR where R is (C$_1$–C$_6$)alkyl; (C$_1$–C$_4$)alkyl or Ph;

R$^3$ is independently selected from H, phenyl, pyridyl or (C$_1$–C$_3$)alkyl which can be optionally substituted with F, Cl, hydroxy, (C$_1$–C$_3$)alkoxycarbonyl, (C$_1$–C$_3$)acyloxy, (C$_1$–C$_3$)alkoxy or N(C$_1$–C$_4$ alkyl)$_2$;

R$^4$ is independently H, OCH$_3$, F or Cl; R$^5$ is hydrogen, (C$_1$–C$_8$)alkyl optionally substituted with one or more of the following: F, Cl, hydroxy, (C$_1$–C$_8$)alkoxy, (C$_1$–C$_8$)acyloxy; (C$_3$–C$_6$)cycloalkyl, amino, (C$_1$–C$_8$)alkylamino, (C$_1$–C$_8$)dialkylamino, (C$_1$–C$_8$)alkoxy;

R$^6$ is O, S, NR$^{10}$, CR$^{11}$R$^{12}$, (OR)$_2$, where R is (C$_1$–C$_6$) alkyl; O(CH$_2$)$_m$ O, (SR)$_2$ where R is (C$_1$–C$_6$)alkyl; S(CH$_2$)$_m$ S;

R$^7$ is H, (C$_1$–C$_8$)alkyl optionally substituted with one or more of the following: F, Cl, —CN, OH, (C$_1$–C$_8$)alkoxy, (C$_1$–C$_8$)acyloxy, (C$_1$–C$_8$)alkoxycarbonyl, phenyl; (C$_1$–C$_8$) acyl optionally substituted with one or more of the following: hydroxy, (C$_1$–C$_8$) alkoxy, (C$_1$–C$_8$)acyloxy; (C$_1$–C$_8$) alkoxycarbonyl, carboxamide optionally substituted with a (C$_1$–C$_4$)alkyl or phenyl on the carboxamide nitrogen; phenyl, optionally substituted with one or more of the following: halogen, CN, $(C_1-C_3)$ alkoxy, $(C_1-C_3)$alkoxycarbonyl, $(C_1-C_4)$alkyl optionally substituted with one or more of F or $(C_1-C_3)$alkoxy;

$R^8$ and $R^9$ are independently selected from H, $(C_1-C_8)$ alkyl optionally substituted with one or more of the following: F, Cl, —CN, OH, $(C_1-C_8)$alkoxy, $(C_1-C_8)$acyloxy, $(C_1-C_8)$alkoxycarbonyl, phenyl; $(C_1-C_8)$acyl optionally substituted with one or more of the following: hydroxy, $(C_1-C_8)$alkoxy, $(C_1-C_8)$acyloxy, amino, $(C_1-C_4)$acylamino, amino $(C_1-C_4)$acylamino; benzoyl optionally substituted with one or more of the following F, Cl, hydroxy, $(C_1-C_8)$ alkoxy, $(C_1-C_8)$acyloxy, amino, $(C_1-C_4)$acylamino, $(C_1-C_4)$alkoxycarbonylamino; $(C_1-C_8)$alkoxycarbonyl, benzyloxycarbonyl, tertbutoxycarbonyl; carboxamide optionally substituted with a $(C_1-C_4)$alkyl or phenyl on the carboxamide nitrogen; trifluoracetyl, $CO(C_1-C_6$ alkyl$)$;

$R^{10}$ is H, $OR^7$, $NHR^7$, $(C_1-C_8)$alkyl optionally substituted with phenyl;

$R^{11}$ and $R^{12}$ are independently selected from H, F, $(C_1-C_4)$alkyl optionally substituted with halogen, hydroxy, $(C_1-C_4)$alkoxy, $(C_1-C_4)$alkoxycarbonyl, phenyl; $(C_1-C_8)$ acyl, $(C_1-C_4)$alkoxycarbonyl, CN;

$R^{11}$ is O or S; $R^{18}$ and $R^{19}$ are independently selected from H, $(C_1-C_4)$alkyl optionally substituted with halogen, hydroxy, $(C_1-C_4)$alkoxy; OH, $(C_1-C_4)$alkoxy optionally substituted with hydroxy or $(C_1-C_4)$alkoxy; $NR^8R^9$, —OC(O) $(C_1-C_4)$alkyl;

$R^{20}$ is H, $CH_3$; n is 0 or 1; m is 2 or 3.

An example of this class of compounds is shown in formula (IIj)

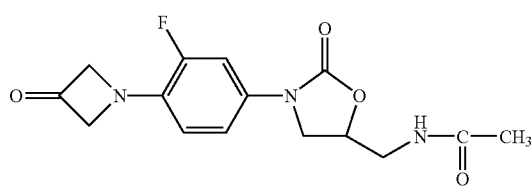

(IIj)

(vi) International Patent Application WO 97/27188 discloses compounds of formula (II k)

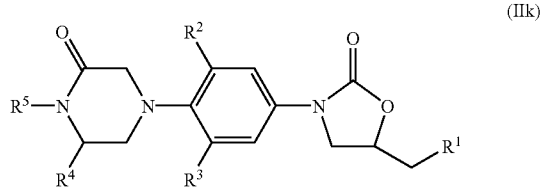

(IIk)

$R^1$ is of the formula —NHC(=O)$(C_1-C_4)$alkyl, —NHS$(O)_n(C_1-C_4)$alkyl, wherein n is 0, 1 or 2 or $R^1$ is hydroxy;

$R^2$ and $R^3$ are independently hydrogen or fluoro;

$R^4$ is hydrogen, methyl, ethyl or oxo;

$R^5$ is hydrogen, $(C_1-C_6)$alkyl, $(C_2-C_6)$alkenyl, $(C_2-C_6)$ alkynyl, or of the formula $R^6(CH_2)_m$ wherein m is 1–4 and $R^6$ is trifluoromethyl, difluoromethyl, fluoromethyl, $(C_1-C_4)$ alkoxy, $(C_1-C_4)$alkyl,$S(O)_p$ wherein p is 0, 1 or 2, $(C_1-C_6)$ alkanoyloxy, di-(N—$(C_1-C_4)$alkyl)amino, N—$((C_1-C_4)$ alkyl)$(C_1-C_4)$alkanoylamino, cyano, carboxy, $(C_1-C_4)$ alkoxycarbonyl, carbamoyl, -di-(N—$(C_1-C_4)$alkyl) carbamoyl, N—$((C_1-C_4)$alkyl)$(C_1-C_4)$ alkanesulphonamido, $N^1$—$((C_1-C_4)$alkyl$)$-di-$(N^3$—$(C_1-C_4)$ alkyl)ureido or of the formula —OC(=O)NR($R^8$) or N($R^9$) $SO_2NR^7(R^8)$ wherein $R^7$ and $R^8$ are independently hydrogen or $(C_1-C_4)$alkyl and $R^9$ is $(C_1-C_4)$ alkyl; or m is 2–4 and $R^6$ is hydroxy, $(C_1-C_4)$alkanoylamino, amino, $(C_1-C_4)$alkylamino, $(C_1-C_4)$alkanesulphonamido, ureido, di-$(N^3$—$(C_1-C_4)$alkyl)ureido or of the formula $NHSO_2NR^7(R^8)$.

An example of this compound is shown in fig (III)

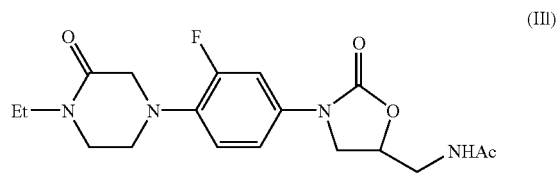

(III)

(vii) International Patent Application WO 98/01446 discloses compounds of formula (IIm)

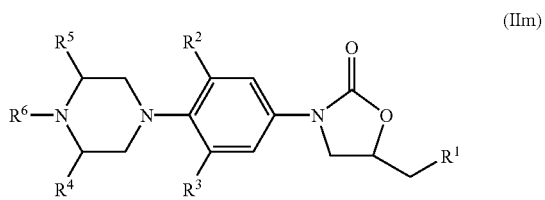

(IIm)

$R^1$ is of the formula —NHC(=O)$R^a$ wherein $R^a$ is $(C_1-C_4)$alkyl;

$R^2$ and $R^3$ are independently hydrogen or fluoro;

$R^4$ and $R^5$ are independently hydrogen or methyl;

$R^6$ is a 6-membered heteroaryl ring containing 2 or 3 ring nitrogen atoms as the only ring heteroatoms and optionally substituted by substituents selected from $(C_1-C_4)$alkyl (optionally substituted), halo, trifluoromethyl, $(C_1-C_4)$alkylS$(O)_n$- (wherein n is 0, 1 or 2), $(C_1-C_4)$alkylS$(O)_2$ amino, $(C_1-C_4)$alkanoylamino, carboxy, hydroxy, amino, $(C_1-C_4)$ alkylamino, di$(C_1-C_4)$alkylamino, $(C_1-C_4)$alkoxycarbonyl, carbamoyl, N—$(C_1-C_4)$alkylcarbamoyl, -di-(N—$(C_1-C_4)$ alkyl)carbamoyl, (wherein $(C_1-C_4)$alkyl group or groups in the last two mentioned carbamoyl substituents is optionally substituted by hydroxy, $(C_1-C_4)$alkoxy or $(C_1-C_4)$alkoxycarbonyl), $(C_2-C_4)$alkenyl (optionally substituted by carboxy or $(C_1-C_4)$alkoxycarbonyl), $(C_1-C_4)$alkoxy, cyano or nitro.

An example of this compound is shown in fig (III)

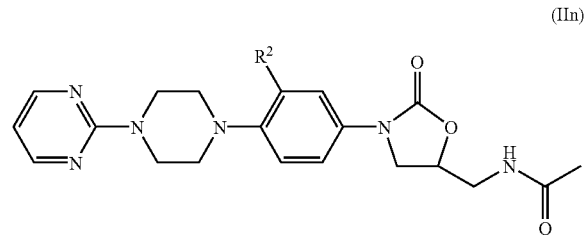

(IIn)

SUMMARY OF THE INVENTION

With an objective to develop novel compounds effective against a number of human and veterinary pathogens, including gram-positive aerobic bacteria such as MRSA, streptococci and enterococci as well as anaerobic organisms such as *Bacteroides* spp, *Clostridia* spp. species and acid-fast organisms such as *Mycobacterium tuberculosis, Mycobacterium aviumn* and *Mycobacterium* spp., we focussed our research to develop new compounds effective against the above mentioned organisms. Efforts in this direction have led to the preparation of compounds having general formula (I) as defined above.

The present invention provides novel Oxazolidinones of the general formula (I) as defined above and their derivatives, their analogs, their tautomeric forms, their stereoisomers, their polymorphs, their pharmaceutically acceptable salts, their pharmaceutically acceptable solvates and pharmaceutical compositions containing them, or their mixtures having enhanced activities, without toxic effect or with reduced toxic effect.

A process for the preparation of novel oxazolidinones of the formula (I) as defined above and their derivatives, their analogs, their tautomeric forms, their stereoisomers, their polymorphs, their pharmaceutically acceptable salts and their pharmaceutically acceptable solvates is also described.

An aspect of the present invention is to provide pharmaceutical compositions containing compounds of the general formula (I), their analogs, their derivatives, their tautomers, their stereoisomers, their polymorphs, their salts, solvates or their mixtures in combination with suitable carriers, solvents, diluents and other media normally employed in preparing such compositions.

Novel intermediates of formulae (VI), (VII), (X), (XVI) and (XVIII) and a process for their preparation and their use in the preparation of compounds of formula (I) is also provided.

DETAILED DESCRIPTION OF THE INVENTION

The present invention relates to compounds having the general formula (I)

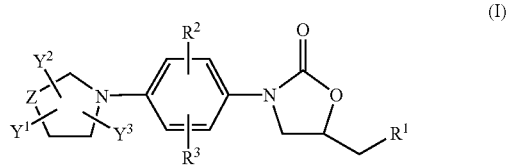

(I)

where $R^1$ represents halo, azido, thioalcohol, isothiocyanate, $OR^4$, $NHR^4$ or $N(R^4)_2$, where $R^4$ represents hydrogen atom, or substituted or unsubstituted groups selected from acyl, thioacyl, $(C_1-C_6)$alkoxycarbonyl, cyclo$(C_3-C_6)$alkoxythiocarbonyl, $(C_2-C_6)$alkenyloxycarbonyl, $(C_2-C_6)$alkenylcarbonyl, aryloxycarbonyl, $(C_1-C_6)$alkoxythiocarbonyl, $(C_2-C_6)$alkenyloxythiocarbonyl, aryloxythiocarbonyl, —C(=O)—C(=O)—$(C_1-C_6)$alkyl, —C(=O)—C(=O)-aryl, —C(=O)—C(=O)—$(C_1-C_6)$alkoxy, —C(=O)—C(=O)-aryloxy, —(C=S)—S—$(C_1-C_6)$alkyl, —(C=S)—$NH_2$, —(C=S)—NH—$(C_1-C_6)$alkyl, —C(=S)—N—$((C_1-C_6)alkyl)_2$, —C(=S)—NH—$(C_2-C_6)$alkenyl, (C=S)—(C=O)—$(C_1-C_6)$alkoxy, —(C=S)—(C=O)-aryloxy, —C(=S)—O—(C=O)—$(C_1-C_6)$alkyl, C(=S)—C(=S)—$(C_1-C_6)$alkyl, —C(=S)—C(=S)-aryl, thiomorpholinylthiocarbonyl or pyrrolidinylthiocarbonyl;

$R^2$ and $R^3$ may be same or different and independently represent hydrogen, halogen atom, $(C_1-C_6)$alkyl group, halo$(C_1-C_6)$alkyl, cyano, nitro, $SR^a$, $NR^a$, or $OR^a$ where $R^a$ represents substituted or unsubstituted $(C_1-C_6)$alkyl group, or halo$(C_1-C_6)$alkyl;

Z represents S, O, =CH or $NR^b$ where $R^b$ represents hydrogen or substituted or unsubstituted $(C_1-C_6)$alkyl, $(C_2-C_6)$alkenyl, $(C_1-C_6)$cycloalkyl, $(C_1-C_6)$alkoxy, aryl, aralkyl, aryloxy, $(C_1-C_6)$alkylcarbonyl, arylcarbonyl, $(C_1-C_6)$lkoxycarbonyl or aryloxycarbonyl;

$Y^1$ represents =O or =S group and $Y^2$ and $Y^3$ independently represent hydrogen, halogen, cyano, nitro, formyl, hydroxy, amino, =O, =S group or substituted or unsubstituted groups selected from $(C_1-C_6)$alkyl, hydroxy$(C_1-C_6)$alkyl, $(C_1-C_6)$alkoxy$(C_1-C_6)$alkyl, $(C_1-C_6)$alkoxycarbonyl, carboxy$(C_1-C_6)$alkyl, $(C_1-C_6)$alkylsulfonyl, $(C_1-C_6)$alkylcarbonylamino$(C_1-C_6)$alkyl, arylcarbonylamino $C_1-C_6$) alkyl, $(C_1-C_6)$alkylcarbonyloxy$(C_1-C_6)$alkyl, amino$(C_1-C_6)$alkyl, mono$(C_1-C_6)$alkylamino, di$(C_1-C_6)$alkylamino, arylamino, $(C_1-C_6)$alkoxy, aryl, aryloxy, aralkyl, heteroaryl, heteroaralkyl, heterocyclyl or heterocycloalkyl;

$Y^2$ and $Y^3$ when present on adjacent carbon atoms together may also form a substituted or unsubstituted 5 or 6 membered aromatic or non-aromatic cyclic structure, optionally containing one or two hetero atoms; its derivatives, its analogs, its tautomeric forms, its stereoisomers, its polymorphs, its pharmaceutically acceptable salts or its pharmaceutically acceptable solvates.

Suitable groups represented by $R^4$ may be selected from hydrogen atom, $(C_1-C_7)$acyl group such as —C(=O)H, —C(=O)CH₃, —C(=O)CH₂CH₃, —C(=O)(CH₂)₂CH₃, —C(=O)(CH₂)₃CH₃, —C(=O)(CH₂)₄CH₃, —C(=O)(CH₂)₅CH₃, —C(=O)phenyl and the like, the acyl group may be substituted; thio$(C_1-C_7)$acyl group such as —C(=S)H, —C(=S)CH₃, —C(=S)CH₂CH₃, —C(=S) Ph and the like, the thioacyl group may be substituted; $(C_1-C_6)$alkoxycarbonyl group containing $(C_1-C_6)$alkyl group which may be linear or branched such as methoxycarbonyl, ethoxycarbonyl, propoxycarbonyl, isopropoxycarbonyl and the like, the $(C_1-C_6)$alkoxycarbonyl group may be substituted; cyclo$(C_3-C_6)$alkoxythiocarbonyl group such as cyclopropoxythiocarbonyl, cyclobutoxythiocarbonyl and the like, the cyclo$(C_3-C_6)$alkoxythiocarbonyl may be substituted; $(C_2-C_6)$alkenylcarbonyl such as ethenylcarbonyl, propenylcarbonyl, butenylcarbonyl and the like, the $(C_2-C_6)$ alkenylcarbonyl may be substituted; $(C_2-C_6)$alkenyloxycarbonyl group such as ethenyloxycarbonyl, propenyloxycarbonyl, butenyloxycarbonyl and the like, the $(C_2-C_6)$ alkenyloxycarbonyl may be substituted; aryloxycarbonyl group such as phenoxycarbonyl, benzyloxycarbonyl group and the like, the aryloxycarbonyl group may be substituted; $(C_1-C_6)$alkoxythiocarbonyl group such as CH₃O—C(=S)—, C₂H₅O—C(=S)—C₃H₇O—C(=S)— and the like, which may be substituted; $(C_2-C_6)$alkenyloxythiocarbonyl group such as ethenyloxythiocarbonyl, propenyloxythiocarbonyl, butenyloxythiocarbonyl and the like, the $(C_2-C_6)$alkenyloxythiocarbonyl group may be substituted; aryloxythiocarbonyl group such as phenyl-O—C(=S)—, benzyl-O—C(=S)— and the like, which may be substituted; —C(=O)—C(=O)—$(C_1-C_6)$alkyl group such as —C(=O)—C(=O)methyl, —C(=O)—C(=O)ethyl, —C(=O)—C(=O)propyl and the like, which may be substituted; —C(=O)—C(=O)-aryl group such as —C(=O)—C(=O)phenyl, —C(=O)—C(=O)naphthyl and the like, which may be substituted; —C(=O)—C(=O)—($C_1$–$C_6$)alkoxy group such as —C(=O)—C(=O)methoxy, —C(=O)—C(=O)ethoxy, —C(=O)—C(=O)propyloxy and the like, which may be substituted; —C(=O)—C(=O)-aryloxy group such as —C(=O)—C(=O)phenyloxy, —C(=O)—C(=O)benzyloxy, which may be substituted; —(C=S)—S—($C_1$–$C_6$)alkyl such as —(C=S)—S-methyl, —(C=S)—S-ethyl, —(C=S)—S-propyl and the like, which may be substituted; —(C=S)—$NH_2$; —(C=S)—NH—($C_1$–$C_6$)alkyl such as —(C=S)—NH-methyl, —(C=S)—NH-ethyl, —(C=S)—NH-propyl and the like, which may be substituted; —C(=S)—N—(($C_1$–$C_6$)alkyl)$_2$ such as —C(=S)—N-(methyl)$_2$, —C(=S)—N-(ethyl)$_2$, —C(=S)—N-(propyl)$_2$ and the like, which may be substituted; —C(=S)—NH—($C_2$–$C_6$)alkenyl such as —C(=S)—NH-ethenyl, —C(=S)—NH-propenyl, —C(=S)—NH-butenyl and the like, which may be substituted; —(C=S)—(C=O)—($C_1$–$C_6$)alkoxy such as —(C=S)—(C=O)-methoxy, —(C=S)—(C=O)-ethoxy, —(C=S)—(C=O)-propoxy and the like, which may be substituted; —(C=S)—(C=O)-aryloxy such as —(C=S)—(C=O)-phenyloxy, —(C=S)—(C=O)-naphthyloxy and the like, which may be substituted; —C(=S)—O—(C=O)—($C_1$–$C_6$)alkyl such as —C(=S)—O—(C=O)-methyl, —C(=S)—O—(C=O)-ethyl, —C(=S)—O—(C=O)-propyl and the like, which may be substituted; —C(=S)—C(=S)—($C_1$–$C_6$)alkyl group such as —C(=S)—C(=S)methyl, —C(=S)—C(=S)ethyl, —C(=S)—C(=S)propyl and the like, which may be substituted; —C(=S)—C(=S)aryl group such as —C(=S)—C(=S)phenyl, —C(=S)—C(=S)naphthyl and the like, which may be substituted; thiomorpholinylthiocarbonyl or pyrrolidinylthiocarbonyl.

When the groups represented by $R^4$ are substituted, the substituents may be selected from halogen atom such as chlorine, fluorine, bromine and iodine; hydroxy, amino, mono($C_1$–$C_6$)alkylamino such as methylamino, ethylamino, propylamino and the like, di($C_1$–$C_6$)alkylamino such as dimethylamino, diethylamino, methylethylamino, dipropylamino, ethylpropylamino and the like, cyano, nitro, alkoxy, aryl, hydroxyaryl, pyridyl, hydroxyalkyl, alkoxyaryl or carboxyl and its derivatives. Alkoxy is a ($C_1$–$C_6$)alkoxy group and aryl is phenyl or naphthyl.

Suitable groups represented by $R^2$ and $R^3$ may be selected from hydrogen, halogen atom such as fluorine, chlorine or bromine; ($C_1$–$C_6$)alkyl group such as methyl, ethyl, n-propyl, isopropyl, n-butyl, iso-butyl, t-butyl, n-pentyl, iso-pentyl, n-hexyl and the like; halo($C_1$–$C_6$)alkyl group such as halomethyl, haloethyl, halopropyl, trihalomethyl and the like, wherein the halo group is selected from fluorine, chlorine, bromine or iodine; cyano, nitro; $SR^a$, $NR^a$, $OR^a$ where $R^a$ represents substituted or unsubstituted ($C_1$–$C_6$) alkyl group such as methyl, ethyl, propyl, isopropyl and the like; halo($C_1$–$C_6$)alkyl such as halomethyl, haloethyl, halopropyl, haloisopropyl and the like, where the halo group is selected from fluro, chloro, bromo or iodo.

The substituents on $R^a$ are selected from hydroxy, halogen, nitro, amino, alkoxy, carboxyl or cyano. Alkoxy is a ($C_1$–$C_6$)alkoxy group.

Suitable groups represented by Z may be selected from S, O, =CH or $NR^b$ where $R^b$ represents hydrogen or substituted or unsubstituted ($C_1$–$C_6$)alkyl such as methyl, ethyl, propyl and the like, which may be substituted; ($C_2$–$C_6$) alkenyl such as ethenyl, propenyl, butenyl and the like, which may be substituted; ($C_1$–$C_6$)cycloalkyl such as cyclopropyl, cyclobutyl and the like, which may be substituted; ($C_1$–$C_6$)alkoxy such as methoxy, propoxy, isopropoxy and the like, which may be substituted; aryl group such as phenyl, naphthyl and the like, which may be substituted; aralkyl such as benzyl, phenethyl and the like, which may be substituted; aryloxy such as phenyloxy, naphthyloxy and the like, which may be substituted; ($C_1$–$C_6$)alkylcarbonyl such as methylcarbonyl, ethylcarbonyl, propylcarbonyl and the like, which may be substituted; arylcarbonyl such as phenylcarbonyl, naphthylcarbonyl and the like, which may be substituted; ($C_1$–$C_6$)alkoxycarbonyl such as methoxycarbonyl, ethoxycarbonyl, propoxycarbonyl and the like, which may be substituted; or aryloxycarbonyl such as phenyloxycarbonyl, naphthyloxycarbonyl and the like, which may be substituted.

The substituents on $R^b$ are selected from hydroxy, halogen, pyrrolidinylthiocarbonyl, nitro, amino, alkoxy, carboxyl or cyano. Alkoxy is a ($C_1$–$C_6$)alkoxy group.

$Y^1$ represents =O or =S group, $Y^2$ and $Y^3$ are selected from hydrogen, halogen such as fluorine, chlorine, bromine or iodine; cyano, nitro, formyl, hydroxy, amino, =O, =S group, substituted or unsubstituted ($C_1$–$C_6$)alkyl such as methyl, ethyl, n-propyl, isopropyl, n-butyl, iso-butyl, t-butyl and the like; hydroxy($C_1$–$C_6$)alkyl such as hydroxymethyl, hydroxyethyl, hydroxypropyl and the like, which may be substituted; ($C_1$–$C_6$)alkoxy($C_1$–$C_6$)alkyl group such as methoxymethyl, methoxyethyl, ethoxyethyl, ethoxymethyl, methoxypropyl, propoxymethyl, propoxyethyl and the like, which may be substituted; ($C_1$–$C_6$)alkoxycarbonyl group such as methoxycarbonyl, ethoxycarbonyl and the like, which may be substituted; carboxy($C_1$–$C_6$)alkyl such as $CH_3$—COOH, $CH_3$—$CH_2$—COOH and the like, which may be substituted; ($C_1$–$C_6$)alkylsulfonyl group such as methylsulfonyl, ethylsulfonyl and the like, which may be substituted; ($C_1$–$C_6$)alkylcarbonylamino($C_1$–$C_6$)alkyl groups such as methylcarbonylaminomethyl, ethylcarbonylaminomethyl, methylcarbonylaminoethyl, ethylcarbonylaminoethyl and the like, which may be substituted; arylcarbonylamino($C_1$–$C_6$)alkyl such as phenylcarbonylaminomethyl, phenylcarbonylaminoethyl, naphthylcarbonylaminomethyl, naphthylcarbonylaminoethyl and the like, which may be substituted; ($C_1$–$C_6$)alkylcarbonyloxy($C_1$–$C_6$)alkyl group such as methylcarbonyloxymethyl, ethylcarbonylxoymethyl, methylcarbonyloxyethyl, propylcarbonyloxymethyl, propylcarbonyloxyethyl, propylcarbonyloxypropyl and the like, which may be substituted; amino($C_1$–$C_6$)alkyl such as aminomethyl, aminoethyl, aminopropyl and the like, which may be substituted; mono($C_1$–$C_6$)alkylamino such as methylamino, ethylamino, propylamino and the like, which may be substituted; di($C_1$–$C_6$)alkylamino such as dimethylamino, diethylamino, methylethylamino, dipropylamino, ethylpropylamino and the like, which may be substituted; arylamino such as phenylamino, benzylamino and the like, which may be substituted; ($C_1$–$C_6$)alkoxy group such as methoxy, ethoxy, propoxy, isopropoxy and the like, which may be substituted; aryl group such as phenyl, naphthyl and the like, which may be substituted; aryloxy group such as phenoxy, naphthyloxy and the like, the aryloxy group may be substituted; aralkyl such as benzyl, phenethyl, $C_6H_5CH_2CH_2CH_2$, naphthylmethyl and the like, the aralkyl group may be substituted; heteroaryl groups such as pyridyl, thienyl, furyl, pyrrolyl, oxazolyl, thiazolyl, pyrazolyl, imidazolyl, oxadiazolyl, tetrazolyl, benzopyranyl, benzofuranyl and the like, which may be substituted; heteroaralkyl such as imidazolemethyl, imidazoleethyl, pyridylmethyl, furyl methyl, oxazolemethyl, imidazolyl and the like, which may be substituted; heterocyclyl group such as pyrrolidinyl, piperidinyl, morpholinyl, piperazinyl and the like; heterocycloalkyl groups such as pyrrolidinemethyl, piperidinemethyl, morpholinemethyl, piperazinemethyl and the like, which may be substituted.

When the groups represented by $Y^2$ and $Y^3$ are substituted, the substituents may be selected from hydroxy, nitro, cyano, amino, (tert-butyldimethylsilyloxy) TBSO, halogen atom, $(C_1-C_6)$alkyl, $(C_1-C_6)$alkoxy, $(C_3-C_6)$cycloalkyl, aryl group such as phenyl, naphthyl and the like, benzyloxy, acyl group such as formyl, acetyl, and the like, carboxyl or acyloxy group such as formyloxy, acetyloxy and the like.

Suitable cyclic structure formed by $Y^2$ and $Y^3$ when present on adjacent carbon atoms which they are attached may be selected from substituted or unsubstituted benzene, pyridine, pyrrolidine, furan, thiophene, morpholine, piperazine, pyrrole and the like.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids such as D-isomers or substituted amino acids; guanidine, substituted guanidine wherein the substituents are selected from nitro, amino, alkyl such as methyl, ethyl, propyl and the like; alkenyl such as ethenyl, propenyl, butenyl and the like; alkynyl such as ethynyl, propynyl and the like; ammonium or substituted ammonium salts and aluminum salts. Salts may include acid addition salts where appropriate which are, sulphates, nitrates, phosphates, perchlorates, borates, halides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to this invention include:
(5R)-3-[3-fluoro-4-(2-oxo-1,3-oxazolan-3-yl)phenyl]-5-hydroxymethyl-1,3-oxazolan-2-one or its salts;
  (5R)-3-[3-fluoro-4-(2-thioxo-1,3-oxazolan-3-yl)phenyl]-5-hydroxymethyl-1,3-oxazolan-2-one or its salts;
  (5R)-3-[3-fluoro-4-(2-thioxo-1,3-thiazolan-3-yl)phenyl]-5-hydroxymethyl-1,3-oxazolan-2-one or its salts;
  (5R)-3-[3-fluoro-4-(3-methyl-2-thioxo-1-imidazolidinyl)phenyl]-5-hydroxymethyl-1,3-oxazolan-2-one or its salts;
  3-{2-fluoro-4-[(5R)-5-hydroxymethyl-2-oxo-1,3-oxazolan-3-yl]phenyl}-2,3-dihydrobenzo[d][1,3]oxazol-2-one or its salts;
  3-{2-fluoro-4-[(5R)-5-hydroxymethyl-2-oxo-1,3-oxazolan-3-yl]phenyl}-6-methyl-2,3-dihydrobenzo[d][1,3]oxazol-2-one or its salts;
  3-{2-fluoro-4-[(5R)-5-hydroxymethyl-2-oxo-1,3-oxazolan-3-yl]phenyl}-5-methyl-2,3-dihydrobenzo[d][1,3]oxazol-2-one or its salts;
  (5R)-5-hydroxymethyl-3-[4-(2-oxo-1,3-oxazolan-3-yl)-3-trifluoromethylphenyl]-1,3-oxazolan-2-one or its salts;
  (5R)-3-[2-fluoro-4-(2-oxo-1,3-oxazolan-3-yl)phenyl]-5-hydroxymethyl-1,3-oxazolan-2-one or its salts;
  (5R)-3-[3,5-fluoro-4-(2-oxo-1,3-oxazolan-3-yl)phenyl]-5-hydroxymethyl-1,3-oxazolan-2-one or its salts;
  (5R)-5-hydroxymethyl-3-[4-(2-oxo-1,3-oxazolan-3-yl)phenyl]-1,3-oxazolan-2-one or its salts;
  3-{4-[(5R)-5-hydroxymethyl-2-oxo-1,3-oxazolan-3-yl]phenyl}-2,3-dihydrobenzo[d][1,3]oxazol-2-one or its salts;
  (5R)-3-[3-fluoro-4-(3-methyl-4-oxo-1-imidazolidinyl)phenyl]-5-hydroxymethyl-1,3-oxazolan-2-one or its salts;
  (5R)-3-{3-fluoro-4-[3-(4-methoxybenzyl)-4-oxo-1-imidazolidinyl]phenyl}-5-hydroxymethyl-1,3-oxazolan-2-one or its salts;
  (5R)-3-[3-fluoro-4-(3-methyl-2-oxo-1-imidazolidinyl)phenyl]-5-hydroxymethyl-1,3-oxazolan-2-one or its salts;
  (5R)-5-hydroxymethyl-3-[4-(3-methyl-2-oxo-1-imidazolidinyl)phenyl]-1,3-oxazolan-2-one or its salts;
  (5R)-5-hydroxymethyl-3-[4-(3-benzyl-2-oxo-1-imidazolidinyl)phenyl]-1,3-oxazolan-2-one or its salts;
  (5R)-3-[3-fluoro-4-(2-oxo-3-phenyl-1-imidazolidinyl)phenyl]-5-hydroxymethyl-1,3-oxazolan-2-one or its salts;
  (5R)-3-{3-fluoro-4-[3-(fluorophenyl)-2-oxo-1-imidazolidinyl]phenyl}-5-hydroxymethyl-1,3-oxazolan-2-one or its salts;
  (5R)-azidomethyl-3-[3-fluoro-4-(2-oxo-1,3-oxazolan-3-yl)phenyl]-1,3-oxazolan-2-one or its salts;
  (5R)-azidomethyl-3-[3-fluoro-4-(3-methyl-2-thioxo-1-imidazolidinyl)phenyl]-1,3-oxazolan-2-one or its salts;
  3-{4-[(5R)-5-azidomethyl-2-oxo-1,3-oxazolan-3-yl]-2-fluorophenyl}-6-methyl-2,3-dihydro benzo[d][1,3]oxazol-2-one or its salts;
  3-{4-[(5R)-5-azidomethyl-2-oxo-1,3-oxazolan-3-yl]-2-fluorophenyl}-5-methyl-2,3-dihydro benzo[d][1,3]oxazol-2-one or its salts;
  (5R)-5-azidomethyl-3-[4-(2-oxo-1,3-oxazolan-3-yl)-3-trifluoromethylphenyl]-1,3-oxazolan-2-one or its salts;
  (5R)-5-azidomethyl-3-[2-fluoro-4-(2-oxo-1,3-oxazolan-3-yl)phenyl]-1,3-oxazolan-2-one or its salts;
  (5R)-azidomethyl-3-[3,5-difluoro-4-(2-oxo-1,3-oxazolan-3-yl)phenyl]-1,3-oxazolan-2-one or its salts;
  (5R)-5-azidomethyl-3-[4-(2-oxo-1,3-oxazolan-3-yl)phenyl]-1,3-oxazolan-2-one or its salts;
  3-{4-[(5R)-5-azidomethyl-2-oxo-1,3-oxazolan-3-yl]phenyl}-2,3-dihydrobenzo[d][1,3]oxazol-2-one or its salts;
  (5R)-5-azidomethyl-3-[3-fluoro-4-(3-methyl-4-oxo-1-imidazolidinyl)phenyl]-1,3-oxazolan-2-one or its salts;
  (5R)-5-azidomethyl-3-[3-fluoro-4-(3-phenyl-2-oxo-1-imidazolidinyl)phenyl]-1,3-oxazolan-2-one or its salts;
  (5R)-5-azidomethyl-3-{3-fluoro-4-[3-(4-fluorophenyl)-2-oxo-1-imidazolidinyl]phenyl}-1,3-oxazolan-2-one or its salts;
  (5R)-aminomethyl-3-[3-fluoro-4-(2-oxo-1,3-oxazolan-3-yl)phenyl]-1,3-oxazolan-2-one or its salts;

(5R)-aminomethyl-3-[3-fluoro-4-(3-methyl-2-thioxo-1-imidazolidinyl)phenyl]-1,3-oxazolan-2-one or its salts;
(5R)-5-aminomethyl-3-[4-(2-oxo-1,3-oxazolan-3-yl)-3-trifluoromethylphenyl]-1,3-oxazolan-2-one or its salts;
(5R)-5-aminomethyl-3-[4-(2-oxo-1,3-oxazolan-3-yl)phenyl]-1,3-oxazolan-2-one or its salts;
(5R)-5-aminomethyl-3-[3-fluoro-4-(3-methyl-4-oxo-1-imidazolidinyl)phenyl]-1,3-oxazolan-2-one or its salts;
(5R)-5-aminomethyl-3-[3-fluoro-4-(3-benzyl-4-oxo-1-imidazolidinyl)phenyl]-1,3-oxazolan-2-one or its salts;
N-{(5S)-3-[3-fluoro-4-(2-oxo-1,3-oxazolan-3-yl)phenyl]-2-oxo-1,3-oxazolan-5-ylmethyl}methanamide or its salts;
N-{(5S)-3-[3,5-difluoro-4-(2-oxo-1,3-oxazolan-3-yl)phenyl]-2-oxo-1,3-oxazolan-5-ylmethyl}methanamide or its salts;
N1-{(5S)-3-[3-fluoro-4-(2-oxo-1,3-oxazolan-3-yl)phenyl]-2-oxo-1,3-oxazolan-5-ylmethyl}acetamide or its salts;
N1-{(5S)-3-[3-fluoro-4-(2-oxo-1,3-oxazolan-3-yl)phenyl]-2-oxo-1,3-oxazolan-5-ylmethyl}propanamide or its salts;
N1-{(5S)-3-[3-fluoro-4-(2-oxo-1,3-oxazolan-3-yl)phenyl]-2-oxo-1,3-oxazolan-5-ylmethyl}butanamide or its salts;
N1-{(5S)-3-[3-fluoro-4-(2-oxo-1,3-oxazolan-3-yl)phenyl]-2-oxo-1,3-oxazolan-5-ylmethyl}pentanamide or its salts;
N1-{(5S)-3-[3-fluoro-4-(2-oxo-1,3-oxazolan-3-yl)phenyl]-2-oxo-1,3-oxazolan-5-ylmethyl}heptanamide or its salts;
N1-{(5S)-3-[3-fluoro-4-(2-oxo-1,3-oxazolan-3-yl)phenyl]-2-oxo-1,3-oxazolan-5-ylmethyl}acrylamide or its salts;
N1-{(5S)-3-[3-fluoro-4-(2-oxo-1,3-oxazolan-3-yl)phenyl]-2-oxo-1,3-oxazolan-5-ylmethyl}-2,2,2-trifluoroacetamide or its salts;
Ethyl(5S)-3-[3-fluoro-4-(2-oxo-1,3-oxazolan-3-yl)phenyl]-2-oxo-1,3-oxazolan-5-ylmethyl carbamoylmethanoate or its salts;
N1-{(5S)-3-[3-fluoro-4-(2-thioxo-1,3-oxazolan-3-yl)phenyl]-2-oxo-1,3-oxazolan-5-ylmethyl}acetamide or its salts;
N1-{(5S)-2-oxo-3-[4-(2-thioxo-1,3-oxazolan-3-yl)phenyl]-1,3-oxazolan-5-ylmethyl}acetamide or its salts;
N1-{(5S)-2-oxo-3-[3-fluoro-4-(2-thioxo-1,3-thiazolan-3-yl)phenyl]-1,3-oxazolan-5-ylmethyl}acetamide or its salts;
N1-{(5S)-3-[3-fluoro-4-(3-methyl-2-thioxo-1-imidazolidinyl)henyl]-2-oxo-1,3-oxazolan-5-ylmethyl}acetamide or its salts;
N1-{(5S)-3-[3-fluoro-4-(2-oxo-2,3-dihydrobenzo[d][1,3]oxazol-3-yl)phenyl]-2-oxo-1,3-oxazolan-5-ylmethyl}acetamide or its salts;
N1-{(5S)-3-[3-fluoro-4-(6-methyl-2-oxo-2,3-dihydrobenzo[d][1,3]oxazol-3-yl)phenyl]-2-oxo-1,3-oxazolan-5-ylmethyl}acetamide or its salts;
N1-{(5S)-3-[3-fluoro-4-(5-methyl-2-oxo-2,3-dihydrobenzo[d][1,3]oxazol-3-yl)phenyl]-2-oxo-1,3-oxazolan-5-ylmethyl}acetamide or its salts;
N1-{(5S)-2-oxo-3-[4-(2-oxo-1,3-oxazolan-3-yl)-3-trifluoromethylphenyl]-1,3-oxazolan-5-ylmethyl}acetamide or its salts;
N1-{(5S)-2-oxo-3-[4-(2-oxo-1,3-oxazolan-3-yl)-3-trifluoromethylphenyl]-1,3-oxazolan-5-ylmethyl}propanamide or its salts;
N1-{(5S)-2-oxo-3-[4-(2-oxo-1,3-oxazolan-3-yl)-3-trifluoromethylphenyl]-1,3-oxazolan-5-ylmethyl}heptanamide or its salts;
N1-{(5S)-2-oxo-3-[4-(2-oxo-1,3-oxazolan-3-yl)-3-trifluoromethylphenyl]-1,3-oxazolan-5-ylmethyl}acrylamide or its salts;
N1-{(5S)-3-[2-fluoro-4-(2-oxo-1,3-oxazolan-3-yl)phenyl]-2-oxo-1,3-oxazolan-5-ylmethyl}acetamide or its salts;
N1-{(5S)-3-[3,5-difluoro-4-(2-oxo-1,3-oxazolan-3-yl)phenyl]-oxo-1,3-oxazolan-5-ylmethyl}acetamide or its salts;
N1-{(5S)-3-[3,5-difluoro-4-(2-oxo-1,3-oxazolan-3-yl)phenyl]-2-oxo-1,3-oxazolan-5-ylmethyl}propanamide or its salts;
N1-{(5S)-2-oxo-3-[4-(2-oxo-1,3-oxazolan-3-yl)phenyl]-1,3-oxazolan-5-ylmethyl}acetamide or its salts;
N1-{(5S)-2-oxo-3-[4-(2-oxo-2,3-dihydrobenzo[d][1,3]oxazol-3-yl)phenyl]-1,3-oxazolan-5-ylmethyl}acetamide or its salts;
N1-{(5S)-3-[3-fluoro-4-(3-methyl-4-oxo-1-imidazolidinyl)phenyl]-2-oxo-1,3-oxazolan-5-ylmethyl}acetamide or its salts;
N1-{(5S)-3-[3-fluoro-4-(3-benzyl-4-oxo-1-imidazolidinyl)phenyl]-2-oxo-1,3-oxazolan-5-ylmethyl}acetamide or its salts;
N1-{(5S)-3-[3-fluoro-4-(3-methyl-2-thioxo-1-imidazolidinyl)phenyl]-2-oxo-1,3-oxazolan-5-ylmethyl}acetamide or its salts;
N1-{(5S)-3-[4-(3-methyl-2-oxo-1-imidazolidinyl)phenyl]-2-oxo-1,3-oxazolan-5-ylmethyl}acetamide or its salts;
N1-{(5S)-3-[4-(3-benzyl-2-oxo-1-imidazolidinyl)phenyl]-2-oxo-1,3-oxazolan-5-ylmethyl}acetamide or its salts;
N1-{(5S)-3-[3-fluoro-4-(3-phenyl-2-oxo-1-imidazolidinyl)phenyl]-2-oxo-1,3-oxazolan-5-ylmethyl}acetamide or its salts;
N1-((5S)-3-{3-fluoro-4-[3-(4-fluorophenyl)-2-oxo-1-imidazolidinyl]phenyl}-2-oxo-1,3-oxazolan-5-ylmethyl)acetamide or its salts;
(5S)-3-[3-fluoro-4-(2-oxo-1,3-oxazolan-3-yl)phenyl]-5-(1-thioxoethylaminomethyl)-1,3-oxazolan-2-one or its salts;
(5S)-3-[3-fluoro-4-(2-oxo-1,3-oxazolan-3-yl)phenyl]-5-(3,3,3-trifluoro-1-thioxopropylaminomethyl)-1,3-oxazolan-2-one or its salts;
(5S)-3-[3-fluoro-4-(3-methyl-2-thioxo-1-imidazolidinyl)phenyl]-5-(1-thioxoethylaminomethyl)-1,3-oxazolan-2-one or its salts;
3-{2-fluoro-4-[(5S)-2-oxo-5-(1-thioxoethylaminomethyl)-1,3-oxazolan-3-yl]phenyl}-2,3-dihydrobenzo[d][1,3]oxazol-2-one or its salts;
(5S)-3-[4-(2-oxo-1,3-oxazolan-3-yl)-3-trifluoromethylphenyl]-5-(1-thioxoethylaminomethyl)-1,3-oxazolan-2-one or its salts;
(5S)-3-[3,5-difluoro-4-(2-oxo-1,3-oxazolan-3-yl)phenyl]-5-(1-thioxoethylaminomethyl)-1,3-oxazolan-2-one or its salts;
(5S)-3-[3,5-difluoro-4-(2-oxo-1,3-oxazolan-3-yl)phenyl]-5-(1-thioxopropylaminomethyl)-1,3-oxazolan-2-one or its salts;
(5S)-3-[4-(2-oxo-1,3-oxazolan-3-yl)phenyl]-5-(1-thioxoethylaminomethyl)-1,3-oxazolan-2-one or its salts;
(5S)-3-[3-fluoro-4-(3-methyl-4-oxo-1-imidazolidinyl)phenyl]-5-(1-thioxoethylaminomethyl)-1,3-oxazolan-2-one or its salts;

(5S)-3-[3-fluoro-4-(3-phenyl-2-oxo-1-imidazolidinyl)
  phenyl]-5-(1-thioxoethylaminomethyl)-1,3-oxazolan-
  2-one or its salts;
N1-{(5S)-3-[3-fluoro-4-(2-oxo-1,3-oxazolan-3-yl)phe-
  nyl]-2-oxo-1,3-oxazolan-5-ylmethyl}methylcarbamate
  or its salts;
N1-{(5S)-2-oxo-3-[4-(2-oxo-1,3-oxazolan-3-yl)-3-trif-
  luoromethylphenyl]-1,3-oxazolan-5-
  ylmethyl}methylcarbamate or its salts;
N1-{(5S)-3-[3,5-difluoro-4-(2-oxo-1,3-oxazolan-3-yl)
  phenyl]oxo-1,3-oxazolan-5-
  ylmethyl}methylcarbamate or its salts;
N1-{(5S)-3-[4-(2-oxo-1,3-oxazolan-3-yl)phenyl]-2-oxo-
  1,3-oxazolan-5-ylmethyl}methylcarbamate or its salts;
N1-{(5S)-3-[3-fluoro-4-(3-methyl-4-oxo-1-imidazolidi-
  nyl)phenyl]-2-oxo-1,3-oxazolan-5-
  ylmethyl}methylcarbamate or its salts;
(5S)-5-methylthioxy(thioxo)methylaminomethyl-3-[4-(2-
  oxo-1,3-oxazolan-3-yl)phenyl]-1,3-oxazolan-2-one or
  its salts;
N1-{(5S)-3-[3,5-difluoro-4-(2-oxo-1,3-oxazolan-3-yl)
  phenyl]-2-oxo-1,3-oxazolan-5-
  ylmethyl}methyldithiocarbamate or its salts;
N1-{(5S)-3-[3-fluoro-4-(2-oxo-1,3-oxazolan-3-yl)phe-
  nyl]-2-oxo-1,3-oxazolan-5-
  ylmethyl}methylthiocarbamate or its salts;
N1-{(5S)-3-[3-fluoro-4-(2-oxo-1,3-oxazolan-3-yl)phe-
  nyl]-2-oxo-1,3-oxazolan-5-
  ylmethyl}ethylthiocarbamate or its salts;
N1-{(5S)-3-[3-fluoro-4-(2-oxo-1,3-oxazolan-3-yl)phe-
  nyl]-2-oxo-1,3-oxazolan-5-
  ylmethyl}trifluoroacetoxythiocarbamate or its salts;
(5S)-5-cyclohexyloxy(thioxo)methylaminomethyl-3-[4-
  (2-oxo-1,3-oxazolan-3-yl)phenyl]-1,3-oxazolan-2-one
  or its salts;
N1-{(5S)-3-[3-fluoro-4-(2-thioxo-1,3-oxazolan-3-yl)phe-
  nyl]-2-oxo-1,3-oxazolan-5-
  ylmethyl}methylthiocarbamate or its salts;
N1-{(5S)-3-[3-fluoro-4-(3-methyl-2-thioxo-1-imidazo-
  lidinyl)phenyl]-2-oxo-1,3-oxazolan-5-
  ylmethyl}ethylthiocarbamate or its salts;
N1-{(5S)-3-[3-fluoro-4-(3-methyl-2-thioxo-1-imidazo-
  lidinyl)phenyl]-2-oxo-1,3-oxazolan-5-ylmethyl}-1-
  propylthiocarbamate or its salts;
N1-{(5S)-3-[3-fluoro-4-(3-methyl-2-thioxo-1-imidazo-
  lidinyl)phenyl]-2-oxo-1,3-oxazolan-5-
  ylmethyl}methylthiocarbamate or its salts;
N1-{(5S)-3-[3-fluoro-4-(3-methyl-2-thioxo-1-imidazo-
  lidinyl)phenyl]-2-oxo-1,3-oxazolan-5-ylmethyl}-2-
  propylthiocarbamate or its salts;
N1-{(5S)-2-oxo-3-[4-(2-oxo-1,3-oxazolan-3-yl)-3-trif-
  luoromethylphenyl]-1,3-oxazolan-5-
  ylmethyl}methylthiocarbamate or its salts;
N1-{(5S)-2-oxo-3-[4-(2-oxo-1,3-oxazolan-3-yl)-3-trif-
  luoromethylphenyl]-1,3-oxazolan-5-
  ylmethyl}ethylthiocarbamate or its salts;
N1-{(5S)-3-[3,5-difluoro-4-(2-oxo-1,3-oxazolan-3-yl)
  phenyl]-2-oxo-1,3-oxazolan-5-
  ylmethyl}methylthiocarbamate or its salts;
N1-{(5S)-3-[4-(2-oxo-1,3-oxazolan-3-yl)phenyl]-2-oxo-
  1,3-oxazolan-5-ylmethyl}methylthiocarbamate or its
  salts;
N1-{(5S)-3-[4-(2-oxo-1,3-oxazolan-3-yl)phenyl]-2-oxo-
  1,3-oxazolan-5-ylmethyl}ethylthiocarbamate or its
  salts;
N1-{(5S)-3-[4-(2-oxo-1,3-oxazolan-3-yl)phenyl]-2-oxo-
  1,3-oxazolan-5-ylmethyl}-1-propylthiocarbamate or
  its salts;
(5S)-5-[2,2,2-trifluoroethyloxy(thioxo)methylaminom-
  ethyl]-3-[4-(2-oxo-1,3-oxazolan-3-yl)phenyl]-1,3-ox-
  azolan-2-one or its salts;
(5S)-5-[2-hydroxyethyloxy (thioxo)methylaminom-
  ethyl]-3-[4-(2-oxo-1,3-oxazolan-3-yl)phenyl]-1,3-ox-
  azolan-2-one or its salts;
(5S)-5-[2-methoxyethyloxy(thioxo)methylaminomethyl]-
  3-[4-(2-oxo-1,3-oxazolan-3-yl)phenyl]-1,3-oxazolan-
  2-one or its salts;
N1-{(5S)-3-[4-(2-oxo-1,3-oxazolan-3-yl)phenyl]-2-oxo-
  1,3-oxazolan-5-ylmethyl}allylthiocarbamate or its
  salts;
N1-{(5S)-3-[4-(2-oxo-1,3-oxazolan-3-yl)phenyl]-2-oxo-
  1,3-oxazolan-5-ylmethyl}-2-propylthiocarbamate or
  its salts;
N1-{(5S)-2-oxo-3-[4-(2-oxo-2,3-dihydrobenzo[d][1,3]
  oxazol-3-yl)phenyl]-1,3-oxazolan-5-
  ylmethyl}methylthiocarbamate or its salts;
N1-{(5S)-2-oxo-3-[4-(2-oxo-2,3-dihydrobenzo[d][1,3]
  oxazol-3-yl)phenyl]-1,3-oxazolan-5-
  ylmethyl}ethylthiocarbamate or its salts;
N1-{(5S)-3-[3-fluoro-4-(3-methyl-4-oxo-1-imidazolidi-
  nyl)phenyl]-2-oxo-1,3-oxazolan-5-
  ylmethyl}methylthiocarbamate or its salts;
N1-{(5S)-3-[4-(3-methyl-2-oxo-1-imidazolidinyl)phe-
  nyl]-2-oxo-1,3-oxazolan-5-
  ylmethyl}methylthiocarbamate or its salts;
N1-{(5S)-3-[4-(3-methyl-4-oxo-1-imidazolidinyl)phe-
  nyl]-2-oxo-1,3-oxazolan-5-
  ylmethyl}methylthiocarbamate or its salts;
N1-{(5S)-3-[3-fluoro-4-(3-methyl-2-oxo-1-imidazolidi-
  nyl)phenyl]-2-oxo-1,3-oxazolan-5-
  ylmethyl}methylthiocarbamate or its salts;
N1-{(5S)-3-[4-(3-benzyl-2-oxo-1-imidazolidinyl)phe-
  nyl]-2-oxo-1,3-oxazolan-5-
  ylmethyl}methylthiocarbamate or its salts;
N1-{(5S)-3-[4-(3-benzyl-2-oxo-1-imidazolidinyl)phe-
  nyl]-2-oxo-1,3-oxazolan-5-
  ylmethyl}ethylthiocarbamate or its salts;
N1-{(5S)-3-[3-fluoro-4-(3-phenyl-2-oxo-1-imidazolidi-
  nyl)phenyl]-2-oxo-1,3-oxazolan-5-
  ylmethyl}methylthiocarbamate or its salts;
N1-{(5S)-3-[3-fluoro-4-(3-phenyl-2-oxo-1-imidazolidi-
  nyl)phenyl]-2-oxo-1,3-oxazolan-5-
  ylmethyl}ethylthiocarbamate or its salts;
N1-((5S)-3-{3-fluoro-4-[3-(4-fluorophenyl)-2-oxo-1-
  imidazolidinyl]phenyl}-2-oxo-1,3-oxazolan-5-ylm-
  ethyl)methylthiocarbamate or its salts;
N1-((5S)-3-{3-fluoro-4-[3-(4-fluorophenyl)-2-oxo-1-
  imidazolidinyl]phenyl}-2-oxo-1,3-oxazolan-5-ylm-
  ethyl)ethylthiocarbamate or its salts;
N1-((5S)-3-{3-fluoro-4-[3-(4-fluorophenyl)-2-oxo-1-
  imidazolidinyl]phenyl}-2-oxo-1,3-oxazolan-5-ylm-
  ethyl)-2-propylthiocarbamate or its salts;
N1-((5S)-3-{3-fluoro-4-[3-methoxymethyl-4-oxo-1-imi-
  dazolidinyl]phenyl}-2-oxo-1,3-oxazolan-5-ylmethyl)
  methylthiocarbamate or its salts;
N1-((5S)-3-{3-fluoro-4-[3-benzyl-4-oxo-1-imidazolidi-
  nyl]phenyl}-2-oxo-1,3-oxazolan-5-ylmethyl)methylth-
  iocarbamate or its salts;
N1-((5S)-3-{3-fluoro-4-[3-benzyl-4-oxo-1-imidazolidi-
  nyl]phenyl}-2-oxo-1,3-oxazolan-5-ylmethyl)ethylthio-
  carbamate or its salts;

N1-((5S)-3-{4-[2-oxo-1,3-oxazolan-3yl]phenyl}-2-oxo-1,3-oxazolan-5-ylmethyl)-(N,N-dimethylamino)ethylthiocarbamate or its salts;

N1-((5S)-3-{3-fluoro-4-[3-(4-methoxybenzyl)-4-oxo-1-imidazolidinyl]phenyl}-2-oxo-1,3-oxazolan-5-ylmethyl)methylthiocarbamate or its salts;

N1-((5S)-3-{3-fluoro-4-[3-benzyl-4-oxo-1-imidazolidinyl]phenyl}-2-oxo-1,3-oxazolan-5-ylmethyl)isopropylthiocarbamate or its salts;

N1-((5S)-3-{3-fluoro-4-[3-hydroxymethyl-4-oxo-1-imidazolidinyl]phenyl}-2-oxo-1,3-oxazolan-5-ylmethyl)methylthiocarbamate or its salts;

N1-((5S)-3-{3-fluoro-4-[4-oxo-1-imidazolidinyl]phenyl}-2-oxo-1,3-oxazolan-5-ylmethyl)methylthiocarbamate or its salts;

N1-{(5S)-3-[3-fluoro-4-(3-methyl-4-thioxo-1-imidazolidinyl)phenyl]-2-oxo-1,3-oxazolan-5-ylmethyl}methylthiocarbamate or its salts;

(5S)-5-[(2S)-2-hydroxymethylazolan-1-yl(thioxo)methylaminomethyl]-3-[4-(2-oxo-1,3-oxazolan-3-yl)phenyl]-1,3-oxazolan-2-one or its salts;

(5S)-5-diethylamino(thioxo)methylaminomethyl-3-[4-(2-oxo-1,3-oxazolan-3-yl)phenyl]-1,3-oxazolan-2-one or its salts;

(5S)-5-allylamino(thioxo)methylaminomethyl-3-[4-(2-oxo-1,3-oxazolan-3-yl)phenyl]-1,3-oxazolan-2-one or its salts;

(5S)-5-benzylamino(thioxo)methylaminomethyl-3-[4-(2-oxo-1,3-oxazolan-3-yl)phenyl]-1,3-oxazolan-2-one or its salts;

(5S)-5-[4-methoxybenzylamino(thioxo)methylaminomethyl]-3-[4-(2-oxo-1,3-oxazolan-3-yl)phenyl]-1,3-oxazolan-2-one or its salts;

(5S)-3-[4-(2-oxo-1,3-oxazolan-3-yl)phenyl]-5-[2-pyridylmethylamino(thioxo)methylaminomethyl]-1,3-oxazolan-2-one or its salts;

(5S)-5-methylamino(thioxo)methylaminomethyl-3-[4-(2-oxo-1,3-oxazolan-3-yl)phenyl]-1,3-oxazolan-2-one or its salts;

(5S)-5-[2-hydroxyethylamino(thioxo)methylaminomethyl]-3-[4-(2-oxo-1,3-oxazolan-3-yl)phenyl]-1,3-oxazolan-2-one or its salts;

(5S)-3-[4-(2-oxo-1,3-oxazolan-3-yl)phenyl]-5-[1,4-thiazinan-4-yl(thioxo)methylaminomethyl]-1,3-oxazolan-2-one or its salts;

(5S)-3-[4-(2-oxo-1,3-oxazolan-3-yl)phenyl]-5-[2-pyridylamino(thioxo)methylaminomethyl]-1,3-oxazolan-2-one or its salts;

(5S)-5-amino(thioxo)methylaminomethyl-3-[3-fluoro-4-(2-oxo-1,3-oxazolan-3-yl)phenyl]-1,3-oxazolan-2-one or its salts;

(5S)-3-[3-fluoro-4-(2-oxo-1,3-oxazolan-3-yl)phenyl]-5-methylamino(thioxo)methylamino methyl-1,3-oxazolan-2-one or its salts;

(5S)-5-amino(thioxo)methylaminomethyl-3-[3,5-difluoro-4-(2-oxo-1,3-oxazolan-3-yl)phenyl]-1,3-oxazolan-2-one or its salts;

(5S)-3-[3,5-difluoro-4-(2-oxo-1,3-oxazolan-3-yl)phenyl]-5-methylamino(thioxo)methylaminomethyl-1,3-oxazolan-2-one or its salts and N1-((5S)-3-{4-[2-oxo-1,3-oxazolan-3yl]phenyl}-2-oxo-1,3-oxazolan-5-ylmethyl)-(N,N-dimethylamino)ethylthiocarbamate hydrochloride.

The present invention also relates to a process for the preparation of the compound of formula (I) where $R^1$ represents $NHR^4$, wherein $R^4$ represents hydrogen atom and all other symbols are as defined earlier, which comprises:

(i) reacting a compound of formula (III)

where all the symbols are as defined earlier, with a compound of formula (IV)

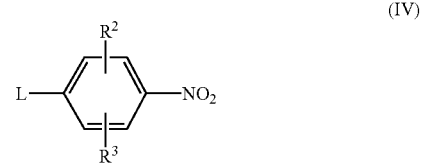

where L represents a leaving group such as halogen atom, alkoxy, sulfonyl groups and the like; $R^2$ and $R^3$ are as defined earlier, to produce a compound of formula (V)

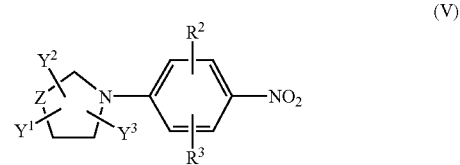

where $Y^1$, $Y^2$, $Y^3$, $R^2$, $R^3$ and Z are as defined earlier, (ii) reducing the compound of formula (V) to produce a compound of formula (VI)

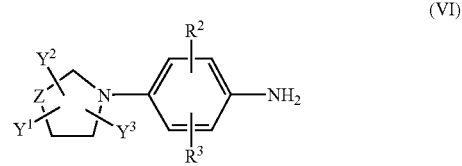

where $Y^1$, $Y^2$, $Y^3$, $R^2$, $R^3$ and Z are as defined earlier, (iii) reacting the compound of formula (VI) with alkylchloroformate, to produce a compound of formula (VII)

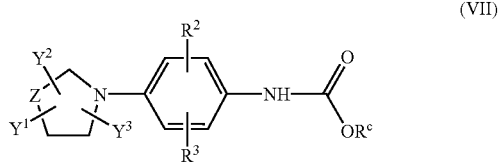

where $R^c$ represents $(C_1-C_8)$alkyl group such as methyl, ethyl, propyl, benzyl, allyl group and the like; $Y^1$, $Y^2$, $Y^3$, $R^2$, $R^3$ and Z are as defined earlier, (iv) reacting the compound of formula (VII) with a compound of formula (VIII)

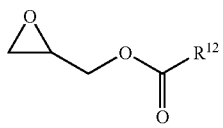

(VIII)

where $R^{12}$ represents a $(C_1-C_3)$alkyl group such as methyl, ethyl or propyl in the presence of a base to produce a compound of formula (I)

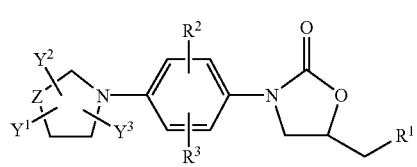

(I)

where $R^1$ represents hydroxy; $Y^1$, $Y^2$, $Y^3$, $R^2$, $R^3$ and Z are as defined earlier, (v) reacting the compound of formula (I) with alkylsulfonyl chloride or aryl sulfonyl chloride to produce a compound of formula (I), where $R^1$ represents alkyl sulfonyl or aryl sulfonyl, which in turn was reacted with $NaN_3$ to produce compound of formula (I)

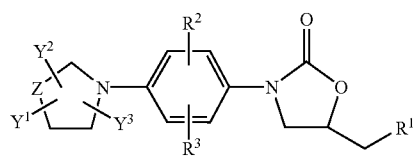

(I)

where $R^1$ represents azido; $Y^1$, $Y^2$, $Y^3$, $R^2$, $R^3$ and Z are as defined earlier and (vi) reducing the compound of formula (I) wherein $R^1$ represents azido group, to produce compound of formula (I)

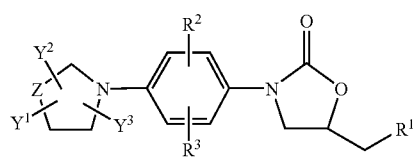

(I)

where $R^1$ represents $NHR^4$ wherein $R^4$ represents hydrogen atom; $Y^1$, $Y^2$, $Y^3$, $R^2$, $R^3$ and Z are as defined earlier.

The reaction of a compound of formula (III) with a compound of formula (IV) to produce a compound of formula (V) may be carried out using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform and the like or mixtures thereof. The reaction may be carried out in inert atmosphere, which may be maintained using inert gases such as $N_2$ or Ar. The reaction may be carried out at a temperature in the range of 20° C.–100° C., preferably at a temperature in the range of ambient –80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature in the range of 25 to 60° C., preferably at room temperature. The reaction time ranges from 2 to 48 h. The reduction may also be carried out by employing metal in mineral acids such Sn/HCl, Fe/HCl, Zn/HCl, $Zn/CH_3CO_2H$ and the like.

The conversion of compound of formula (VI) to compound of formula (VII) may be carried out with alkylchloroformates such as methychloroformate, ethylchloroformate, propylchloroformate, benzylchloroformate and the like. The solvent of the reaction may be selected from water, acetone, tetrahydrofuran (THF), acetonitrile, dichloromethane (DCM) and the like or mixtures thereof. The reaction may be carried out in the presence of base such as $K_2CO_3$, $Na_2CO_3$, NaH, KOH, triethylamine and the like. The temperature of the reaction may be carried out in the presence of 0 to 60° C., preferably at 0° C. to room temperature. The time of the reaction is maintained in the range of 1–12 h, preferably in the range of 1–4 h.

The reaction of a compound of formula (VII) with a compound of formula (VIII) to produce a compound of formula (I), where $R^1$ represents hydroxy group, defined above may be carried out in the presence of a base such as alkali metal hydrides like NaH or KH or organolithiums like $CH_3Li$, BuLi, LDA and the like or alkoxides such as NaOMe, NaOEt, t-BuOK. The reaction may be carried out in the presence of a solvent such as THF, dioxane, DMF, DMSO, DME and the like or mixtures thereof. Hexamethylphosphamide (HMPA) may be used as a cosolvent. The reaction temperature may range from –78 to 150° C., preferably at a temperature in the range of –78 to 30° C. The duration of the reaction may range from 3 to 12 h.

The compound of formula (I) where $R^1$ represents OH is converted to compound of formula (I) where $R^1$ represents alkylsulfonyl or arylsulfonyl by treating with alkylsulfonylchloride or arylsulfonylchloride such as methanesulfonyl chloride, p-toluenesulfonyl chloride and the like. The reaction may be carried out in the presence of chloroform, dichloromethane, THF, dioxane and the like or mixtures thereof. The base used in the reaction may be selected from $Et_3N$, diisopropyl ethylamine, $Na_2CO_3$, $K_2CO_3$ and the like. The temperature of the reaction is maintained in the range of 0 to 50° C., preferably in the range of 0 to room temperature. The time of the reaction should be maintained in the range of 1–12 h, preferably in the range of 1–4 h. The compound of formula (I) where $R^1$ represents alkylsulfonyl or arylsulfonyl is converted to compound of formula (I) where $R^1$ represents azido group, by treating with $NaN_3$. The solvent used in the reaction may be selected from dimethylformamide (DMF), dimethyl sulfoxide (DMSO), methylcyanide and the like. The temperature of the reaction is maintained in the range of room temperature to 120° C., preferably room temperature to 80° C. The time of the reaction is maintained in the range of 1–12 h, preferably 1–4 h.

The reduction of a compound of formula (I) where $R^1$ represents azido group, to produce a compound of formula (I) where $R^1$ represents $NHR^4$ wherein $R^4$ represents hydrogen atom, may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature in the range of 25 to 60° C., preferably at room temperature. The reaction time ranges from 2 to 48 h. The reduction may also be carried out by employing $PPh_3$ in water.

In still another embodiment of the present invention there is provided another process for the preparation of compound of formula (I) where $R^1$ represents hydroxy and all the symbols are as defined earlier, which comprises:

(i) reacting the compound of formula (VI)

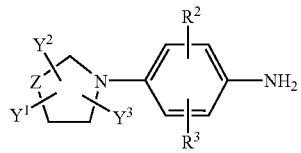

where all the symbols are as defined earlier, with a compound of formula (IX)

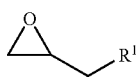

where $R^1$ represents hydroxy, to produce a compound of formula (X)

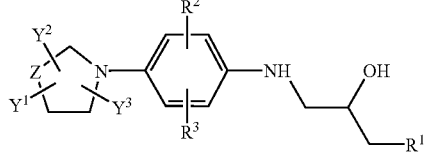

where $R^1$ represents hydroxy; $Y^1$, $Y^2$, $Y^3$, $R^2$, $R^3$ and Z are as defined earlier, and (ii) carbonylating the compound of formula (X) with a suitable carbonylating agent to produce the compound of formula (I) where $R^1$ represents hydroxy and all other symbols are as defined above.

The reaction of a compound of formula (VI) defined above with a compound of formula (IX) defined above to produce a compound of formula (X) may be carried out in the presence or absence of a base such as $K_2CO_3$, NaH, t-BuOK and the like or mixtures thereof. The reaction may be carried out in the presence of a solvent such as DMF, toluene, THF, $CH_3CN$, and the like or mixtures thereof. The reaction may also be carried out in the presence of Lewis acids such as $BF_3.OEt_2$, $ZnCl_2$, $Ti(OiPr)_4$, lanthanide metal complexes and the like in the presence of DCE, DMF, THF and the like or mixtures thereof. The reaction temperature may be in the range of 0 to 120° C., preferably at a temperature in the range of 0 to 100° C. The reaction time may range from 3 to 24 h, preferably from 4 to 12 h.

The conversion of compound of formula (X) to a compound of formula (I) may be carried out using a carbonylating agent such as dialkyl carbonate, dihalo carbonyl, 1,1'-carbonyldiimidazole and the like in the presence or absence of a base. The base may be selected from triethylamine, tributylamine, diisopropylethylamine, 1,4-diazabicyclo(2.2.2)octane (DABCO), 1,8-diazabicyclo(5.4.0)undec-7-ene (DBU), 1,1,5-diazabicyclo(4.3.0)non-5-ene (DBN), alkoxides like NaOMe, NaOEt and the like or the inorganic bases such as NaOH, KOH and the like. The reaction may be carried out in the presence of solvents such as dichloromethane, THF, DMF, ethyl acetate and the like or mixtures thereof. The reaction temperature may be in the range of −20 to 135° C., preferably at a temperature in the range of 15 to 80° C. The reaction time may range from 2 to 72 h, preferably from 2 to 50 h.

In still another embodiment of the present invention there is provided yet another process for the preparation of compound of the formula (I) where $R^1$ represents azido and all other symbols are as defined earlier, which comprises:

(i) reacting a compound of formula (VII)

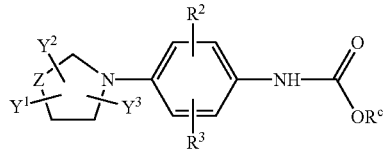

where $R^c$ represents $(C_1–C_8)$alkyl group such as methyl, ethyl, propyl, benzyl, allyl group and the like; and all other symbols are as defined earlier, with a compound of formula (XI)

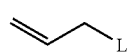

where L represents a leaving group such as halogen atom, alkoxy, sulfonyl groups and the like; to produce a compound of formula (XII)

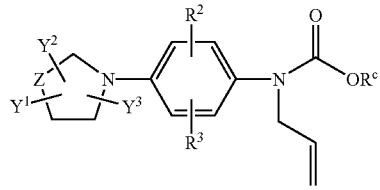

where $R^c$, $Y^1$, $Y^2$, $Y^3$, $R^2$, $R^3$ and Z are as defined earlier, (ii) converting the compound of formula (XII) defined above to a compound of formula (XIII)

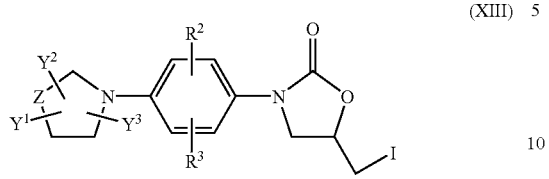

where $Y^1$, $Y^2$, $Y^3$, $R^2$, $R^3$ and Z are as defined earlier, and (iii) converting the compound of formula (XIII) defined above to a compound of formula (I) by reacting with organic or inorganic azide,

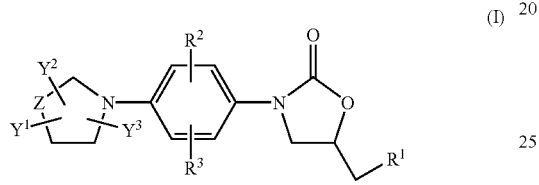

where $R^1$ represents azido group; $Y^1$, $Y^2$, $Y^3$, $R^2$, $R^3$ and Z are as defined earlier.

The reaction of a compound of formula (VII) with a compound of formula (XI) may be carried out in the presence of base such as NaH, KH, $K_2CO_3$, t-BuOK, LDA, NaOMe, with or without phase transfer catalyst such as tetrabutylammonium halide and the like. The reaction may be carried out in the presence of a suitable solvent such as THF, DMF, DMSO, benzene and the like or mixtures thereof. The reaction may be carried out at a temperature in the range of −78 to 120° C., preferably at −78 to 60° C. The reaction time may range from 2 to 20 h, preferably from 4 to 10 h.

The conversion of a compound of formula (XII) to a compound of formula (XIII) defined above may be carried in the presence of reagents such as $I_2$, KI, or NaI. The reaction may be carried out in the presence of solvent such as $CHCl_3$, $CH_2Cl_2$, THF, DMF, DMSO, acetonitrile and the like or mixtures thereof. The reaction temperature may be in the range of 0 to 100° C., preferably at ambient temperature. The reaction time may range from 2 to 24 h, preferably from 2 to 12 h.

The conversion of a compound of formula (XIII) to a compound of formula (I) where $R^1$ represents azido group, may be carried out in the presence of one or more equivalents of metal azide such as $LiN_3$, $NaN_3$ or trialkyl silylazide. The reaction may be carried out in the presence of solvent such as THF, acetone, DMF, DMSO and the like or mixtures thereof. The reaction may be carried out in inert atmosphere, which may be maintained using $N_2$ or Ar. The reaction may be carried out at a temperature in the range of ambient temperature to reflux temperature of the solvent, preferably at a temperature in the range of 50 to 80° C. The reaction time may range from 0.5 to 18 h, preferably 1 to 4 h.

In yet another embodiment of the present invention, there is provided a process for the preparation of compound of formula (I), where $R^1$ represents hydroxy group and all other symbols are as defined earlier, which comprises:

(i) reacting a compound of formula (VII)

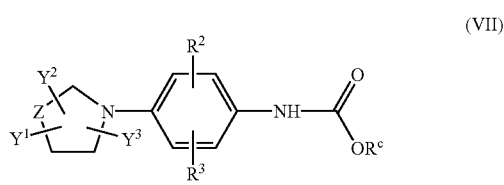

where all the symbols are as defined earlier, with a compound of formula (XIV)

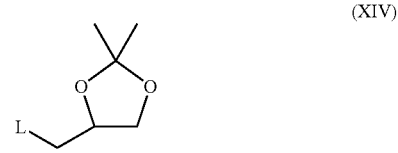

where L represents a leaving group such as halogen atom, alkoxy, sulfonyl groups and the like; to produce a compound of formula (XV)

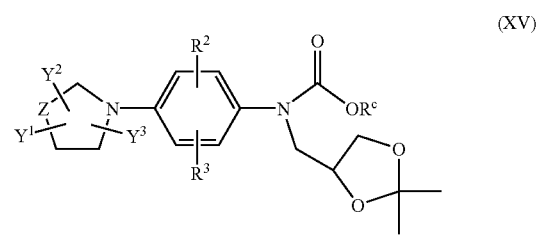

where $R^c$, $Y^1$, $Y^2$, $Y^3$, $R^2$, $R^3$ and Z are as defined earlier, (ii) hydrolysing the acetonide moiety in the compound of formula (XV) using conventional methods to produce a compound of formula (XVI)

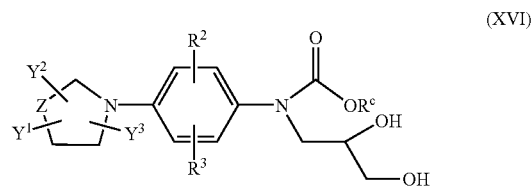

where $R^c$, $Y^1$, $Y^2$, $Y^3$, $R^2$, $R^3$ and Z are as defined earlier, and (iii) cyclising the compound of formula (XVI) with or without a base to a compound of formula (I)

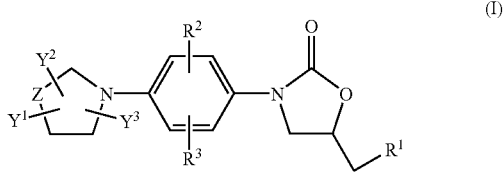

where $R^1$ represents hydroxy group and all other symbols are as defined earlier.

The reaction of a compound of formula (VII) with a compound of formula (XIV) to produce a compound of formula (XV) may be carried out in the presence of a base. The base employed may be selected from $K_2CO_3$, NaH, t-BuOK, LDA and the like. The reaction may be carried out in the presence of a solvent such as DMF, THF, DMSO, EtOH and the like. The reaction may be carried at a temperature in the range of −78 to 120° C., preferably at a temperature in the range of −78 to 1 00° C. The reaction time may range from 2 to 24 h, preferably from 2 to 20 h.

The hydrolysis of a compound of formula (XV) to produce a compound of formula (XVI) may be carried out using dilute mineral acid such as HCl, $H_2SO_4$ and the like, organic acids such as aqueous acetic acid, p-toluene sulfonic acid, camphorsulfonic acid, trifluoro acetic acid and the like. The reaction may be carried out in the presence of suitable solvent such as water, methanol, THF, dioxane and the like or mixtures thereof. The reaction may be carried at a temperature in the range of 30 to 100° C., preferably at a temperature in the range of 30 to 60° C. The reaction time may range from 10 min to 5 h, preferably from 30 min to 2.5 h.

The conversion of a compound of formula (XVI) to a compound of formula (I) where R represents hydroxy group, may be carried out by using a base such as NaOMe, $K_2CO_3$, NaH and the like, in presence of a solvent such as MeOH, DMF, THF, and the like. The duration and temperature of the reaction are maintained in the range of 2 to 4 h and room temperature to 150° C. respectively.

In still another embodiment of the present invention there is provided a process for the preparation of compounds of formula (I) where $R^1$ represents azido group and all other symbols are as defined earlier, which comprises:

(i) reacting a compound of formula (VII)

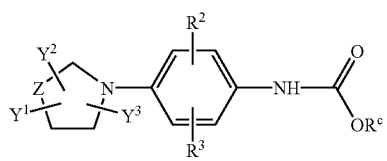

(VII)

where all the symbols are as defined earlier, with a compound of formula (XVII)

(XVII)

where L represents a leaving group such as halogen atom, alkoxy, sulfonyl groups and the like; to produce a compound of formula (XVIII)

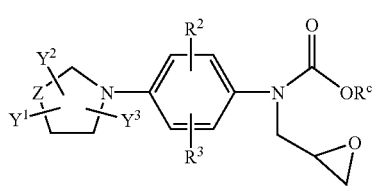

(XVIII)

where $R^c$, $Y^1$, $Y^2$, $Y^3$, $R^2$, $R^3$ and Z are as defined earlier, and (ii) converting the compound of formula (XVIII) defined above to a compound of formula (I) by reacting with an organic or an inorganic azide,

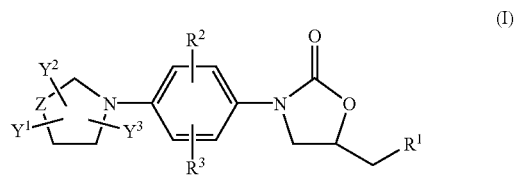

(I)

where $R^1$ represents azido group; $Y^1$, $Y^2$, $Y^3$, $R^2$, $R^3$ and Z are as defined earlier, The reaction of a compound of formula (VII) defined above with a compound of formula (XVII) defined above may be carried out in the presence of a base such as NaH, NaOMe, $K_2CO_3$, n-BuLi, LDA and the like. The reaction may be carried out in the presence of a solvent such as DMF, THF, DMSO, benzene and the like or mixtures thereof. The reaction may be carried out at a temperature in the range of −78 to 70° C. preferably at a temperature in the range of −78 to 50° C. The reaction time may range from 1 to 15 h preferably 1 to 10 h.

The conversion of a compound of formula (XVIII) to a compound of formula (I) where $R^1$ represents azido group, may be carried out in the presence of one or more equivalent of metal azide such as $LiN_3$, $NaN_3$ or trialkyl silylazide. The reaction may be carried out in the presence of solvent such as THF, acetone, DMF, DMSO and the like or mixtures thereof. The reaction may be carried out in inert atmosphere, which may be maintained by using $N_2$ or Ar. The reaction may be carried out at a temperature in the range of ambient temperature to reflux temperature of the solvent, preferably at a temperature in the range of 50 to 80° C. The reaction time may range from 0.5 to 18 h, preferably 1 to 4 h.

In still another embodiment of the present invention there is provided yet another process for the preparation of compound of the formula (I), where $R^1$ represents $NHR^4$, wherein $R^4$ represents acetyl group and all other symbols are as defined earlier, which comprises:

(i) reacting a compound of formula (VII)

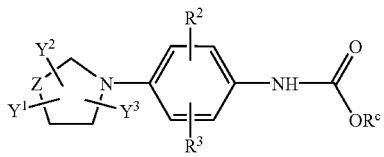

(VII)

where all the symbols are as defined earlier, with a compound of formula (XIX)

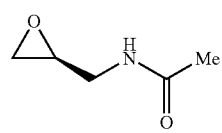

(XIX)

to produce a compound of formula (I)

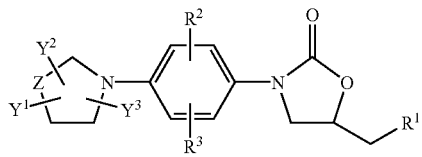

where $R^1$ represents $NHR^4$, where $R^4$ represents acetyl group; and $Y^1$, $Y^2$, $Y^3$, $R^2$, $R^3$ and Z are as defined earlier.

The compound of formula (VII) defined above may be converted to a compound of formula (I) defined above, by reacting with compound of formula (XIX) in presence of a base such as NaH, LDA, BuLi and the like. The reaction may be carried out at a temperature in the range of −78 to 100° C., preferably in the range of −78 to 80° C. The reaction time may range from 3 to 10 h.

In yet another embodiment of the present invention there is provided a process for the preparation of compound of formula (I), where $R^1$ represents $NHR^4$, wherein $R^4$ represents formyl group; from compound of formula (I) where $R^1$ represents $NHR^4$ wherein $R^4$ represents hydrogen atom,

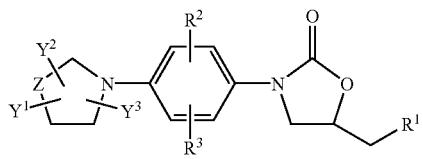

where all other symbols are as defined earlier.

The reaction of compound of formula (I) where $R^1$ represents $NHR^4$ wherein $R^4$ represents hydrogen atom, to produce a compound of formula (I), where $R^1$ represents $NHR^4$, wherein $R^4$ represents formyl group, may be carried out in presence of alkyl formates such as methyl formate, ethyl formate and the like. The duration of the reaction may range from 4 to 48 h, prefereably 12 to 24 h. The reaction may be carried out at a temperature in the range of 60 to 120° C., preferably at reflux temperature.

In another embodiment of the present invention there is provided a process for the preparation of compound of formula (I), where $R^1$ represents $NHR^4$, wherein $R^4$ represents $-C(=O)-R^{4a}$, where $R^{4a}$ represents $(C_1-C_6)$alkyl, $(C_1-C_6)$alkoxy, $(C_2-C_6)$alkenyl, halo$(C_1-C_6)$alkyl, aryloxy, $(C_2-C_6)$alkenyloxy, aryloxycarbonyl or $(C_1-C_6)$alkoxycarbonyl; from a compound of formula (I) where $R^1$ represents $NHR^4$ wherein $R^4$ represents hydrogen atom,

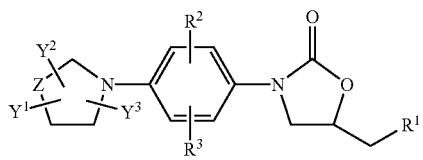

where all other symbols are as defined earlier.

The compound of formula (I), where $R^1$ represents $NHR^4$, wherein $R^4$ represents $-C(=O)-R^{4a}$, $R^{4a}$ represents $(C_1-C_6)$alkyl, $(C_1-C_6)$alkoxy, $(C_2-C_6)$alkenyl, halo$(C_1-C_6)$alkyl, aryloxy, $(C_2-C_6)$alkenyloxy, aryloxycarbonyl or $(C_1-C_6)$alkoxycarbonyl, may be prepared from compound of formula (I) where $R^1$ represents $NHR^4$ wherein $R^4$ represents hydrogen atom, by treating with appropriate halide such as acyl chloride like acetyl chloride, propionyl chloride and the like; alkylchloroformate like methylchloroformate, ethylchloroformate and the like; aralkylchloroformate like benzylchloroformate and the like. The reaction may be carried out in the presence of a solvent such as $CH_2Cl_2$, $CHCl_3$, toluene, THF and the like or mixtures thereof. The reaction may be carried out in the presence of a base like $Et_3N$, diisopropyl ethylamine, $K_2CO_3$, NaH, KOt-Bu and the like. The reaction may be carried at a temperature in the range of −20 to 60° C., preferably at a temperature in the range of 0 to room temperature. The reaction time may range from 1 to 12 h, preferably from 1 to 4 h.

Alternatively, the compound of formula (I), where $R^1$ represents $NHR^4$ wherein $R^4$ represents acetyl group, may be prepared by reacting compound of formula (I) where $R^1$ represents azido group, by treating with thioacetic acid.

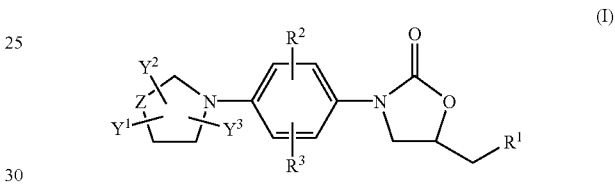

The compound of formula (I) where $R^1$ represents azido group may be converted to a compound of formula (I) where $R^1$ represents $NHR^4$ wherein $R^4$ represents acetyl group by using thioacetic acid, with or without using a solvent such as THF, DMF, toluene and the like. The reaction may be carried out at a temperature in the range of 25 to 40° C., preferably at room temperature. The reaction may range from 3 to 24 h, preferably from 4 to 12 h.

In another embodiment of the present invention there is provided a process for the preparation of compound of formula (I), where $R^1$ represents $NHR^4$, wherein $R^4$ represents $-C(=S)-R^{4b}$, wherein $R^{4b}$ represents $(C_1-C_6)$alkyl, halo$(C_1-C_6)$alkyl, $-C(=O)-(C_1-C_6)$alkoxy, $-C(=O)$-aryloxy, $-C(=S)-(C_1-C_6)$alkyl or $-C(=S)$-aryl; from compound of formula (I), where $R^1$ represents $NHR^4$, wherein $R^4$ represents $-C(=O)-R^{4b}$, wherein $R^{4b}$ represents $(C_1-C_6)$alkyl, halo$(C_1-C_6)$alkyl, $C(=O)-(C_1-C_6)$alkoxy, $-C(=O)$-aryloxy, $-C(=S)-(C_1-C_6)$alkyl or $-C(=S)$-aryl.

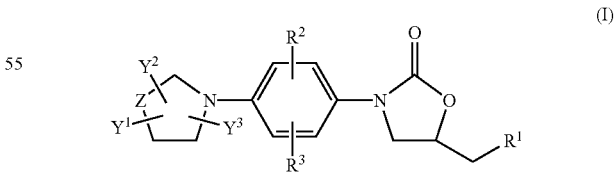

where all symbols are as defined earlier.

Conversion of compound of formula (I), where $R^1$ represents $NHR^4$, wherein $R^4$ represents $-C(=O)-R^{4b}$, wherein $R^{4b}$ represents $(C_1-C_6)$alkyl, halo$(C_1-C_6)$alkyl, $-C(=O)-(C_1-C_6)$alkoxy, $-C(=O)$-aryloxy, $-C(=S)-(C_1-C_6)$alkyl or $-C(=S)$-aryl; to a compound of formula (I), where $R^1$ represents $NHR^4$, wherein $R^4$ represents —C(=S)—$R^{4b}$, wherein $R^{4b}$ represents $(C_1-C_6)$alkyl, halo$(C_1-C_6)$alkyl, —C(=O)—$(C_1-C_6)$alkoxy, —C(=O)-aryloxy, —C(=S)—$(C_1-C_6)$alkyl or —C(=S)-aryl; may be carried out by taking a solution of the amide and Lawesson's reagent (2,4-bis(methoxyphenyl)-1,3-dithia-2,4-diphosphetane-2,4-disulfide) in dry dioxane, toluene, THF, DMF and the like. The reaction may be carried at a temperature in the range of room temperature to 130° C., preferably at a temperature in the range of 55 to 90° C. The reaction time may range from 3 to 24 h, preferably from 3 to 10 h.

In another embodiment of the present invention there is provided a process for the preparation of compound of formula (I), where $R^1$ represents $NHR^4$, wherein $R^4$ represents —C(=S)—$SR^{4c}$, wherein $R^{4c}$ represents $(C_1-C_6)$alkyl group; from compound of formula (I) where $R^1$ represents $NHR^4$ wherein $R^4$ represents hydrogen atom,

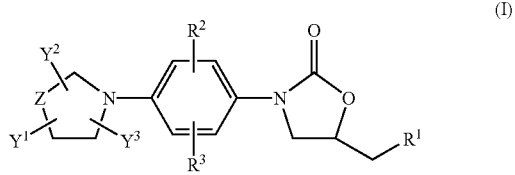

where all other symbols are as defined earlier.

The compound of formula (I), where $R^1$ represents $NHR^4$, wherein $R^4$ represents —C(=S)—$SR^{4c}$, wherein $R^{4c}$ represents $(C_1-C_6)$alkyl group, may be prepared from compound of formula (I) where $R^1$ represents $NHR^4$ wherein $R^4$ represents hydrogen atom, by using $CS_2$ in the presence of a base such as $Et_3N$, diisopropyl ethylamine, $K_2CO_3$, NaH, KOt-Bu and the like, followed by the appropriate alkylhalide such as methyliodide, ethylbromide, propylbromide and the like. The reaction may be carried out in the presence of a solvent such as water, ethanol, methanol, isopropanol, $CH_3CN$ and the like, or mixtures thereof. The reaction may be carried at a temperature in the range of room temperature to 60° C., preferably at room temperature. The reaction time may range from 6 to 24 h.

In another embodiment of the present invention there is provided a process for the preparation of compound of formula (I), where $R^1$ represents $NHR^4$, wherein $R^4$ represents —C(=S)—$OR^{4d}$, $R^{4d}$ represents $(C_1-C_6)$alkyl, cyclo$(C_3-C_6)$alkyl, —(C=O)—$(C_1-C_6)$alkyl group substituted with fluorine; aryl, halo$(C_1-C_6)$alkyl, hydroxy$(C_1-C_6)$alkyl, $(C_1-C_6)$alkoxy$(C_1-C_6)$alkyl or $(C_2-C_6)$ alkenyl, which comprises:

(i) converting the compound of formula (I) where $R^1$ represents $NHR^4$ wherein $R^4$ represents hydrogen atom, to a compound of formula (I) where $R^1$ represents isothiocyanate group,

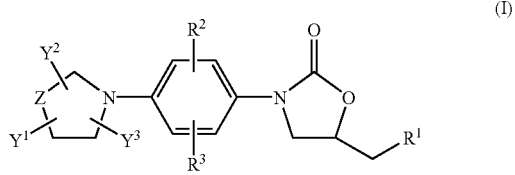

where all other symbols are as defined earlier, (ii) converting the compound of formula (I) where $R^1$ represents isothiocyanate group, to a compound of formula (I) where $R^1$ represents $NHR^4$, wherein $R^4$ represents —C(S)—$OR^{4d}$, wherein $R^{4d}$ represents $(C_1-C_6)$alkyl, cyclo$(C_3-C_6)$alkyl, —(C=O)—$(C_1-C_6)$alkyl group substituted with fluorine; aryl, halo$(C_1-C_6)$alkyl, hydroxy$(C_1-C_6)$alkyl, $(C_1-C_6)$alkoxy$(C_1-C_6)$alkyl or $(C_2-C_6)$alkenyl group and all other symbols are as defined earlier.

The compound of formula (I) where $R^1$ represents isothiocyanate group, may be prepared from compound of formula (I) where $R^1$ represents $NHR^4$ wherein $R^4$ represents hydrogen atom, by using thiophosgene, in the presence of a base such as $Et_3N$, $K_2CO_3$, NaOH and the like. The reaction may be carried out in the presence of a solvent such as ethanol, methanol, isopropanol, $CH_2Cl_2$, $CH_3CN$ and the like. The reaction may be carried at a temperature in the range of 0 to 60° C., preferably at 0° C. The reaction may be carried out in an inert atmosphere using argon or any other inert gas. The reaction time may range from 3 to 24 h.

The compound of formula (I) where $R^1$ represents $NHR^4$, wherein $R^4$ represents —C(=S)$OR^{4d}$, wherein $R^{4d}$ represents $(C_1-C_6)$alkyl, cyclo$(C_3-C_6)$alkyl, —(C=O)—$(C_1-C_6)$alkyl group substituted with fluorine; aryl, halo$(C_1-C_6)$alkyl, hydroxy$(C_1-C_6)$alkyl, $(C_1-C_6)$alkoxy$(C_1-C_6)$alkyl or $(C_2-C_6)$alkenyl, is prepared from the compound of formula (I) where $R^1$ represents isothiocyanate group, by using an alcohol such as methanol, ethanol, propanol, cylcohexanol and the like, in the presence of a base such as NaH, KH and the like. The reaction may be carried out in the presence of a solvent such as THF, toluene, DMF and the like. The reaction may be carried at a temperature in the range of room temperature to 130° C., preferably at reflux temperature of the solvent used. The reaction time may range from 6 to 24 h.

In another embodiment of the present invention there is provided a process for the preparation of compound of formula (I), where $R^1$ represents $NHR^4$, wherein $R^4$ represents —C(=S)—N(R'R"), wherein R' represents hydrogen, $(C_1-C_6)$alkyl, $(C_2-C_6)$alkenyl, substituted or unsubstituted aralkyl, heteroaralkyl, hydroxy$(C_1-C_6)$alkyl, R" represents hydrogen or $(C_1-C_6)$alkyl or the two R' and R" groups together form a 5 or 6 membered cyclic structures containing one or two hetero atoms; from a compound of formula (I) where $R^1$ represents isothiocyanate group,

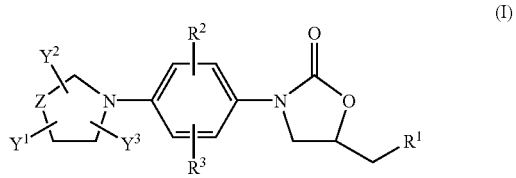

where all other symbols are as defined earlier.

The compound of formula (I), where $R^1$ represents $NHR^4$, wherein $R^4$ represents —C(=S)—N(R'R"), wherein R' and R" independently represent hydrogen, is prepared by passing ammonia gas into a solution of compound of formula (I) where $R^1$ represents isothiocyanate group, by using a solvent such as THF, toluene, and the like. The reaction may be carried at a temperature in the range of −10° C. to room temperature, preferably at −10° C. The reaction time may range from 20 min to 4 h, preferably 30 min.

The compound of formula (I), where R¹ represents NHR⁴, wherein R⁴ represents —C(=S)—N(R'R"), R¹ represents hydrogen, $(C_1-C_6)$alkyl, $(C_2-C_6)$alkenyl, substituted or unsubstituted aralkyl, heteroaralkyl, hydroxy$(C_1-C_6)$alkyl, R" represents hydrogen or $(C_1-C_6)$alkyl or R' and R" groups together form a 5 or 6 membered cyclic structures containing one or two hetero atoms, is prepared by treating compound of formula (I) where R¹ represents isothiocyanate group, by using appropriate amine such as methylamine, ethylamine, dimethylamine, diethylamine, benzylamine, aniline, proline, morpholine, thiomorpholine, pyridiylmethylamine and the like, in the presence of a solvent such as THF, DMF, toluene, and the like. The reaction may be carried at a temperature in the range of room temperature to 140° C., preferably at 60 to 100° C. The reaction time may range from 1 to 24 h, preferably 4 to 12 h.

In yet another embodiment of the present invention there is provided a process for the preparation of compound of formula (I) where Z represents $NR^b$ wherein $R^b$ represents hydrogen, $Y^1$ represents '=O' group, $Y^2$ and $Y^3$ independently represent hydrogen atom, from a compound of formula (I) where Z represents $NR^b$ wherein $R^b$ represents $(C_1-C_6)$alkyl group substituted with hydroxy group, $Y^1$ represents '=O group', $Y^2$ and $Y^3$ independently represent hydrogen atom,

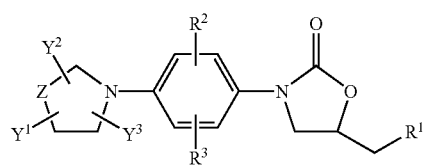

where all other symbols are as defined earlier.

The compound of formula (I) where Z represents $NR^b$ wherein $R^b$ represents hydrogen, $Y^1$ represents '=O' group, $Y^2$ and $Y^3$ independently represent hydrogen atom, from a compound of formula (I) wherein Z represents $NR^b$ wherein $R^b$ represents $(C_1-C_6)$alkyl group substituted with hydroxy group at the α-position, $Y^1$ represents '=O group', $Y^2$ and $Y^3$ independently represent hydrogen atom, may be prepared by treating with a base such as triethylamine, di-isopropylamine, di-isopropylethylamine, pyridine, piperidine, 4-dimethylaminopyridine (DMAP), 1,8-diazabicyclo(5.4.0)undec-7-ene (DBU), lithium diisopropylamide (LDA), potassium bis-(trimethyl silyl)amide, BuLi, $Na_2CO_3$, $K_2CO_3$, NaOH, KOH, NaOMe, NaOEt, NaOiPr, t-BuOK, NaH, KH and the like. The solvents used in the reaction may be selected from THF, ether, dioxane, toluene, benzene, DMF, DMSO, methylcyanide and the like. The temperature of the reaction may be maintained in the range of –20 to 150° C., preferably in the range of –10 to 100° C. The duraion of the reaction may be in the range of 0.2 to 64 h, preferably in the range of 1 to 48 h.

In still another embodiment of the present invention there is provided a process for the preparation of compound of formula (I), where Z represents $NR^b$ wherein $R^b$ represents substituted or unsubstituted $(C_1-C_6)$alkyl or aralkyl, $Y^1$ represents '=O group', $Y^2$ and $Y^3$ independently represent hydrogen atom; from a compound of formula (I) where Z represents $NR^b$ wherein $R^b$ represents hydrogen, $Y^1$ represents '=O' group, $Y^2$ and $Y^3$ independently represent hydrogen atom,

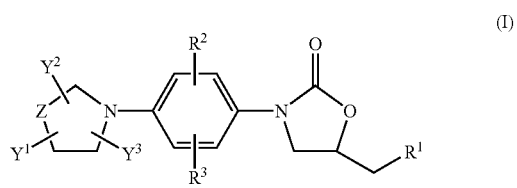

where all other symbols are as defined earlier.

The compound of formula (I), wherein Z represents $NR^b$ wherein $R^b$ represents substituted or unsubstituted $(C_1-C_6)$ alkyl or aralkyl, $Y^1$ represents '=O group', $Y^2$ and $Y^3$ independently represent hydrogen atom, from a compound of formula (I) wherein Z represents $NR^b$ wherein $R^b$ represents hydrogen, $Y^1$ represents '=O' group, $Y^2$ and $Y^3$ independently represent hydrogen atom, may be carried out in the presence of a base such as triethylamine, di-isopropylamine, di-isopropylethylamine, pyridine, piperidine, DMAP, 1,8-diazabicyclo(5.4.0)undec-7-ene (DBU), lithium diisopropylamide (LDA), potassium bis-(trimethyl silyl)amide, BuLi, $Na_2CO_3$, $K_2CO_3$, NaOH, KOH, NaOMe, NaOEt, NaOiPr, t-BuOK, NaH, KH and the like, followed by reacting with alkyl halide such as methyliodide, methoxymethylchloride, allylbromide, benzylbromide and the like. The solvent used in the reaction may be selected from DMF, DMSO, THF, dioxane, benzene, toluene and the like. The temperature of the reaction may be maintained in the range of –5 to 150° C., preferably in the range of 0° C. to reflux temperature of the solvent. The duration of the reaction may be in the range of 0.2 to 48 h, preferably in the range of 0.5 to 24 h. An alkyl halide or aralkyl halide may also be used.

In another embodiment of the present invention there is provided a process for the preparation of a compound of formula (I) where R¹ represents halogen, from compound of formula (I) where R¹ represents hydroxy group,

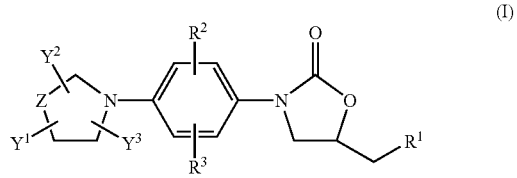

where all other symbols are as defined above.

The compound of formula (I) where R¹ represents halogen is prepared from compound of formula (I) where Rk represents hydroxy group may be carried out by treating with a tetrahalomethane group such as $CBr_4$, $CCl_4$ or the like, in the presence of $PPh_3$, $P(alkyl)_3$ and the like. The reaction may be carried out in the presence of a solvent such as dry dichloromethane, chloroform, tetrachloromethane, benzene, DMF, DMSO, THF and the like. The temperature of the reaction may be maintained in the range of 0 to 60° C., preferably at room temperature. The duration of the reaction may be in the range of 2 to 24 h, preferably 8 to 13 h.

In another embodiment of the present invention there is provided a process for the preparation of a compound of formula (I) where R¹ represents SH, from compound of formula (I) where R¹ represents halogen atom,

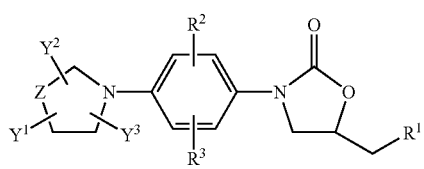

where all other symbols are as defined above, which comprises (i) reacting the compound of formula (I) where $R^1$ represents halogen atom, to produce a compound of formula (XX),

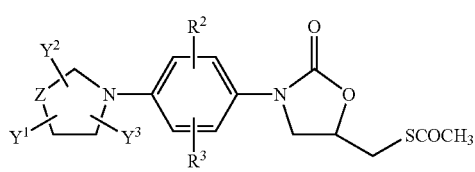

where all other symbols are as defined earlier, with a base and thioacetic acid, (ii) reacting the compound of formula (XX), to produce a compound of formula (I) where $R^1$ represents SH group and all other symbols are as defined earlier, with base.

The compound of formula (XX) is prepared from compound of formula (I) where $R^1$ represents hydroxy group is prepared by using thioacetic acid in the presence of a base such as triethylamine, di-isopropylamine, di-isopropylethylamine, pyridine, piperidine, DMAP, 1,8-diazabicyclo(5.4.0) undec-7-ene (DBU), lithium diisopropylamide (LDA), potassium bis-(trimethyl silyl)amide, BuLi, $Na_2CO_3$, $K_2CO_3$, NaOH, KOH, NaOMe, NaOEt, NaOiPr, t-BuOK, NaH, KH and the like. The solvent used in the reaction may be selected from THF, benzene, dioxane and the like. The temperature of the reaction is maintained in the range of room temperature to reflux temperature, preferably at reflux temperature. The duration of the reaction is maintained in the range of 2 to 24 h, preferably 6 h.

The compound of formula (I), where $R^1$ represents SH group is prepared from compound of formula (XX) by reacting with a base such as $K_2CO_3$, NaOH, KOH, BuLi or the like. The reaction may be carried out at a temperature in the range of room temperature to reflux temprature. The duration of the reaction may be in the range of 1 to 24 h.

In still another embodiment of the present invention there is provided a novel intermediate of the formula (VII)

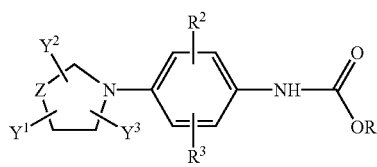

wherein $R^c$ represents $(C_1-C_8)$alkyl group such as methyl, ethyl, propyl, benzyl, allyl group and the like; $R^2$ and $R^3$ may be same or different and independently represent hydrogen, halogen atom, $(C_1-C_6)$alkyl group, halo$(C_1-C_6)$alkyl, cyano, nitro, $SR^a$, $NR^a$, or $OR^a$ where $R^a$ represents substituted or unsubstituted $(C_1-C_6)$alkyl group, or halo$(C_1-C_6)$alkyl; Z represents S, O, =CH or $NR^b$ where $R^b$ represents hydrogen or substituted or unsubstituted $(C_1-C_6)$alkyl, $(C_2-C_6)$alkenyl, $(C_1-C_6)$cycloalkyl, $(C_1-C_6)$alkoxy, aryl, aralkyl, aryloxy, $(C_1-C_6)$alkylcarbonyl, arylcarbonyl, $(C_1-C_6)$alkoxycarbonyl or aryloxycarbonyl; $Y^1$ represents =O or =S group; $Y^2$ and $Y^3$ independently represent hydrogen, halogen, cyano, nitro, formyl, hydroxy, amino, =O, =S group or substituted or unsubstituted groups selected from $(C_1-C_6)$alkyl, hydroxy$(C_1-C_6)$alkyl, $(C_1-C_6)$alkoxy$(C_1-C_6)$alkyl, $(C_1-C_6)$alkoxycarbonyl, carboxy$(C_1-C_6)$alkyl, $(C_1-C_6)$alkylsulfonyl, $(C_1-C_6)$alkylcarbonylamino$(C_1-C_6)$alkyl, arylcarbonylamino$(C_1-C_6)$alkyl, $(C_1-C_6)$alkylcarbonyloxy$(C_1-C_6)$alkyl, amino$(C_1-C_6)$alkyl, mono$(C_1-C_6)$alkylamino, di$(C_1-C_6)$alkylamino, arylamino, $(C_1-C_6)$alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms.

The novel intermediate of formula (VII) may be prepared by a process, which comprises:

(i) reacting a compound of formula (III)

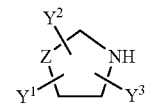

where all the symbols are as defined earlier, with a compound of formula (IV)

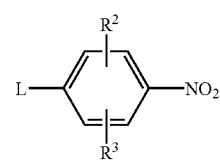

where L represents a leaving group such as halogen atom, alkoxy, sulfonyl groups and the like; $R^2$ and $R^3$ are as defined earlier, to produce a compound of formula (V)

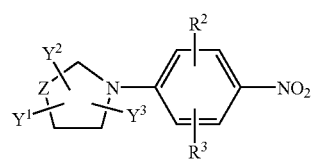

where $Y^1$, $Y^2$, $Y^3$, $R^2$, $R^3$ and Z are as defined earlier, (ii) reducing the compound of formula (V) to produce a compound of formula (VI)

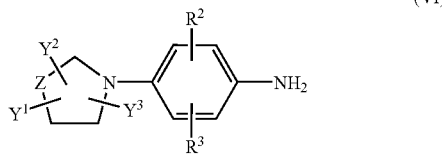

where $Y^1$, $Y^2$, $Y^3$, $R^2$, $R^3$ and Z are as defined earlier, (iii) reacting the compound of formula (VI) with alkylchloroformate, to produce a compound of formula (VII)

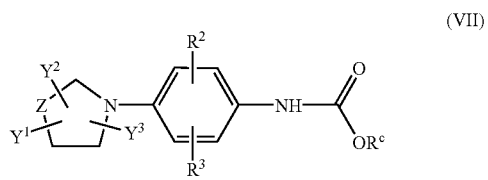

where $R^c$, $Y^1$, $Y^2$, $Y^3$ $R^2$, $R^3$ and Z are as defined above,

The reaction of a compound of formula (III) with a compound of formula (IV) to produce a compound of formula (V) may be carried out using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform and the like or mixtures thereof. The reaction may be carried out in inert atmosphere, which may be maintained using inert gases such as $N_2$ or Ar. The reaction may be carried out at a temperature in the range of 20° C.–100° C., preferably at a temperature in the range of ambient to 80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature from 25 to 60° C., preferably at room temperature. The reaction time ranges from 2 to 48 h. The reduction may also be carried out by employing metal in mineral acids such Sn/HCl, Fe/HCl, Zn/HCl, $Zn/CH_3CO_2H$ and the like.

The conversion of compound of formula (VI) to compound of formula (VII) may be carried out with an alkylchloroformate such as methychloroformate, ethylchloroformate, propylchloroformate, benzylchloroformate and the like. The solvent of the reaction may be selected from water, acetone, tetrahydrofuran (THF), acetonitrile, dichloromethane (DCM) and the like or mixtures thereof. The reaction may be carried out in the presence of base such as $K_2CO_3$, $Na_2CO_3$, NAH, KOH, triethylamine and the like. The temperature of the reaction may be carried out in the presence of 0 to 60° C., preferably at 0° C. to room temperature. The time of the reaction is maintained in the range of 1–12 h, preferably in the range of 1–4 h.

In still another embodiment of the present invention there is provided a novel intermediate of formula (VI)

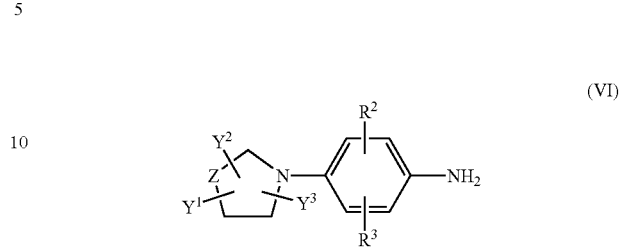

where $R^2$ and $R^3$ may be same or different and independently represent hydrogen, halogen atom, $(C_1-C_6)$alkyl group, halo$(C_1-C_6)$alkyl, cyano, nitro, $SR^a$, $NR^a$, or $OR^a$ where $R^a$ represents substituted or unsubstituted $(C_1-C_6)$alkyl group, or halo$(C_1-C_6)$alkyl; Z represents S, O, =CH or $NR^b$ where $R^b$ represents hydrogen or substituted or unsubstituted $(C_1-C_6)$alkyl, $(C_2-C_6)$alkenyl, $(C_1-C_6)$cycloalkyl, $(C_1-C_6)$alkoxy, aryl, aralkyl, aryloxy, $(C_1-C_6)$alkylcarbonyl, arylcarbonyl, $(C_1-C_6)$alkoxycarbonyl or aryloxycarbonyl; $Y^1$ represents =O or =S group; $Y^2$ and $Y^3$ independently represent hydrogen, halogen, cyano, nitro, formyl, hydroxy, amino, =O, =S group or substituted or unsubstituted groups selected from $(C_1-C_6)$alkyl, hydroxy$(C_1-C_6)$alkyl, $(C_1-C_6)$alkoxy$(C_1-C_6)$alkyl, $(C_1-C_6)$alkoxycarbonyl, carboxy$(C_1-C_6)$alkyl, $(C_1-C_6)$alkylsulfonyl, $(C_1-C_6)$alkylcarbonylamino$(C_1-C_6)$alkyl, arylcarbonylamino$(C_1-C_6)$alkyl, $(C_1-C_6)$alkylcarbonyloxy$(C_1-C_6)$alkyl, amino$(C_1-C_6)$alkyl, mono$(C_1-C_6)$alkylamino, di$(C_1-C_6)$alkylamino, arylamino, $(C_1-C_6)$alkoxy, aryl, aryloxy, aralkyl, heteroaryl, heteroaralkyl, heterocyclyl or heterocycloalkyl; any two of $Y^2$ and $Y^3$ when present on adjacent carbon atoms together may also form a substituted or unsubstituted 5 or 6 membered aromatic or non-aromatic cyclic structure, optionally containing one or two hetero atoms.

The novel intermediate of formula (VI) may be prepared by a process, which comprises:

(i) reacting a compound of formula (III)

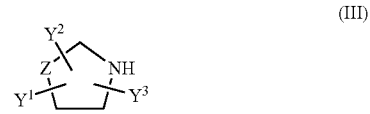

where all the symbols are as defined earlier, with a compound of formula (IV)

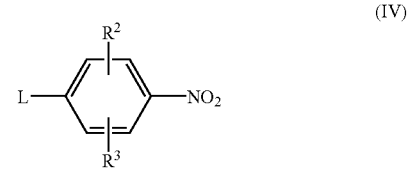

where L represents a leaving group such as halogen atom, alkoxy, sulfonyl groups and the like; $R^2$ and $R^3$ are as defined earlier, to produce a compound of formula (V)

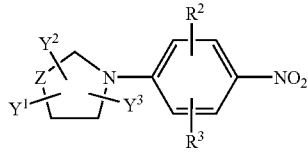

(V)

where $Y^1$, $Y^2$, $Y^3$, $R^2$, $R^3$ and Z are as defined earlier, and (ii) reducing the compound of formula (V) to produce a compound of formula (VI)

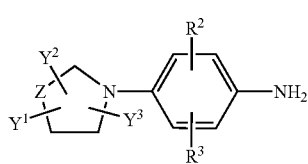

(VI)

where $Y^1$, $Y^2$, $Y^3$, $R^2$, $R^3$ and Z are as defined earlier.

The reaction of a compound of formula (III) with a compound of formula (IV) to produce a compound of formula (V) may be carried out using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform and the like or mixtures thereof. The reaction may be carried out in inert atmosphere, which may be maintained using inert gases such as $N_2$ or Ar. The reaction may be carried out at a temperature in the range of 20° C.–100° C., preferably at a temperature in the range of ambient to 80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature from 25 to 60° C., preferably at room temperature. The reaction time ranges from 2 to 48 h. The reduction may also be carried out by employing metal in mineral acids such as Sn/HCl, Fe/HCl, Zn/HCl, Zn/$CH_3CO_2H$ and the like.

In yet another embodiment of the present invention there is provided a novel intermediate of formula (X)

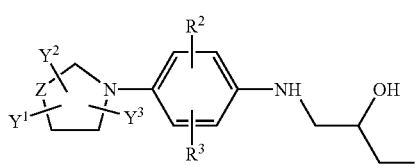

(X)

wherein $R^1$ represents halo, azido, thioalcohol, isothiocyanate, $OR^4$, $NHR^4$ or $N(R^4)_2$, where $R^4$ represents hydrogen atom, or substituted or unsubstituted groups selected from acyl, thioacyl, ($C_1$–$C_6$)alkoxycarbonyl, ($C_3$–$C_6$)cycloalkoxythiocarbonyl, ($C_2$–$C_6$)alkenyloxycarbonyl, ($C_2$–$C_6$)alkenylcarbonyl, aryloxycarbonyl, ($C_1$–$C_6$)alkoxythiocarbonyl, ($C_2$–$C_6$)alkenyloxythiocarbonyl, aryloxythiocarbonyl, —C(=O)—C(=O)-alkyl, —C(=O)—C(=O)-aryl, —C(=O)—C(=O)-alkoxy, —C(=O)—C(=O)-aryloxy, —(C=S)—S-alkyl, —(C=S)—$NH_2$, —(C=S)—NH-alkyl, —C(=S)—N-(alkyl)$_2$, —C(=S)—NH-alkenyl, (C=S)—(C=O)-alkoxy, —(C=S)—(C=O)-aryloxy, —C(=S)—O—(C=O)-alkyl, C(=S)—C(=S)-alkyl, —C(=S)—C(=S)-aryl, thiomorpholinylthiocarbonyl or pyrrolidinylthiocarbonyl; $R^2$ and $R^3$ may be same or different and independently represent hydrogen, halogen atom, ($C_1$–$C_6$)alkyl group, halo($C_1$–$C_6$)alkyl, cyano, nitro, $SR^a$, $NR^a$, $OR^a$ where $R^a$ represents substituted or unsubstituted ($C_1$–$C_6$)alkyl group, or halo($C_1$–$C_6$)alkyl; Z represents S, O, =CH or $NR^b$ where $R^b$ represents hydrogen or substituted or unsubstituted ($C_1$–$C_6$)alkyl, ($C_2$–$C_6$)alkenyl, ($C_1$–$C_6$)cycloalkyl, ($C_1$–$C_6$)alkoxy, aryl, aralkyl, aryloxy, ($C_1$–$C_6$) alkylcarbonyl, arylcarbonyl, ($C_1$–$C_6$)alkoxycarbonyl or aryloxycarbonyl; $Y^1$ represents =O or =S group and $Y^2$ or $Y^3$ represents hydrogen, halogen, cyano, nitro, formyl, hydroxy, amino, =O, =S group or substituted or unsubstituted groups selected from ($C_1$–$C_6$)alkyl, hydroxy($C_1$–$C_6$)alkyl, ($C_1$–$C_6$)alkoxy($C_1$–$C_6$)alkyl, ($C_1$–$C_6$)alkoxycarbonyl, carboxy($C_1$–$C_6$)alkyl, ($C_1$–$C_6$)alkylsulfonyl, ($C_1$–$C_6$)alkylcarbonylamino($C_1$–$C_6$)alkyl, arylcarbonylamino ($C_1$–$C_6$)alkyl, ($C_1$–$C_6$)alkylcarbonyloxy($C_1$–$C_6$)alkyl, amino($C_1$–$C_6$) alkyl, mono ($C_1$–$C_6$)alkylamino, di($C_1$–$C_6$)alkylamino, arylamino, ($C_1$–$C_6$)alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms.

The novel intermediate of formula (X) may be prepared by a process, which comprises:

(i) reacting a compound of formula (III)

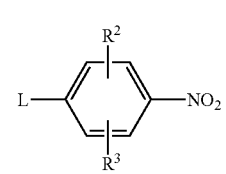

(III)

where all the symbols are as defined earlier, with a compound of formula (IV)

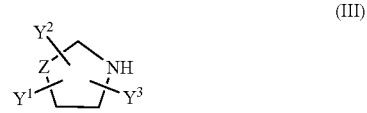

(IV)

where L represents a leaving group such as halogen atom, alkoxy, sulfonyl groups and the like; $R^2$ and $R^3$ are as defined earlier, to produce a compound of formula (V)

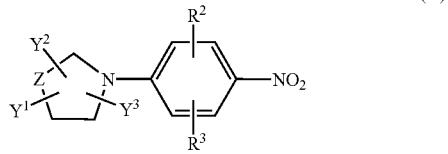

(V)

where $Y^1$, $Y^2$, $Y^3$, $R^2$, $R^3$ and Z are as defined earlier, (ii) reducing the compound of formula (V) to produce a compound of formula (VI)

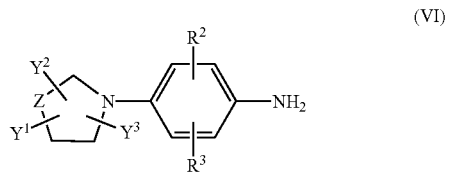

(VI)

where $Y^1$, $Y^1$, $Y^3$, $R^2$, $R^3$ and Z are as defined earlier, and (iii) reacting the compound of formula (VI) with a compound of formula (IX)

(IX)

where $R^1$ represents $NHR^4$ or $N(R^4)_2$, where $R^4$ represents hydrogen atom, or substituted or unsubstituted groups selected from acyl, thioacyl, $(C_1–C_6)$lkoxycarbonyl, $(C_3–C_6)$cycloalkoxythiocarbonyl, $(C_2–C_6)$alkenyloxycarbonyl, $(C_2–C_6)$alkenylcarbonyl, aryloxycarbonyl, $(C_1–C_6)$ alkoxythiocarbonyl, $(C_2–C_6)$ lkenyloxythiocarbonyl, aryloxythiocarbonyl, —C(=O)—C(=O)-alkyl, —C(=O)—C(=O)-aryl, —C(=O)—C(=O)-alkoxy, —C(=O)—C(=O)-aryloxy, —(C=S)—S-alkyl, —(C=S)—NH$_2$, —(C=S)—NH-alkyl, —C(=S)—N-(alkyl)$_2$, —C(=S)—NH-alkenyl, (C=S)—(C=O)-alkoxy, —(C=S)—(C=O)-aryloxy, —C(=S)—O—(C=O)-alkyl, C(=S)—C(=S)-alkyl, —C(=S)—C(=S)-aryl, thiomorpholinylthiocarbonyl or pyrrolidinylthiocarbonyl, to produce a compound of formula (X)

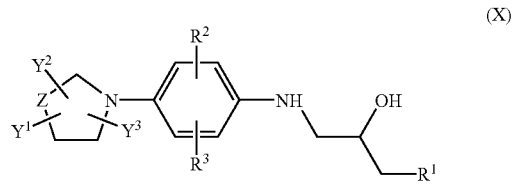

(X)

where $Y^1$, $Y^2$, $Y^3$, $R^2$, $R^3$ and Z are as defined above.

The reaction of a compound of formula (III) with a compound of formula (IV) to produce a compound of formula (V) may be carried out using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform and the like or mixtures thereof. The reaction may be carried out in inert atmosphere, which may be maintained using inert gases such as $N_2$ or Ar. The reaction may be carried out at a temperature in the range of 20° C.–100° C., preferably at a temperature in the range of ambient to 80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of solvents such as dioxane, acetic acid, ethyl acetate, THF, alcohol such as methanol, ethanol and the like or mixtures thereof. A pressure between atmospheric pressure to 60 psi may be used. The reaction may be carried out at a temperature from 25 to 60° C., preferably at room temperature. The reaction time ranges from 2 to 48 h. The reduction may also be carried out by employing metal in mineral acids such Sn/HCl, Fe/HCl, Zn/HCl, $Zn/CH_3CO_2H$ and the like.

The reaction of a compound of formula (VI) defined above with a compound of formula (IX) defined above to produce a compound of formula (X) may be carried out in the presence or absence of a base such as $K_2CO_3$, NaH, t-BuOK and the like or mixtures thereof. The reaction may be carried out in the presence of a solvent such as toluene, DMF, THF, or $CH_3CN$. The reaction may also be carried out in the presence of Lewis acids such as $BF_3.OEt_2$, $ZnCl_2$, $Ti(OiPr)_4$, lanthanide metal complexes and the like in the presence of DCE, DMF, THF or the like or mixtures thereof. The reaction temperature may be in the range of 0 to 120° C., preferably at a temperature in the range of 0 to 100° C. The reaction time may range from 3 to 24 h, preferably from 4 to 12 h.

In yet another embodiment of the present invention there is provided a novel intermediate of formula (XVI)

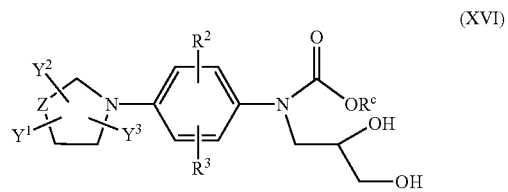

(XVI)

where $R^c$ represents $(C_1–C_8)$alkyl group such as methyl, ethyl, propyl, benzyl, allyl group and the like; $R^2$ and $R^3$ may be same or different and independently represent hydrogen, halogen atom, $(C_1–C_6)$alkyl group, halo$(C_1–C_6)$alkyl, cyano, nitro, $SR^a$, $NR^a$, $OR^a$ where $R^a$ represents substituted or unsubstituted $(C_1–C_6)$alkyl group, or halo$(C_1–C_6)$alkyl; Z represents S, O, =CH or $NR^b$ where $R^b$ represents hydrogen or substituted or unsubstituted $(C_1–C_6)$alkyl, $(C_2–C_6)$alkenyl, $(C_1–C_6)$cycloalkyl, $(C_1–C_6)$alkoxy, aryl, aralkyl, aryloxy, $(C_1–C_6)$alkylcarbonyl, arylcarbonyl, $(C_1–C_6)$alkoxycarbonyl or aryloxycarbonyl; $Y^1$ represents =O or =S group and $Y^2$ or $Y^3$ represents hydrogen, halogen, cyano, nitro, formyl, hydroxy, amino, =O, =S group or substituted or unsubstituted groups selected from $(C_1–C_6)$alkyl, hydroxy$(C_1–C_6)$alkyl, $(C_1–C_6)$alkoxy$(C_1–C_6)$alkyl, $(C_1–C_6)$alkoxycarbonyl, carboxy$(C_1–C_6)$alkyl, $(C_1–C_6)$alkylsulfonyl, $(C_1–C_6)$alkylcarbonylamino$(C_1–C_6)$alkyl, arylcarbonylamino($C_1$–$C_6$)alkyl, ($C_1$–$C_6$)alkylcarbonyloxy ($C_1$–$C_6$)alkyl, amino($C_1$–$C_6$)alkyl, mono($C_1$–$C_6$)alkylamino, di($C_1$–$C_6$)alkylamino, arylamino, ($C_1$–$C_6$)alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms.

The novel intermediate of formula (XVI) may be prepared by a process, which comprises:
(i) reacting a compound of formula (VII)

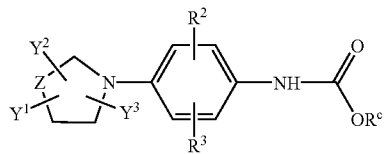

where all the symbols are as defined earlier, with a compound of formula (XIV)

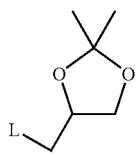

where L represents a leaving group such as halogen atom, alkoxy, sulfonyl groups and the like; to produce a compound of formula (XV)

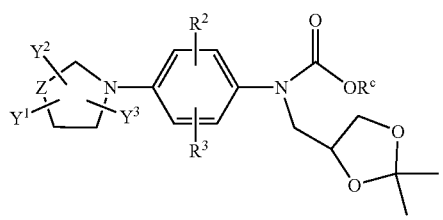

where $R^c$, $Y^1$, $Y^2$, $Y^3$, $R^2$, $R^3$ and Z are as defined earlier and
(ii) hydrolysing the acetonide moiety in the compound of formula (XV) using conventional methods to produce a compound of formula (XVI)

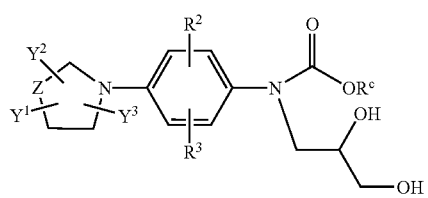

where $R^c$, $Y^1$, $Y^2$, $Y^1$, $R^2$, $R^3$ and Z are as defined earlier.

The reaction of a compound of formula (VII) with a compound of formula (XIV) to produce a compound of formula (XV) may be carried out in the presence of a base. The base employed may be selected from $K_2CO_3$, NaH, t-BuOK, LDA and the like. The reaction may be carried out in the presence of a solvent such as DMF, THF, DMSO, EtOH and the like. The reaction may be carried at a temperature in the range of –78 to 120° C., preferably at a temperature in the range of –78 to 100° C. The reaction time may range from 2 to 24 h, preferably from 2 to 20 h.

The hydrolysis of a compound of formula (XV) to produce a compound of formula (XVI) may be carried out using dilute mineral acid such as HCl, $H_2SO_4$ and the like, organic acids such as aqueous acetic acid, p-toluene sulfonic acid, camphor sulfonic acid, trifluoro acetic acid and the like. The reaction may be carried out in the presence of suitable solvent such as water, methanol, THF, dioxane and the like or mixtures thereof. The reaction may be carried at a temperature in the range of 30 to 100° C., preferably at a temperature in the range of 30 to 60° C. The reaction time may range from 10 min to 5 h, preferably from 30 min to 2.5 h.

In yet another embodiment of the present invention there is provided a novel intermediate of formula (XVIII)

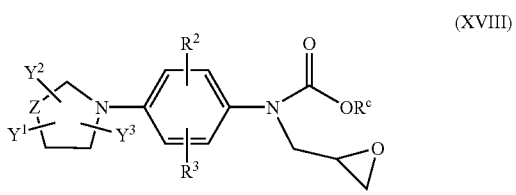

wherein $R^c$ represents ($C_1$–$C_8$)alkyl group such as methyl, ethyl, propyl, benzyl, allyl group and the like; $R^2$ and $R^3$ may be same or difference and independently represent hydrogen, halogen atom, ($C_1$–$C_6$)alkyl group, halo($C_1$–$C_6$)alkyl, cyano, nitro, $SR^a$, $NR^a$, $OR^a$ where $R^a$ represents substituted or unsubstituted ($C_1$–$C_6$)alkyl group, or halo($C_1$–$C_6$)alkyl; Z represents S, O, =CH or $NR^b$ where $R^b$ represents hydrogen or substituted or unsubstituted ($C_1$–$C_6$)alkyl, ($C_2$–$C_6$)alkenyl, ($C_1$–$C_6$)cycloalkyl, ($C_1$–$C_6$)alkoxy, aryl, aralkyl, aryloxy, ($C_1$–$C_6$)alkylcarbonyl, arylcarbonyl, ($C_1$–$C_6$)alkoxycarbonyl or aryloxycarbonyl; $Y^1$ represents =O or =S group and $Y^2$ or $Y^3$ represents hydrogen, halogen, cyano, nitro, formyl, hydroxy, amino, =O, =S group or substituted or unsubstituted groups selected from ($C_1$–$C_6$)alkyl, hydroxy($C_1$–$C_6$)alkyl, ($C_1$–$C_6$)alkoxy($C_1$–$C_6$)alkyl, ($C_1$–$C_6$)alkoxycarbonyl, carboxy($C_1$–$C_6$)alkyl, ($C_1$–$C_6$) alkylsulfonyl, ($C_1$–$C_6$)alkylcarbonylamino($C_1$–$C_6$)alkyl, arylcarbonylamino($C_1$–$C_6$)alkyl, ($C_1$–$C_6$)alkylcarbonyloxy ($C_1$–$C_6$)alkyl, amino($C_1$–$C_6$)alkyl, mono($C_1$–$C_6$)alkylamino, di($C_1$–$C_6$)alkylamino, arylamino, ($C_1$–$C_6$)alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms.

The novel intermediate of formula (XVIII) may be prepared by a process, which comprises: reacting a compound of formula (VII)

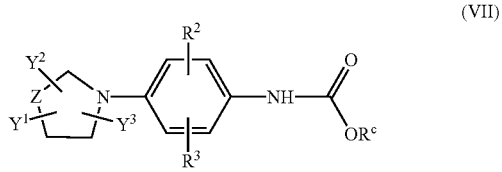

where all the symbols are as defined earlier, with a compound of formula (XVII)

where L represents a leaving group such as halogen atom, alkoxy, sulfonyl groups and the like; to produce a compound of formula (XVIII)

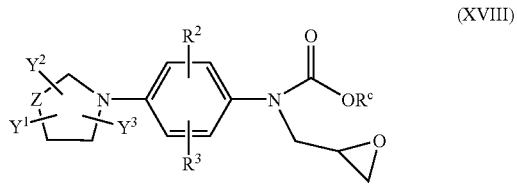

where $R^c$, $Y^1$, $Y^2$, $Y^3$, $R^2$, $R^3$ and Z are as defined earlier.

The reaction of a compound of formula (VII) defined above with a compound of formula (XVII) defined above may be carried out in the presence of a base such as NaH, NaOMe, $K_2CO_3$, n-BuLi, LDA and the like. The reaction may be carried out in the presence of a solvent such as DMF, THF, DMSO, benzene and the like or mixtures thereof. The reaction may be carried out at a temperature in the range of −78 to 70° C. preferably at a temperature in the range of −78 to 50° C. The reaction time may range from 1 to 15 h preferably 1 to 10 h.

It is appreciated that in any of the above-mentioned reactions, any reactive group in the substrate molecule may be protected according to conventional chemical practice. Suitable protecting groups in any of the above mentioned reactions are tertiarybutyldimethylsilyl, methoxymethyl, triphenyl methyl, benzyloxycarbonyl, tetrahydropyran (THP) etc, to protect hydroxyl or phenolic hydroxy group; N-tert-butoxycarbonyl (N-Boc), N-benzyloxycarbonyl (N-Cbz), N-9-fluorenyl methoxy carbonyl (N-FMOC), benzophenoneimine, propargyloxy carbonyl (POC) etc, for protection of amino or anilino group, acetal protection for aldehyde, ketal protection for ketone and the like. The methods of formation and removal of such protecting groups are those conventional methods appropriate to the molecule being protected.

The enantiomers may be prepared by using reactants in their single enantiomeric form in the process wherever applicable or by conducting the reaction in the presence of reagents or catalysts in their single enantiomeric form. The single enantiomers may also be prepared by resolving the racemic mixture by conventional methods. The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). Where appropriate the compounds of formula (I) may be resolved by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

The pharmaceutically acceptable salts are prepared by reacting the compounds of formula (I) wherever applicable with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, tromethamine, guanidine and their derivatives etc., may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used. The salts of amino acid groups and other groups may be prepared by reacting the compounds of formula (I) with the respective groups in solvents like alcohols, ketones, ether etc. Mixture of solvents may be used.

Various polymorphs of a compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Heating or melting the compound followed by gradual or fast cooling may also obtain polymorphs. The presence of poly-morphs may be determined by solid probe nmr spectroscopy, IR spectroscopy, differential scanning calorimetry, powder X-ray diffraction or such other techniques.

The present invention also provides pharmaceutical compositions, containing compounds of the general formula (I), as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and the like. The pharmaceutical compositions according to this invention can be used for the treatment of bacterial infections. They can also be used for the treatment of bacterial infections associated with multidrug resistance. Pharmaceutically acceptable solvates of compound of formula (I) forming part of this invention may be prepared by conventional methods such as dissolving the compounds of formula (I) in solvents such as water, methanol, ethanol etc., preferably water and recrystallizing by using different crystallization techniques.

The pharmaceutical compositions may be in the forms normally employed, such as tablets, capsules, powders, syrups, solutions, suspensions and the like, may contain flavorants, sweeteners etc., in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active compounds will be present in such pharmaceutical compositions in the amounts sufficient to provide the desired dosage in the range as described above. Thus, for oral administration, the compounds can be combined with a suitable solid, liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

In addition to the compounds of formula (I) the pharmaceutical compositions of the present invention may also contain or be co-administered with one or more known drugs selected from other clinically useful antibacterial agents such as β-lactams or aminoglycosides. These may include penicillins such as oxacillin or flucloxacillin and carbapenems such as meropenem or imiphenem to broaden the therapeutic effectiveness against, for example, methicillin-resistant staphylococci. Compounds of the formula (I) of the present invention may also contain or be co-admistered with bactericidal/permeability-increasing protein product (BPI) or efflux pump inhibitors to improve activity against gram negative bacteria and bacteria resistant to antimicrobial agents.

The compounds of the formula (I) as defined above are clinically administered to mammals, including human beings, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 5 mg/kg to about 20 mg/kg body weight of the subject per day administered singly or as a divided dose. However, the optimum dosage for the individual subject being treated will be determined by the person responsible for treatment, generally smaller doses being administered initially and thereafter increments made to determine the most suitable dosage.

The invention is explained in detail in the examples given below which are provided by way of illustration only and therefore should not be construed to limit the scope of the invention.

General Procedure for Preparations 1–9

A mixture of appropriate nitro compound such as 4-fluoronitrobenzene and the like, appropriate heterocycle such as oxazolidinone or its equivalents (1.1 eq) (An equivalent derivative of 2-oxazolidinone is a five membered heterocyclic group containing two heteroatoms selected from oxygen, nitrogen, and sulfur; and substituted by an =O or =S group, the heterocycle may be fused with substituted or unsubstituted phenyl group) and anhydrous $K_2CO_3$ (2.0 eq) in dry DMF was stirred at temperature ranging from 0 to 100° C. (depending on the substrate) overnight. Cold water was added to the reaction mixture and the solid formed was filtered. The filtered solids were dried to yield pure compound. Yield: 50–85%.

| S. No. | Preparation | Analytical data |
|---|---|---|
| 1 | (structure: oxazolidinone-phenyl-NO₂) | $^1$HNMR (CDCl$_3$, 200MHz): δ 8.25 (d, J=9.2Hz, 2H), 7.72(d, J=9.2Hz, 2H), 4.57(t, J=7.3Hz, 2H), 4.18(t, J=7.3Hz, 2H). Mass (CI method): 209. |
| 2 | (structure: oxazolidinone-(F-phenyl)-NO₂) | $^1$HNMR (CDCl$_3$, 200MHz): δ 8.12–7.93(m, 3H), 4.56(t, J=7.3Hz, 2H), 4.23(t, J=7.3Hz, 2H). Mass (CI method): 227. |

-continued

| S. No. | Preparation | Analytical data |
|---|---|---|
| 3 | 2,6-difluoro-4-nitrophenyl oxazolidin-2-one | ¹HNMR (CDCl₃, 200MHz): δ 7.92 (d, J=7.8Hz, 2H), 4.64(t, J=7.4Hz, 2H), 4.07(t, J=7.4Hz, 2H). Mass (CI method): 245, 215. |
| 4 | 3-fluoro-4-nitrophenyl oxazolidin-2-one | ¹HNMR (CDCl₃, 200MHz): δ 8.00 (m, 1H), 7.15(m, 2H), 4.56(t, J=7.4 Hz, 2H), 4.06(t, J=7.4Hz, 2H). Mass (CI method): 226, 180, 164, 152, 135, 109, 94. |
| 5 | 2-trifluoromethyl-4-nitrophenyl oxazolidin-2-one | ¹HNMR (CDCl₃, 200MHz): δ 8.64– 8.48(m, 2H), 7.69(d, J=8.8Hz, 1H), 4.60(t, J=7.3Hz, 2H), 4.01(t, J=7.3 Hz, 2H). Mass (CI method): 276, 232, 217, 171, 144. |
| 6 | 2-fluoro-4-nitrophenyl oxazolidine-2-thione | ¹HNMR (CDCl₃, 200MHz): δ 8.14– 8.04(m, 2H), 7.90(t, J=7.6Hz, 1H), 4.76(t, J=8.4Hz, 2H), 4.23(t, J=8.4 Hz, 2H). Mass (CI method): 242, 223, 167, 121, 94. |
| 7 | 2-fluoro-4-nitrophenyl thiazolidine-2-thione | ¹HNMR (CDCl₃, 200MHz): δ 8.14– 8.07(m, 2H), 7.72(t, J=7.6Hz, 1H), 4.43(t, J=7.6Hz, 2H), 3.57(t, J=7.6 Hz, 2H). Mass (CI method): 258, 239, 212, 193, 108. |
| 8 | 1-methyl-3-(2-fluoro-4-nitrophenyl)imidazolidine-2-thione | ¹HNMR (CDCl₃, 200MHz): δ 8.11– 8.02(m, 2H), 7.96(t, J=7.8Hz, 1H), 4.09–3.83(2t, 4H), 3.27(s, 2H). Mass (CI method): 255, 236, 209, 190. |
| 9 | 3-(4-nitrophenyl)-4-methylbenzoxazol-2(3H)-one, R = 4-Me | ¹HNMR (CDCl₃, 200MHz): δ 8.23 (m, 2H), 7.81(t, J=7.4Hz, 1H), 7.22 (t, J=7.4Hz, 1H), 7.03(d, J=8.4Hz, 1H). Mass (CI method): 288, 258, 243, 197, 94. |

A solution of 4-fluoronitrobenzene (5 g, 35.4 mmol) in CH₃CN (250 ml) was stirred at room temperature under argon overnight. The reaction mixture was filtered and the filtrate was concentrated. The residue obtained was suspended in pet. ether and filtered. The solids were collected to afford the nitro compound (4.1 g, 64%) as yellow crystals.

$^1$H NMR (DMSO+CDCl$_3$, 200 MHz): δ 7.97 (d, J=9.3 Hz, 2H), 7.09 (bs, 1H), 6.62 (d, J=9.3 Hz, 2H), 2.80–3.40 (m, 6H). Mass(CI method): 181, 152, 135, 105.

Preparation 11

1-(4-Nitrophenyl)-2-imidazolidinone

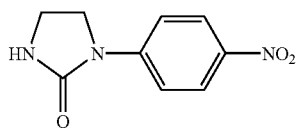

A solution of phosgene (20% in toluene, 13 ml, 26.5 mmol) in toluene was added drop wise to a solution of the diamine (4 g, 22 mmol) (obtained in preparation 10) and Et₃N (7.6 ml, 55 mmol) in dichloromethane (100 ml) at 0° C. under argon. After being stirred at same temperature for 1 h, the reaction mixture was poured in water and extracted with dichloromethane (4×150 ml). The combined organic extracts were washed with water, brine and dried. The residue obtained upon evaporation of the solvents was passed through a column of silica gel to afford the product (3 g, 66%) as yellow solid.

$^1$H NMR (CDCl$_3$, 200 MHz): δ 8.17 (d, J=9.3 Hz, 2H), 7.75 (d, J=9.2 Hz, 2H), 7.07 (bs, 1H), 4.00 (t, J=8.8 Hz, 2H), 3.59 (t, J=8.8 Hz, 2H). Mass(CI method): 207, 151, 105.

Preparation 12

1-Methyl-3-(4-nitrophenyl)-2-imidazolidinone

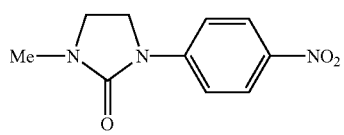

Sodium hydride (60% in oil, 138 mg, 5.3 mmol) was added portion wise to a solution of the nitro compound (1 g, 4.8 mmol) (obtained in preparation 11) in dry DMF (15 ml) under argon at 0° C. Stirred the reaction mixture at the same temperature for 15 min. Methyl iodide (MeI) (0.68 g, 4.8 mmol) was added and the reaction mixture was stirred for 1 h. Ice pieces were added to the reaction mixture and the solid formed was filtered to afford the product (900 mg, 84%) as yellow crystals.

$^1$H NMR (CDCl$_3$, 200 MHz): δ 8.19 (d, J=9.3 Hz, 2H), 7.70 (d, J=9.3 Hz, 2H), 3.88 (t, J=8.8 Hz, 2H), 3.54 (t, J=8.8 Hz, 2H), 2.93 (s, 3H). Mass(CI method): 222.

Preparation 13

1-(3-Fluoro-4-nitrophenyl)-4-imidazolidinone

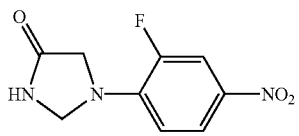

A solution of 4-imidazolidinone (9.5 g, 110.5 mmol), 3,4-difluoronitrobenzene (12.2 ml, 110.5 mmol) and diisopropyl ethylamine (28.6 ml, 165 mmol) in dry DMF (80 ml) was heated to 60° C. overnight under argon. The reaction mixture was allowed to cool to room temperature and ice pieces were added. The solid formed was filtered and washed with water. The solid was dried under air to yield the nitro compound (19.5 g, 78.5%) as yellow crystals.

$^1$H NMR (DMSO, 200 MHz): δ 8.81 (bs, 1H), 8.07–7.96 (m, 2H), 6.82 (t, J=8.8 Hz, 1H), 4.97 (s, 2H), 4.06 (s, 2H). Mass (CI method): 226, 185, 152.

Preparation 14

N1-phenyl-2-azidoacetamide

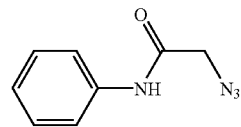

Chloroacetyl chloride (5.1 ml, 64.5 mmol) was added drop wise to a solution of aniline (5 g, 53.7 mmol) and Et₃N (18.7 ml, 134.3 mmol) in dichloromethane (150 ml) at 0° C. under argon. After the completion of reaction (TLC control), the reaction mixture was diluted with dichloromethane (300 ml). The resultant mixture was washed with water, brine and dried. The residue obtained upon evaporation of solvent was taken up in dry DMF (40 ml), added NaN₃ (6.15 g, 94.6 mmol) and the resultant mixture was stirred at 80° C. for 2 h. The reaction mixture was diluted with ethyl acetate and washed with water, brine and dried. The residue obtained upon evaporation of the solvent was chromatographed over silica gel to afford the azide (6 g, 63%).

Preparation 15

N1-phenyl-2-(2-fluoro-4-nitroanilino)acetamide

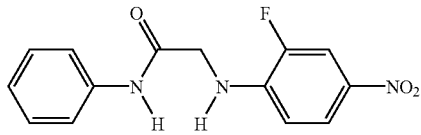

A solution of the azide (6 g, 34 mmol) obtained in preparation 14 was taken in MeOH (60 ml) and the resultant solution was hydrogenated over 10% Pd on charcoal (2.5 g) overnight. The reaction mixture was filtered on a celite pad and the filtrate was concentrated. To this residue dry DMF (40 ml) was added followed by diisopropyl ethyl amine (16.7 ml, 93.8 mmol) and 3,4-difluoronitrobenzene (3.8 ml, 37.5 mmol). The resultant solution was kept at 80° C. overnight with continuous monitoring by TLC. Ice-cold water was added to the reaction mixture and the solid separated was filtered to afford the nitro compound as a yellow solid (6 g, 61%).

$^1$H NMR (DMSO+CDCl$_3$, 200 MHz): δ 9.74 (bs, 1H), 7.84–8.00 (m, 2H), 7.58 (d, J=8.3 Hz, 2H), 7.30 (d, J=8.3 Hz, 2H), 7.08 (m, 1H), 6.66 (t, J=8.8 Hz, 1H), 6.45 (bs, 1H), 4.09 (d, J=5.4 Hz, 2H). Mass (CI Method): 290.

Preparation 16

N1-(2-anilinoethyl)-2-fluoro-4-nitroaniline

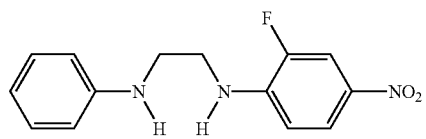

A 1 M solution of BH$_3$.THF (45 ml, 45 mmol) was added drop wise to a solution of the nitro compound (4.5 g, 15.5 mmol) (obtained in preparation 15) in dry THF (30 ml) at 0° C. under argon. The reaction mixture was stirred overnight at room temperature and then water was added cautiously to quench the excess borane. The volatiles were removed from the reaction mixture under vacuum and the residue was taken up in ethyl acetate (400 ml). The organic layer was washed with water, brine and dried. The residue obtained upon evaporation of the solvent was passed through column to afford the product (4 g, 93%).

$^1$H NMR (CDCl$_3$, 200 MHz): δ 8.02–7.86 (m, 2H), 7.26–7.18 (m, 2H), 6.82–6.62 (m, 4H), 4.94 (bs, 1H), 3.83 (bs, 1H), 3.51 (s, 4H). Mass (CI method): 274.

Preparation 17

1-(2-Fluoro-4-nitrophenyl)-3-phenyl-2-imidazolidinone

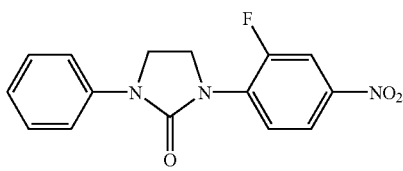

A solution of phosgene (20% in toluene, 7.4 ml, 14.7 mmol) was added drop wise to a solution of the diamine (4 g, 14.5 mmol) (obtained in preparation 16) and Et$_3$N (5.6 ml, 40.4 mmol) in dichloromethane (50 ml) at 0° C. under argon. Stirred for 2 h at the same temperature the reaction mixture was diluted with dichloromethane (300 ml) and washed with water, brine and dried. The crystals obtained upon evaporation of the solvents were suspended in petroleum ether and filtered. The product was isolated as yellow crystals (4 g, 91.4%).

$^1$H NMR (CDCl$_3$, 200 MHz): δ 8.10–7.11 (m, 8H), 4.22–4.00 (m, 4H). Mass (CI Method): 302, 106.

Preparation 18

1-(2-Fluoro-4-nitrophenyl)-3-hydroxymethyl-4-imidazolidinone

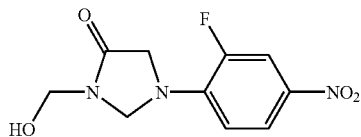

A mixture of 1-(3-fluoro-4-nitrophenyl)-4-imidazolidinone (9 g, 40 mmol) (obtained in preparation 13) and 40% solution of formaldehyde (100 mL) was heated to reflux for 4 h. The reaction mixture was allowed to cool to room temperature and ice water mixture was added. The precipitated solid was filtered and dried to give the product as yellow solid (8.5 g, 83% yield).

$^1$H NMR (DMSO-d$^6$, 200MHz): δ 8.10–7.95 (m, 2H), 6.90–6.80 (m, 1H), 6.20 (t, J=6.8 Hz, 1H), 5.13 (d, J=2.9 Hz, 2H), 4.77 (d, J=7.3 Hz, 2H), 4.19 (s, 2H).

Mass (CI method): 226.

Preparation 19

1-(2-Fluoro-4-nitrophenyl)-3-hydroxymethyl-4-imidazolidinone

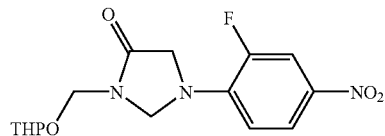

A solution of 1-(2-fluoro-4-nitrophenyl)-3-hydroxymethyl-4-imidazolidinone (6.7 g, 26.2 mmol) (obtained in preparation 18), pyridinium p-toluenesulphonate (PPTS) (65 mg, 0.39 mmol) and 3,4-dihydro-2H-pyran (3.6 mL, 39.4 mmol) in dichloromethane (100 mL) was stirred at room temperature under argon overnight. The reaction mixture was diluted with dichloromethane (400 mL), washed with half-saturated brine (2×100 mL) and dried. The residue obtained upon evaporation of solvent was passed through a column of silica gel to afford the product as yellow solid (7 g, 79%).

$^1$H NMR (CDCl$_3$, 200MHz): δ 8.05–7.85 (m, 2H), 6.60–6.45 (m, 1H), 5.30–4.70 (m, 5H), 4.17 (s, 2H), 4.20–3.30 (m, 4H), 2.00–1.40 (m, 6H). Mass (CI method): 340, 256, 237.

Preparation 20

General Procedure for the Conversion of

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring.

A solution of the nitro compound in THF was hydrogenated over 10% Pd on charcoal (catalytic amount) overnight. After the complete consumption of starting material, a 5% solution of $Na_2CO_3$ (2.2 eq) in water was added followed benzyl chloroformate (1.2 eq) at 0° C. After stirring the reaction mixture for 3 h at room temperature, it was filtered over celite bed and washed with ethyl acetate. The organic layer was separated from the filtrate and washed with water twice followed by brine. The organic extract was dried, evaporated and purified on a column of silica gel.

EXAMPLES

A. General rocedure for the conversion of

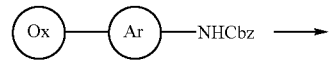

-continued

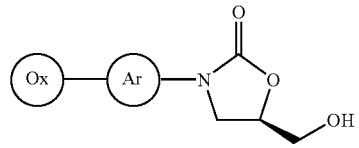

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring.

To a solution of the starting material in dry THF at −78° C. under argon was added 1.6M BuLi (1.2 eq) drop wise. The reaction mixture was stirred for 45 min at the same temperature and then R-glycidyl butyrate (1.2 eq) was added. Stirred for 1 h at −78° C. Then the cold bath was removed while monitoring with TLC. After 3–12 h, the reaction mixture was quenched with saturated $NH_4Cl$ solution and extracted with ethyl acetate. The combined organic extracts were washed with water, brine and dried. The residue obtained upon evaporation of solvents was chromatographed over silica gel to afford the product.

Examples 1–19 have been prepared according to the general procedure A.

| Example No. | Structure | Analytical Data |
|---|---|---|
| 1 | 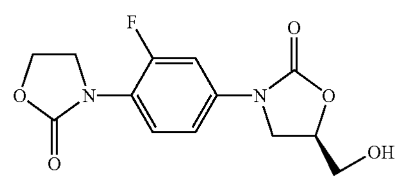 | $^1$HNMR (DMSO-d$^6$, 200MHz): δ 7.68–7.50(m, 2H), 7.38(d, J=8.8Hz, 1H), 5.23(t, J=5.8Hz, 1H), 4.73–4.72(m, 1H), 4.47(t, J=7.4 Hz, 2H), 4.14–3.80(m, 4H), 3.68–3.56(m, 2H). |
| 2 | 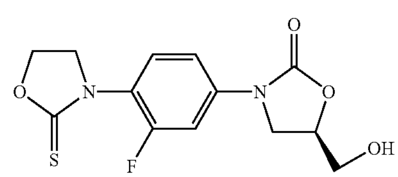 | $^1$HNMR (CDCl$_3$, 200MHz): δ 7.73(d, J=11.6Hz, 1H), 7.52 (t, J=8.8Hz, 1H), 7.29(d, J= 8.8Hz, 1H), 4.89(bs, 1H), 4.76(t, J=2H), 4.17(t, J= 8.8Hz, 2H), 3.93–3.68(m, 4H). |
| 3 | 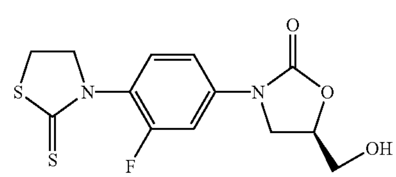 | $^1$HNMR (CDCl$_3$, 200MHz): δ 7.70(dd, J=12.7Hz and 2.2 Hz, 1H), 7.44–7.26(m, 2H), 4.75–4.68(m, 2H) 4.37(t, J= 7.8Hz, 2H), 4.04–3.56(m, 4H), 3.48(t, J=7.8Hz, 2H). |
| 4 | 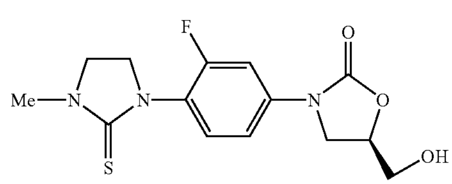 | $^1$HNMR (CDCl$_3$, 200MHz): δ 7.62(dd, J=2.4Hz and 12.7 Hz, 1H), 7.47(t, J=8.4Hz, 1H), 7.24–7.20(m, 1H), 4.77–4.69(m, 1H), 4.10–3.81(m, 5 H), 3.77–3.68(m, 4H), 3.23(s, 3H). |

-continued

| Example No. | Structure | Analytical Data |
|---|---|---|
| 5 | 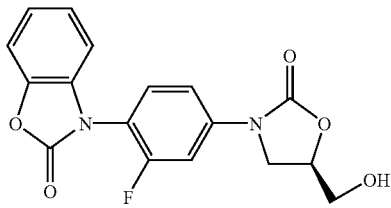 | ¹HNMR (CDCl$_3$, 200MHz): δ 7.85–7.79(m, 1H), 7.58(t, J= 8.0Hz, 1H), 7.46–7.42(m, 1H), 7.30–7.18(m, 4H), 6.90–6.87(m, 1H), 4.90–4.75(m, 1H), 4.15–4.07(m, 3H), 3.87–3.81(m, 1H). |
| 6 | 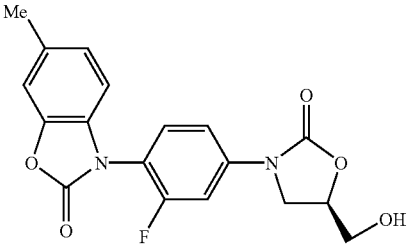 | ¹HNMR (CDCl$_3$, 200MHz): δ 7.76(dd, J=2.4Hz and 12.2 Hz, 1H), 7.53–7.26(m, 2H), 7.11(s, 1H), 6.97(d, J=8.4 Hz, 1H), 6.72(d, J=7.8Hz, 1H), 4.81–4.65(m, 1H), 4.09–3.82(m, 4H), 2.41(s, 3H), 2.09(hump, 1H). |
| 7 | 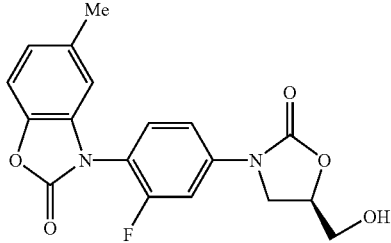 | ¹HNMR (CDCl$_3$, 200MHz): δ 7.77(d, J=10.4Hz, 1H), 7.57–7.26(m, 3H), 6.96(d, J= 7.8Hz, 1H), 6.64(s, 1H), 4.82–4.71(m, 1H), 4.14–4.05 (m, 3H), 3.84–3.78(m, 2H), 2.35(s, 3H). |
| 8 | 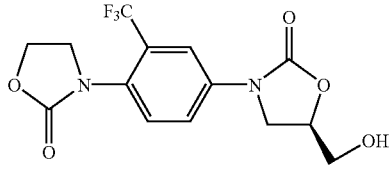 | ¹HNMR (CDCl$_3$, 200MHz): δ 7.92–7.89(m, 2H), 7.44(d, J= 7.8Hz, 1H), 7.80–7.71(m, 1H), 4.54(t, J=7.2Hz, 2H), 4.08–3.89(m, 6H), 2.16(s, 1H). |
| 9 | 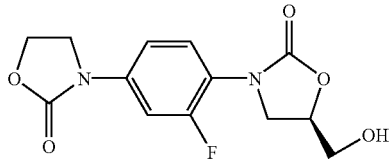 | ¹HNMR (CDCl$_3$, 200MHz): δ 7.69–7.48(m, 2H), 7.23(d, J= 8.8Hz, 1H), 4.81–4.72(m, 1H), 4.54(t, J=7.4Hz, 2H), 4.13–3.69(m, 6H). |
| 10 | 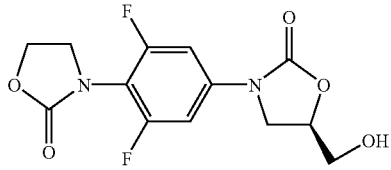 | ¹HNMR (CDCl$_3$, 200MHz): δ 7.29(d, J=10.8Hz, 2H), 4.80–4.73(m, 1H), 4.57(t, J= 15.6Hz, 2H), 4.00–3.73(m, 8H). |
| 11 | 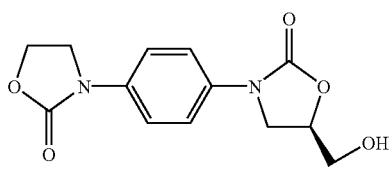 | ¹HNMR (CDCl$_3$, 200MHz): δ 7.59(s, 4H), 5.24(t, J=5.4 Hz, 1H), 4.67(bs, 1H), 4.45 (t, J=7.4Hz, 2H), 4.13–4.02 (m, 3H), 3.88–3.54(m, 3H). |

-continued

| Example No. | Structure | Analytical Data |
|---|---|---|
| 12 | 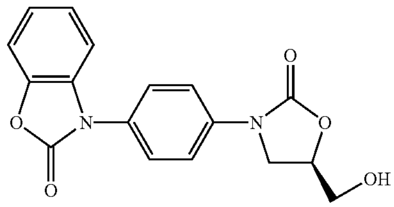 | ¹HNMR (CDCl₃, 200MHz): δ 7.79(d, J=9.2Hz, 2H), 7.72 (d, J=9.2Hz, 2H), 7.59–7.03 (m, 4H), 5.18(t, J=5.8Hz, 1H), 4.80–4.71(m, 1H), 4.18–4.02(m, 2H), 3.98–3.68(m, 2H). |
| 13 | 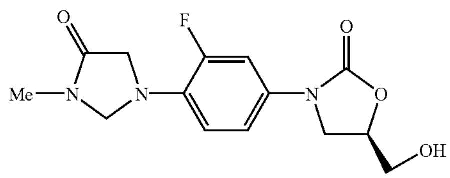 | ¹HNMR (CDCl₃, 200MHz): δ 2.9(s, 3H), 4.1(t, 1H), 3.9(m, 6H), 4.7(m, 1H), 4.8(s, 2H), 6.8(t, 1H), 7.2(d, 1H). |
| 14 | 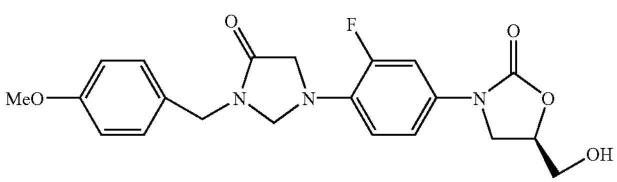 | ¹HNMR (CDCl₃, 200MHz): δ 7.4(dd, J=2Hz and 15.4Hz, 1H), 7.2(d, J=8.8Hz, 2H), 7.0(d, J=9.4Hz, 1H), 6.85(d, J=8.4Hz, 2H), 6.5(t, J=9.2 Hz, 1H), 4.75(s, 3H), 4.50(s, 2H), 3.95(m, 6H), 3.8(s, 3H). |
| 15 | 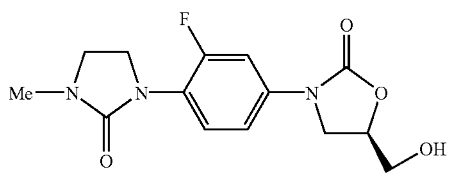 | ¹HNMR (CDCl₃, 200MHz): δ 7.55(dd, J=2.4Hz and 13.4 Hz, 1H), 7.45(t, J=8.8Hz, 1H), 7.10(dd, J=2.2Hz and 13.0Hz, 1H), 4.66(m, 1H), 3.81(m, 6H), 3.47(t, 2H), 2.8 (s, 3H). |
| 16 | 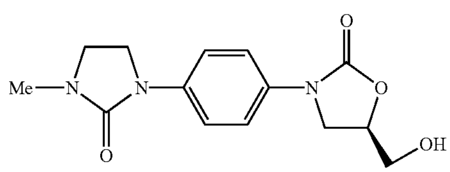 | ¹HNMR (CDCl₃, 200MHz): δ 2.8(s, 3H), 3.4(m, 3H), 4.7 (m, 1H), 7.5(m, 4H). |
| 17 | 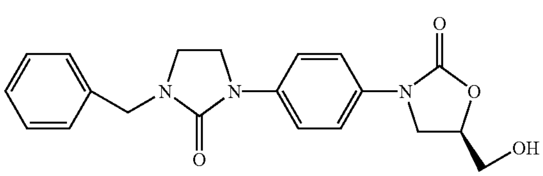 | ¹HNMR (CDCl₃, 200MHz): δ 7.7–7.2(m, 9H), 4.8–4.6(m, 1H), 4.5(s, 2H), 4.1–3.7(m, 6H). 3.4(t, J=8.8Hz, 2H) |
| 18 | 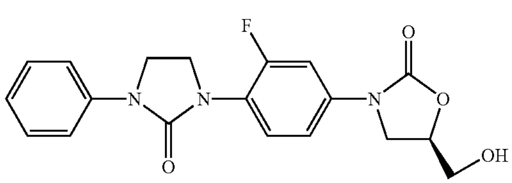 | ¹HNMR (CDCl₃, 200MHz): δ 7.5–7.7(m, 4H), 7.3–7.4(m, 2H), 7.2(d, J=8.8Hz, 1H), 7.1(t, 4H), 4.7(m, 1H), 3.9–4.1(m, 6H), 3.9(s, 1H), 3.7 (m, 1H). |
| 19 | 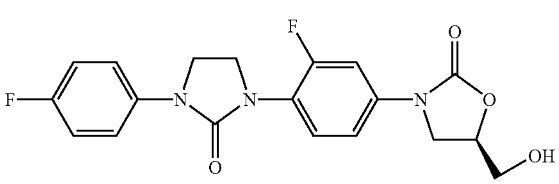 | ¹HNMR (CDCl₃, 200MHz): δ 7.5(m, 4H), 7.2(m, 1H), 7.0 (m, 2H), 4.7(m, 2H), 4.0(m, 7H), 3.8(m, 1H) |

B. General procedure for the conversion of

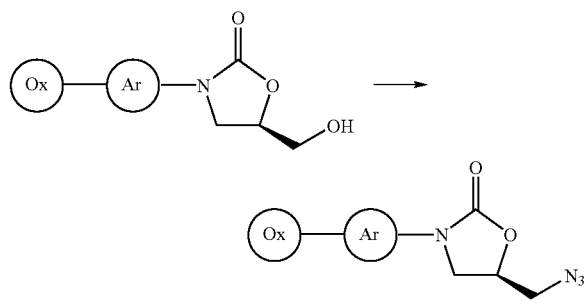

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring.

To a solution of the alcohol, triethylamine (2.2 eq) in dry dichloromethane, methane sulfonylchloride (1.1 eq) was added at 0° C. under argon. The reaction mixture was warmed to room temperature over 2 h and then diluted with dichloromethane. The organic layer was washed with water, brine and dried. The residue obtained upon evaporation of the solvent was taken up in dry DMF and then $NaN_3$ (1.5 eq) was added at room temperature. The resultant mixture was heated to 80° C. for 2–5 h while monitoring by TLC. Allowed the reaction mixture to attain room temperature, water was added and extracted with ethyl acetate. The combined organic extracts were washed with water (3 times), brine and dried. The residue obtained upon evaporation of the solvent was passed through column to obtain the azide.

Examples 20–31 have been prepared according to the general procedure B.

| Example No. | Structure | Analytical Data |
|---|---|---|
| 20 | 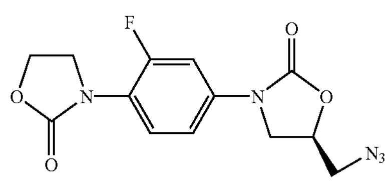 | $^1$HNMR (DMSO-d$^6$, 200MHz): δ 7.67–7.52(m, 2H), 7.38(d, J=8.8Hz, 1H), 4.95–4.88(m, 1H), 4.47(t, J=7.2Hz, 2H), 4.16(t, J=9.4 Hz, 1H), 4.02–3.64(m, 5H). |
| 21 | 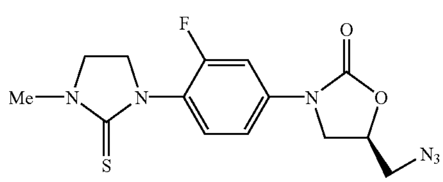 | $^1$HNMR (CDCl$_3$, 200MHz): δ 7.62(dd, J=2.4Hz and 12.7 Hz, 1H), 7.48(t, J=8.4Hz, 1H), 7.22–7.17(m, 1H), 4.85–4.73(m, 1H), 4.16–3.52(m, 8H), 3.22(s, 3H). |
| 22 | 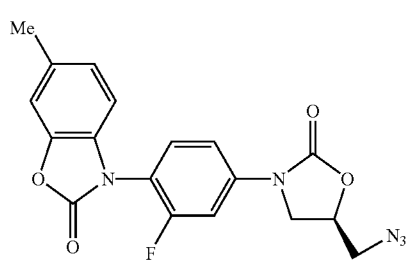 | $^1$HNMR (CDCl$_3$, 200MHz): δ 7.75(dd. J=2.0Hz and 12.2 Hz, 1H), 7.54(t, J=8.8Hz, 1H), 7.40–7.26(m, 1H), 7.10 (s, 1H), 6.97(d, J=7.8Hz, 1H), 6.71(d, J=6.8Hz, 1H), 4.87–4.79(m, 1H), 4.17–3.57 (m, 4H), 2.41(s, 3H). |
| 23 | 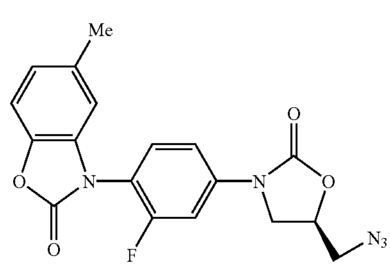 | $^1$HNMR (CDCl$_3$, 200MHz): δ 7.81(d, 1H), 7.54(t, 1H), 7.45–7.01(m, 3H), 6.67(s, 1H), 4.91–4.79(m, 1H), 3.95–3.47(m, 4H), 2.38(s, 3H). |

| Example No. | Structure | Analytical Data |
|---|---|---|
| 24 | 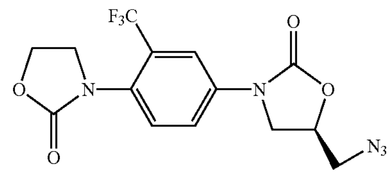 | ¹HNMR (CDCl₃, 200MHz): δ 7.89(d, J=7.4Hz, 2H), 7.43 (d, J=9.4Hz, 1H), 4.87–4.80 (m, 1H), 4.54(t, J=7.2Hz, 2H), 4.12(t, J=8.8Hz, 2H), 3.97–3.55(m, 4H). |
| 25 | 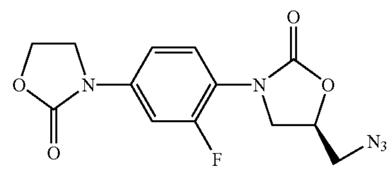 | ¹HNMR (CDCl₃, 200MHz): δ 7.71–7.50(m, 2H), 7.17(d, J=8.8Hz, 1H), 4.89–4.75(m, 1H), 4.52(t, J=7.2Hz, 2H), 4.47–3.55(m, 6H). |
| 26 | 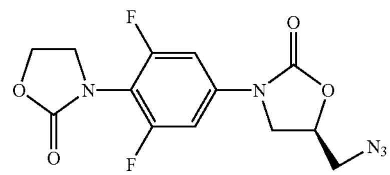 | ¹HNMR (CDCl₃, 200MHz): δ 7.31(s, 2H), 4.83–4.81(m, 1H), 4.57(t, J=7.8Hz, 2H), 4.09–3.55(m, 6H). |
| 27 | 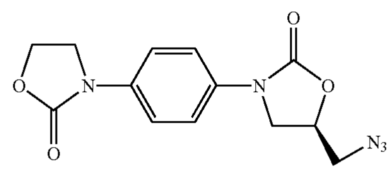 | ¹HNMR (DMSO-d⁶, 200MHz): δ 7.64(s, 4H), 4.98–4.89(m, 1H), 4.50(t, J=7.4Hz, 2H), 4.25–4.07(m, 4H), 3.88–3.70(m, 2H). |
| 28 | 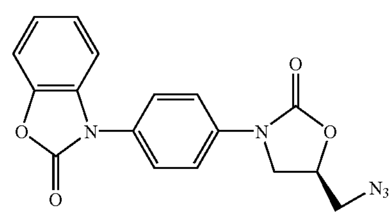 | ¹HNMR (CDCl₃, 200MHz): δ 7.75(d, J=9.2Hz, 2H), 7.59 (d, J=9.2Hz, 2H) 7.48–7.03 (m, 4H), 4.89–4.81(m, 1H), 4.16(t, J=9.2Hz, 1H), 3.98–3.58(m, 3H). |
| 29 | 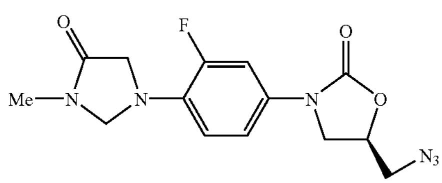 | ¹HNMR (CDCl₃, 200MHz): δ 7.5–7.4(dd, 1H), 7.1(dd, 1H), 6.5(t, 1H), 4.9(s, 2H), 4.8–4.7 (m, 1H), 4.1–3.5(m, 6H), 3.0(s, 3H). |
| 30 | 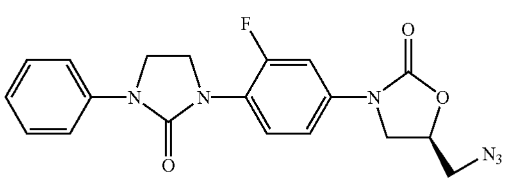 | ¹HNMR (CDCl₃, 200MHz): δ 7.6(m, 4H), 7.35(t, 2H), 7.0–7.2(m, 2H), 4.8(m, 1H), 4.1 (m, 1H), 4.0(s, 4H), 3.9(m, 1H), 3.7(m, 2H). |
| 31 | 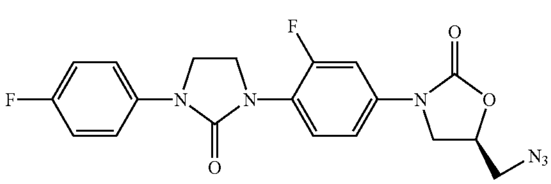 | ¹HNMR (CDCl₃, 200MHz): δ 7.6(m, 4H), 7.2(m, 1H), 7.0 (m, 2H), 4.8(m, 1H), 4.1(m, 1H), 4.0(s, 4H), 3.9(m, 1H), 3.6(m, 2H). |

C. General procedure for the conversion of

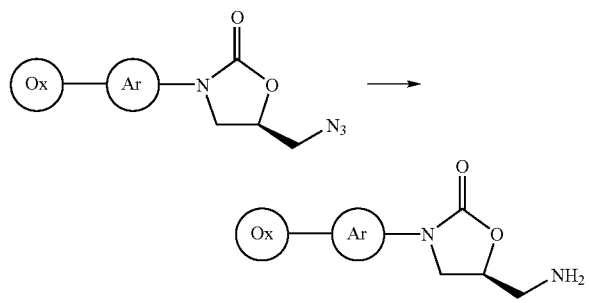

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring.

Procedure (i):

A solution of the azide in THF:MeOH (1:3) was hydrogenated over 10% Pd on charcoal overnight. he reaction mixture was filtered and the filtrate was concentrated. he residue was crystallized in MeOH to afford the amine.

Procedure (ii):

Triphenyl phosphine (1.3 eq) was added portion wise to a solution of the azide in dry THF and the resultant mixture was stirred at room temperature for 6 h. Water (few drops) was added and the reaction mixture was heated to 60° C. overnight. The solvent was evaporated and the residue was passed through a column of silica gel to afford the amine.

Examples 32–37 have been prepared according to the general procedure C.

| Example No. | Structure | Analytical Data |
|---|---|---|
| 32 | 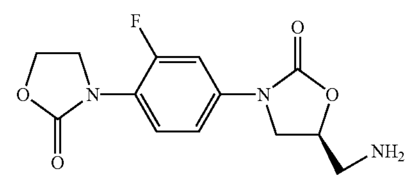 | $^1$HNMR (DMSO-D$^6$, 200MHz): δ 7.66–7.50(m, 2H), 7.37(D, j=9.4Hz, 1H), 4.66–4.60(m, 1H), 4.47(t, J=7.8Hz, 2H), 4.12–3.83(m, 6H), 2.91–2.80(m, 2H). Mp: 147° C. |
| 33 | 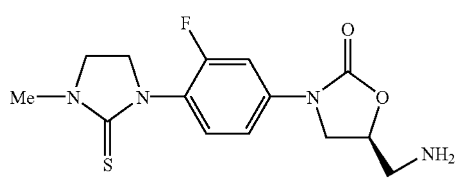 | $^1$HNMR (CDCl$_3$, 200MHz): δ 7.63–7.55(dd, J=2.0Hz and 13.0Hz, 1H), 7.49–7.22 (m, 2H), 4.63–4.60(m, 1H), 4.09(t, J=8.8Hz, 1H), 4.03–3.73(m, 4H), 3.32(m, 3H), 3.08(s, 3H). |
| 34 | 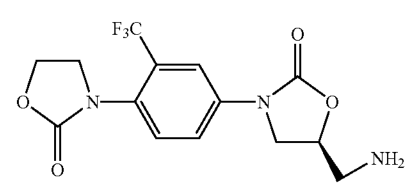 | $^1$HNMR (CDCl$_3$, 200MHz): δ 8.02(s, 2H), 7.87–7.83(m, 2H), 7.64(s, 1H), 7.50(d, J=8.2Hz, 1H), 4.84(s, 1H), 4.54(t, J=7.4Hz, 2H), 4.20–3.90(m, 6H). |
| 35 | 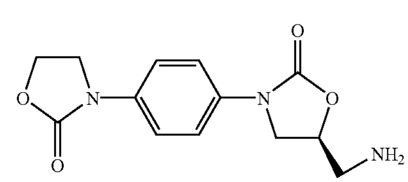 | $^1$HNMR (DMSO-d$^6$, 200MHz): δ 7.57(s, 4H), 4.63–4.61(m, 1H), 4.44(t, J=7.2Hz, 2H), 4.08–3.82(m, 4H), 2.86–2.82(m, 2H). |

-continued

| Example No. | Structure | Analytical Data |
|---|---|---|
| 36 | 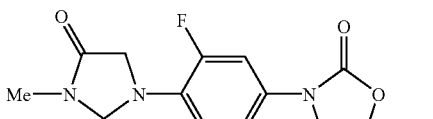 | $^1$HNMR (CDCl$_3$, 200MHz): δ 7.6–7.4(dd, 1H), 7.1(dd, 1H), 6.6(t, 1H), 4.9(s, 2H), 4.6(m, 1H), 4.1–3.7(m, 4H), 3.2–2.8(m, 4H). |
| 37 | 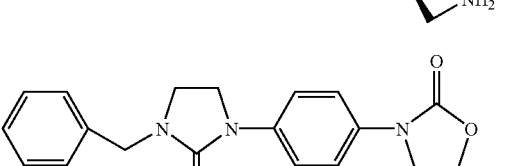 | $^1$HNMR (CDCl$_3$, 200MHz): δ 7.62–7.40(m, 3H), 7.3(s, 5H), 4.7(m, 1H), 4.5(s, 2H), 4.1(t, 1H), 3.9–3.8(m, 4H), 3.4(t, 2H). |

D. General procedure for the conversion of

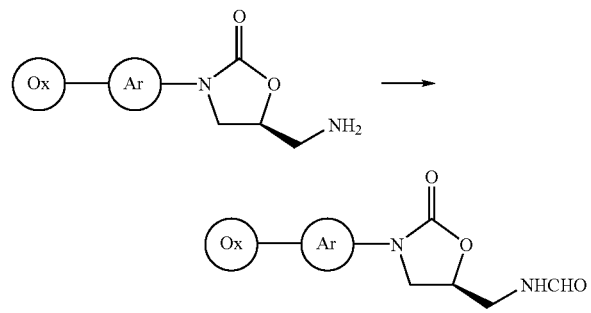

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring.

A solution of amine in methyl formate was heated to 80° C. overnight. The volatiles were removed under low pressure and the residue obtained was passed through column to yield formate in very pure form.

Examples 38 & 39 have been prepared according to the general procedure D.

| Example No. | Structure | Analytical Data |
|---|---|---|
| 38 | 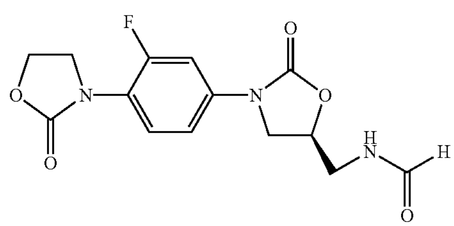 | $^1$HNMR (CDCl$_3$, 200MHz): δ 8.28(s, 1H), 7.66–7.49(m, 2H), 7.15(d, J=8.8Hz, 1H), 6.15(bs, 1H), 4.82(m, 1H), 4.52(t, J=7.4Hz, 2H), 4.48–4.02(m, 3H). |
| 39 | 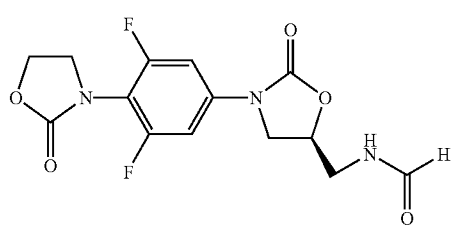 | $^1$HNMR (CDCl$_3$, 200MHz): δ 8.27(s, 1H), 7.26–7.23(m, 2H), 6.32(bs, 1H), 4.82(bs, 1H), 4.58(t, J=7.2Hz, 2H), 4.214–3.68 (m, 6H). |

E. General procedure for the conversion of

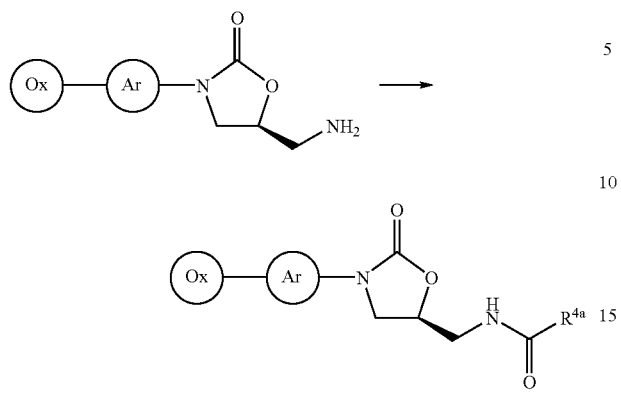

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring and $R^{4a}$ represents $(C_1-C_6)$alkyl, $(C_1-C_6)$alkoxy, $(C_2-C_6)$alkenyl, halo$(C_1-C_6)$alkyl, aryloxy, $(C_2-C_6)$alkenyloxy, aryloxycarbonyl or $(C_1-C_6)$alkoxycarbonyl.

To a solution of the amine (1 eq) in dry dichloromethane at 0° C. under argon was added $Et_3N$ (2.5 eq) followed by respective acid chloride (1.2 eq) drop wise. After being stirred at room temperature for 1 to 6 h (TLC control), the reaction mixture was diluted with dichloromethane and washed with water twice followed by brine. The organic extract was dried, evaporated and was passed through column to afford the acylated product.

Examples 40–70 have been prepared according to the general procedure E.

| Example No. | Structure | Analytical Data |
|---|---|---|
| 40 | 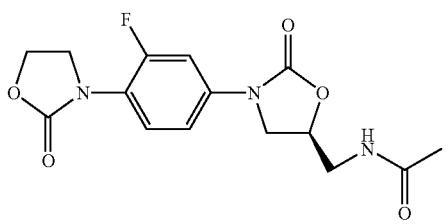 | $^1$HNMR (CDCl$_3$, 200MHz): δ 7.62(dd, J=2.60Hz and 13.4 Hz, 1H), 7.52(d, J=8.60Hz, 1H), 7.13–7.17(m, 1H), 5.96–5.99(m, 1H), 4.82–4.76(m, 1H), 4.52(t, J=7.40Hz, 2H), 4.01–4.09(m, 3H), 3.62–3.81 (m, 3H), 2.02(s, 3H). |
| 41 | 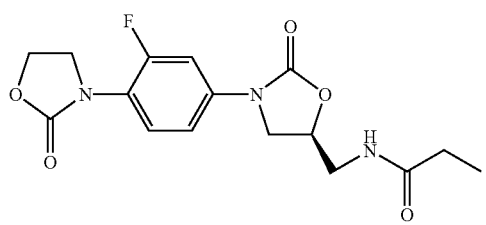 | $^1$HNMR (CDCl$_3$, 200MHz): δ 7.66–7.49(m, 2H), 7.16(d, J=8.8Hz, 1H), 6.03(bs, 1H), 4.82–4.78(m, 1H), 4.52(t, J=7.8Hz, 2H), 4.09–4.0(m, 3H), 3.83–3.65(m, 3H), 2.24(q, J=7.8Hz, 2H), 1.13(t, J=7.8 Hz, 3H). Mp: 203° C. |
| 42 | 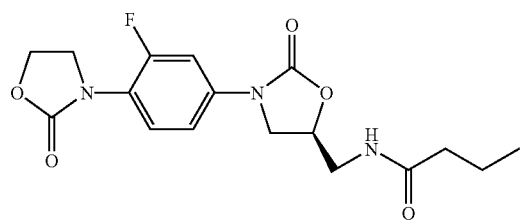 | $^1$HNMR (CDCl$_3$, 200MHz): δ 7.66–7.49(m, 2H), 7.15(d, J=8.8Hz, 1H), 6.01(bs, 1H), 4.81–4.75(m, 1H), 4.52(t, J=7.8Hz, 2H), 4.09–4.01(m, 3H), 3.83–3.65(m, 3H), 2.19 (t, J=7.4Hz, 2H), 1.65–1.58 (m, 2H), 0.98(t, J=7.4Hz, 3H). Mp: 211° C. |
| 43 | 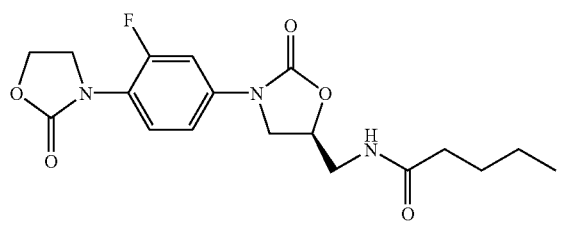 | $^1$HNMR (CDCl$_3$, 200MHz): δ 7.66–7.49(m, 2H), 7.15(d, J=8.8Hz, 1H), 4.82–4.76(m, 1H), 4.52(t, J=7.8Hz, 2H), 4.09–4.01(m, 2H), 3.83–=3.65 (m, 3H), 2.21(t, J=7.4Hz, 2H), 1.57–1.49(m, 2H), 1.38–1.20(m, 2H), 0.89(t, 3H). Mp: 187° C. |

-continued

| Example No. | Structure | Analytical Data |
|---|---|---|
| 44 | 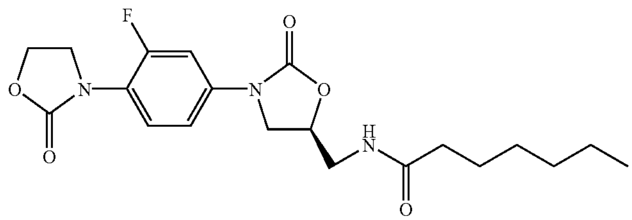 | $^1$HNMR (CDCl$_3$, 200MHz): δ 7.68–7.52(m, 2H), 7.17(d, 8.6Hz, 1H), 5.96(hump, 1H), 4.81(hump, 1H), 4.54(t, J=7.2Hz, 2H), 4.11–3.67(m, 6H), 2.22(t, J=7.4Hz, 2H), 1.60(bs, 8H), 0.87(s, 3H). Mp: 131° C. |
| 45 | 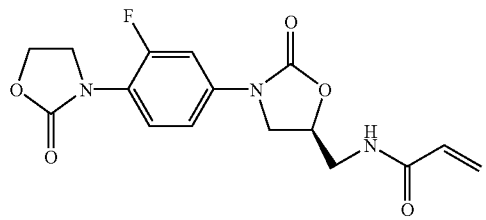 | $^1$HNMR (CDCl$_3$+DMSO-d$^6$, 200MHz): δ 7.97(bs, 1H), 7.6–7.40(m, 2H), 7.10(d, J=8.8Hz, 1H), 6.35–6.15(m, 2H), 5.63(dd, J=4.0Hz and 8.3Hz, 1H), 4.79–4.86(m, 1H), 4.53(t, J=7.8Hz, 2H), 4.05(t, J=6.8Hz, 2H), 3.89–3.56(m, 4H). Mp: 196° C. |
| 46 | 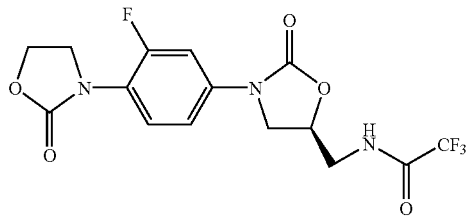 | $^1$HNMR (CDCl$_3$+DMSO-d$^6$, 200MHz): δ 9.38(bs, 1H) 7.67–7.5(m, 2H), 7.20(d, J=8.8Hz, 1H), 4.88–4.87(m, 1H), 4.53(t, J=7.8Hz, 2H), 4.16–4.02(m, 3H), 3.89–3.70 (m, 1H), 3.67–3.65(m, 2H). Mp: 194° C. |
| 47 | 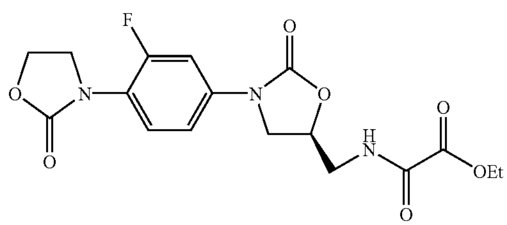 | $^1$HNMR (CDCl$_3$, 200MHz): δ 7.66–7.49(m, 2H), 7.15(d, J=8.8Hz, 1H), 4.85–4.83(m, 1H), 5.55–4.47(m, 2H), 4.37–4.31(m, 2H), 4.14–3.90(m, 3H), 3.88–3.60(m, 3H), 1.42 (t, 3H). Mp: 160° C. |
| 48 | 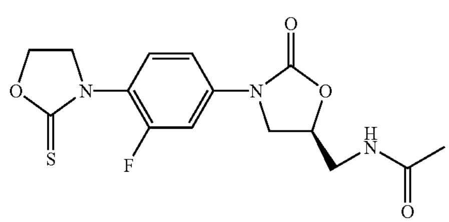 | $^1$HNMR (CDCl$_3$, 200MHz): δ 7.75–7.05(m, 3H), 6.05(bs, 1H), 4.95–4.62(m 2H), 4.52 (t, 1H), 4.30–3.32(m, 6H), 2.023(s, 3H). |
| 49 | 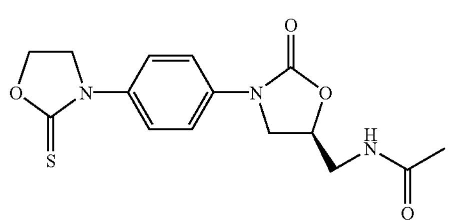 | $^1$HNMR (CDCl$_3$, 200MHz): δ 7.5(d, J=7.81Hz, 2H), 7.3 (d, J=7.81Hz, 2e H), 4.8(s, 1H), 4.4(s, 4H), 4.1(t, 1H), 3.8(t, 1H), 3.5(s, 1H), 32.3 (s, 1H), 2.0(s, 3H). |

-continued

| Example No. | Structure | Analytical Data |
| --- | --- | --- |
| 50 | 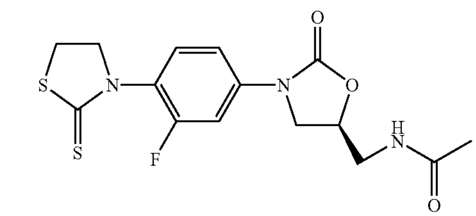 | ¹HNMR (CDCl₃, 200MHz): δ 7.99(hump, 1H), 7./73(d, J=13.0Hz, 1H), 7.43(d, J=8.0Hz, 1H) 7.31(d, J=8.8Hz, 1H), 4.83(hump, 1H), 4.42(t, J=7.6Hz, 2H), 4.15–3.89(m, 3H), 3.62–3.55(m, 4H), 2.0(s, 3H). Mp: 220° C. |
| 51 | 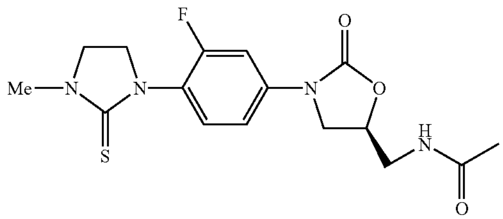 | ¹HNMR (CDCl₃, 200MHz): δ 7.61(dd, J=2.6Hz and 12.7 Hz, 1H), 7.48(t, J=8.4Hz, 1H), 7.19(dd, J=2.6Hz and 8.8Hz, 1H), 6.15(t, J=8.4 Hz, 1H), 4.79–4.77(m, 1H), 4.05(t, J=8.8Hz, 1H), 3.97–3.88(m, 2H), 3.81–3.74(m, 3H), 3.69–3.61(m, 2H), 3.23 (s, 3H), 2.03(s, 3H). Mp: 171° C. |
| 52 | 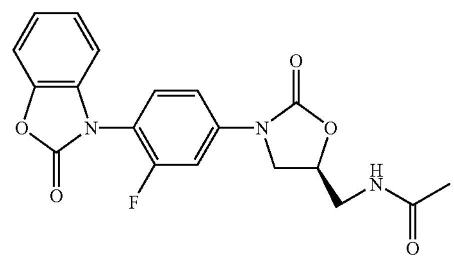 | ¹HNMR (CDCl₃, 200MHz): δ 7.76(dd, J=2.2Hz and 12.0 Hz, 1H), 7.53(t, J=8.4Hz, 1H), 7.37–7.14(m, 4H), 6.82 (t, J=3.4Hz, 1H), 6.03(t, J=5.4Hz, 1H), 4.83–4.80(m, 1H), 4.10(t, J=9.0Hz, 1H), 3.88–3.80(m, 1H), 3.71–3.66 (m, 2H), 2.04(s, 3H). |
| 53 | 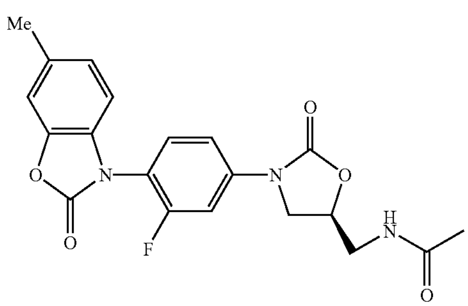 | ¹HNMR (CDCl₃, 200MHz): δ 7.74(dd, J=2.6Hz and 12.2Hz, 1H), 7.53(t, J=8.4 Hz, 1H), 7.49–7.26(m, 2H), 7.10–6.95(m, 2H), 6.72–6.68 (m, 1H), 6.09–6.01(m, 1H), 4.84(bs, 1H), 4.10(t, J=8.8 Hz, 1H), 3.88–3.66(m, 3H), 2.41(s, 3H), 2.04(s, 3H). Mp: 213° C. |
| 54 | 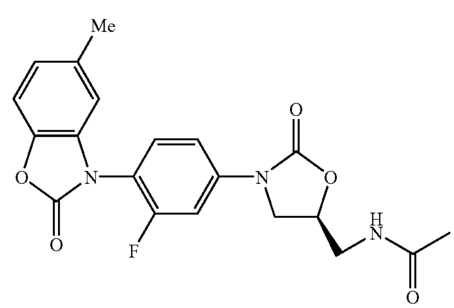 | ¹HNMR (CDCl₃, 200MHz): δ 7.80–6.94(m, 4H), 6.63(s, 1H), 6.0(bs, 1H), 4.82–4.90 (m, 1H), 4.11(t, J=9.2Hz, 1H), 3.89–3.66(m, 3H), 2.35 (s, 3H), 2.09(s, 3H). Mp: 202° C. |
| 55 | 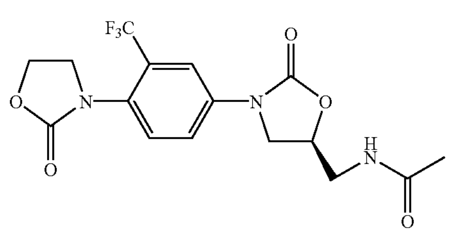 | ¹HNMR (CDCl₃, 200MHz): δ 7.93(s, 1H), 7.76(d, J=8.8 Hz, 1H), 7.42(d, J=8.8Hz, 1H), 6.57(bs, 1H), 4.79(bs, 1H), 4.52(t, J=7.8Hz, 2H), 4.11–3.60(m, 6H), 1.99(s, 3H). Mp: 143° C. |

-continued

| Example No. | Structure | Analytical Data |
|---|---|---|
| 56 | 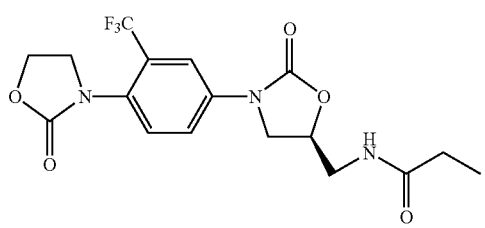 | ¹HNMR (CDCl₃, 200MHz): δ 7.93–7.79(m, 2H), 7.43(d, J=8.8Hz, 1H), 6.12(bs, 1H), 4.82–4.78(m, 1H), 4.53(t, J=7.4Hz, 2H), 4.09(t, J=9.4 Hz, 1H), 3.96–3.66(m, 5H), 2.30–2.17(m, 2H), 1.20(t, J=9.4Hz, 3H). Mp: 143° C. |
| 57 | 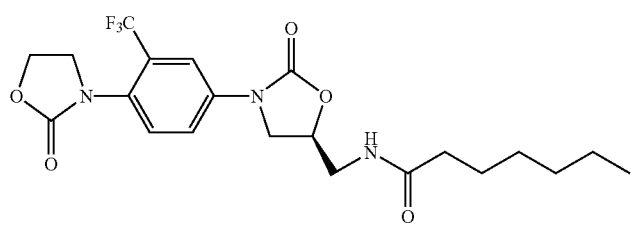 | ¹HNMR (CDCl₃, 200MHz): δ 7.91(s, 1H), 7.78(d, J=8.2 Hz, 1H), 6.26(bs, 1H), 4.80 (bs, 1H), 4.52(t, J=7.2Hz, 2H), 4.06(t, J=9.4Hz, 1H), 3.95–3.67(m, 5H), 2.47–2.05 (m, 4H), 1.83–1.54(m, 6H), 0.83–0.78(m, 3H). Mp: hygroscopic |
| 58 | 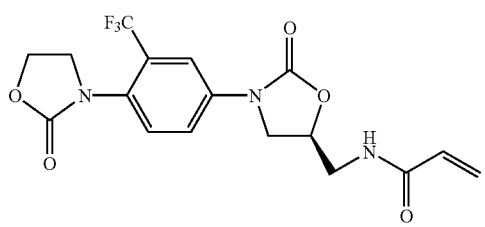 | ¹HNMR (CDCl₃, 200MHz): δ 7.92(s, 1H), 7.85(d, J=8.2 Hz, 1H), 7.45(d, J=8.8Hz, 1H), 6.40–6.07(m, 3H), 5.75 (d, J=10.4Hz, 1H), 4.89 (hump, 1H), 4.56(t, J=7.8 Hz, 2H), 4.13(t, J=9.2Hz, 1H), 3.98–3.78(m, 5H). Mp: 191° C. |
| 59 | 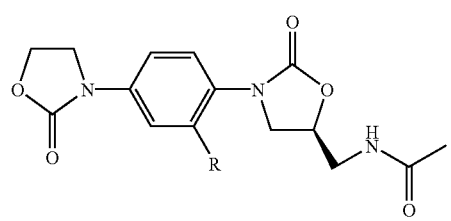 | ¹HNMR (CDCl₃, 200MHz): δ 7.65–7.41(m, 2H), 7.23(d, J=7.2Hz, 1H), 6.12(bs, 1H), 4.80(bs, 1H), 4.52(t, J=7.8 Hz, 2H), 4.47–4.00(m, 3H), 3.81–3.59(m, 3H), 2.05(s, 3H). Mp: 120° C. |
| 60 | 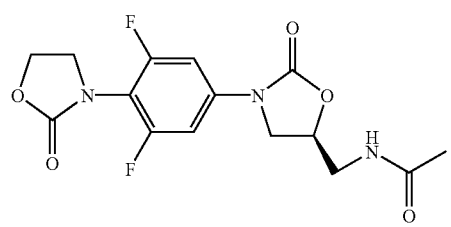 | ¹HNMR (CDCl₃, 200MHz): δ 7.27(d, J=9.8Hz, 2H), 6.01 (hump, 1H), 4.80(hump, 1H), 4.57(t, J=7.8Hz, 2H), 4.06–3.67(m, 6H), 2.03(s, 3H). Mp: 219° C. |
| 61 | 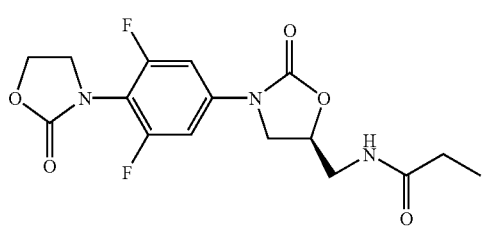 | ¹HNMR (CDCl₃+DMSO-d⁶, 200MHz): δ 7.32–7.26(m, 2H), 7.09(hump, 1H), 4.81 (hump, 1H), 4.58(t, J=7.4 Hz, 2H), 4.05–3.62(m, 6H), 2.25–2.18(m, 2H), 1.11(t, J=7.8Hz, 3H). Mp: 224° C. |

| Example No. | Structure | Analytical Data |
|---|---|---|
| 62 | 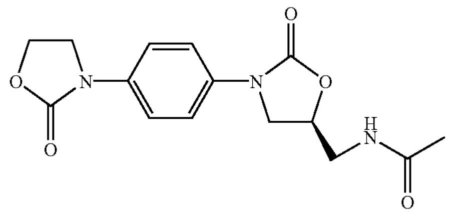 | ¹HNMR (CDCl₃+DMSO-d6, 200MHz): δ 7.64(s, 2H), 7.55 (s, 2H), 7.09–7.25(m, 1H), 4.70–4.85(m, 1H), 4.46(t, 2H), 4.13–3.81(m, 4H), 3.57 (bs, 2H), 1.96(s, 3H). Mp: 231° C. |
| 63 | 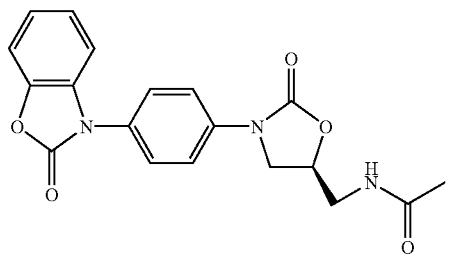 | ¹HNMR (CDCl₃, 200MHz): δ 7.70(d, J=8.8Hz, 2H), 7.54 (d, J=8.8Hz, 2H), 7.24–6.99 (m, 4H), 6.19(bs, 1H), 4.80 (m, 1H), 4.09(t, J=8.8Hz, 1H), 3.85(t, J=7.0Hz, 1H), 3.69–3.63(m, 2H), 2.02(s, 3H). Mp: 229° C. |
| 64 | 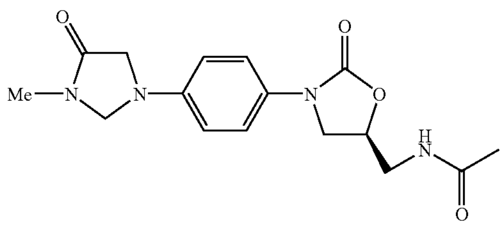 | ¹HNMR (CDCl₃, 200MHz): δ 7.10(d, 1H), 6.6(t, 1H), 6.0 (m, 1H), 4.90(s, 2H), 4.9(m, 1H), 4.0(s, 3H), 3.80(m, 3H), 3.0(s, 3H), 2.0(s, 3H). Mp: 230° C. |
| 65 | 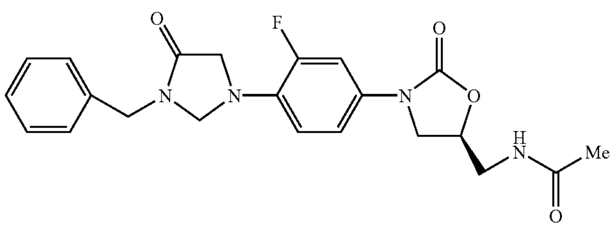 | ¹HNMR (CDCl₃, 200MHz): δ 7.26–7.46(m, 6H), 7.01(d, 1H), 6.63(t, 1H), 6.05(s, 1H), 4.71–4.89(m, 2H), 4.77(s, 1H), 4.60(s, 2H), 3.94–4.04 (m, 3H), 3.61–3.76(m, 3H), 2.01(s, 3H). |
| 66 | 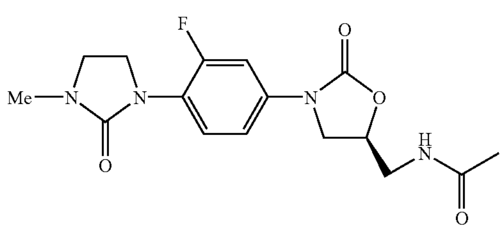 | ¹HNMR (CDCl₃, 200MHz): δ 7.50(m, 2H), 7.10(d, J=8.4 Hz, 1H), 6.18(t, 1H), 4.7(m, 1H), 4.0(t, J=9.4Hz, 1H), 3.6(m, 7H), 2.9(s, 3H), 2.0 (s, 3H). Mp: 182° C. |
| 67 | 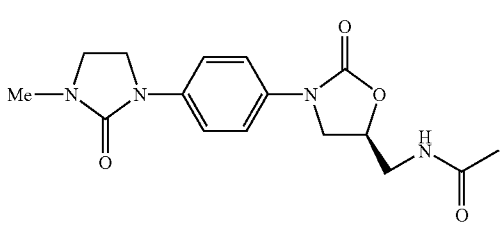 | ¹HNMR (CDCl₃, 200MHz): δ 2.0(s, 3H), 2.8(s, 3H), 4.0(t, 1H), 3.4–3.8(m, 5H), 4.8(m, 1H), 6.2(m, 1H), 7.6(m, 4H). Mp: 217° C. |

| Example No. | Structure | Analytical Data |
|---|---|---|
| 68 | 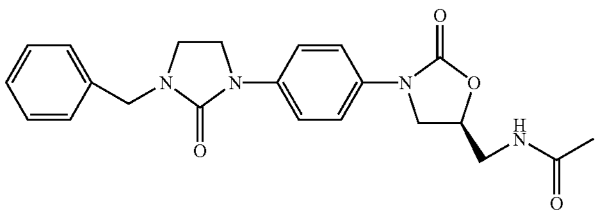 | ¹HNMR (CDCl₃, 200MHz): δ 7.6–7.3(m, 9H), 6.2(bt, 1H), 4.8–4.7(m, 1H), 4.5(s, 2H), 4.06(t, J=9.3Hz, 1H), 3.90–3.3(m, 6H), 2.0(s, 3H). Mp: 204° C. |
| 69 | 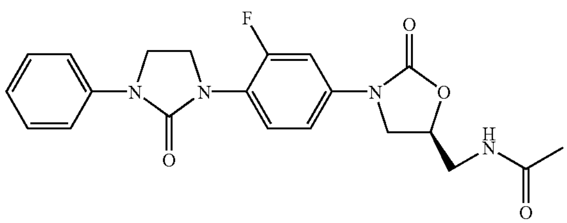 | ¹HNMR (CDCl₃, 200MHz): δ 7.70–7.50(m, 4H), 7.40–7.30 (t, 2H), 7.2(d, J=8.8Hz, 1H), 7.1(t, 1H), 4.80(m, 5H), 4.0(m, 5H), 3.8(m, 1H), 3.6 (m, 2H), 2.0(s, 3H). Mp: 182° C. |
| 70 | 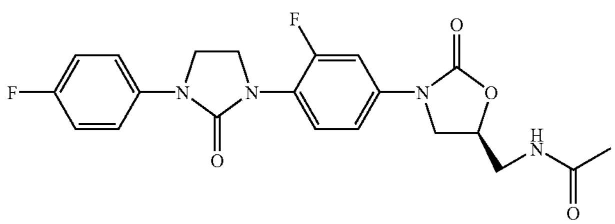 | ¹HNMR (CDCl₃, 200MHz): δ 8.3(m, 1H), 7.6(m, 4H), 7.3 (m, 1H), 7.2(t, 2H), 4.7(m, 1H), 4.1(t, 1H), 3.8–4.0(m, 4H), 3.7(t, 1H), 3.0(m, 2H), 1.8(s, 3H). Mp: 194° C. |

F. General procedure for the conversion of

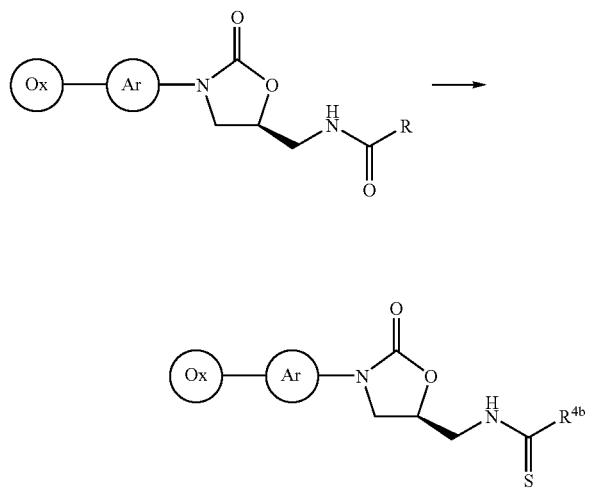

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring and $R^{4b}$ represents $(C_1-C_6)$alkyl, halo$(C_1-C_6)$alkyl, —C(=O)—$(C_1-C_6)$alkoxy, —C(=O)-aryloxy, —C(=S)—$(C_1-C_6)$ alkyl or —C(=S)-aryl.

A solution of the amide (1 eq) and Lawesson's reagent (0.6 eq) in dry dioxane was heated to 55 to 90° C. over 3 to 10 h (TLC control). The reaction mixture was allowed to cool to room temperature and diluted with ethyl acetate. The resultant mixture was washed with water (4 times) followed by brine and dried. The residue obtained upon evaporation of solvent was passed through column of silica gel to afford the respective thioacetate.

Examples 71–80 have been prepared according to the general procedure F

| Example No. | Structure | Analytical Data |
|---|---|---|
| 71 | 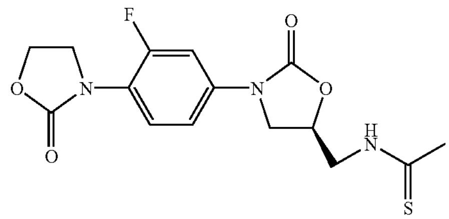 | ¹HNMR (CDCl₃, 200MHz): δ 7.94(bs, 1H), 7.66–7.52(m, 2H), 7.16(d, J=7.8Hz, 1H), 5.20–4.85 (m, 1H), 4.54(t, J=7.8 Hz, 2H), 4.25–3.82(m, 6H), 2.61(s, 3H). Mp: 171° C. |
| 72 | 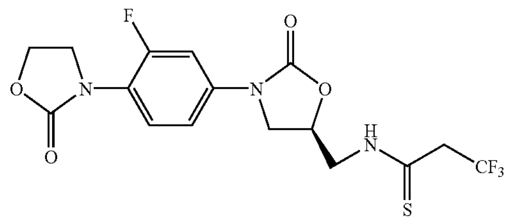 | ¹HNMR (CDCl₃+DMSO-d6, 200MHz): δ 10.51(s, 1H), 7.64–7.47(m, 2H), 7.16(d, J=8.8Hz, 1H), 5.01(bs, 1H), 4.53(t, J= 7.2Hz, 2H), 4.29–3.89(m, 4H), 3.63(q, J=10.2Hz, 2H). Mp: 165° C. |
| 73 | 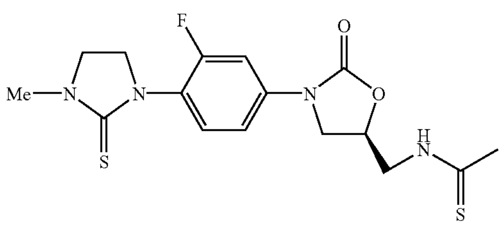 | ¹HNMR (CDCl₃, 200MHz): δ 7.90(bs, 1H), 7.61(dd, J=2.4Hz and 12.8Hz, 1H), 7.50(t, J= 8.2Hz, 1H), 7.19(dd, J= 2.4Hz and 12.8Hz, 1H), 5.0(m, 1H), 4.25–3.74(m, 8H), 3.24(s, 3H), 2.6(s, 3H). Mp: 111° C. |
| 74 | 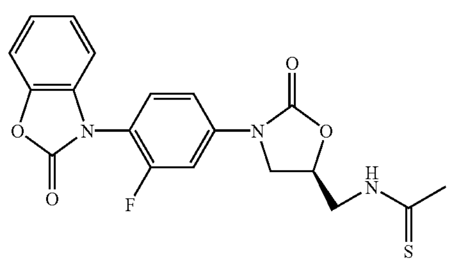 | ¹HNMR (CDCl₃, 200MHz): δ 7.87–7.74(m, 2H), 7.57(t, J=8.2Hz, 1H), 7.39–7.18(m, 4H), 6.87–6.85(m, 1H), 5.08–5.05(m, 1H), 4.37–4.27 (m, 1H), 4.23–4.06(m, 2H), 3.94(t, J=6.8Hz, 1H), 2.62(s, 3H). Mp: 137° C. |
| 75 | 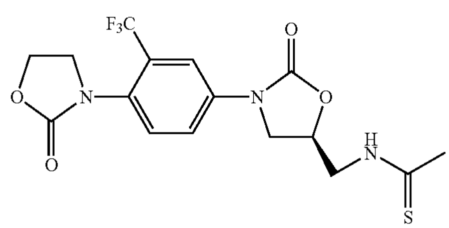 | ¹HNMR (CDCl₃, 200MHz): δ 8.1(s, 1H), 7.9(s, 1H), 7.8(d, J=8.7 Hz, 1H), 7.4(d, J=8.79, 1H), 5.0(s, 1H), 4.6(t, 2H), 4.0(m, 6H), 2.6(s, 3H). Mp: 154° C. |
| 76 | 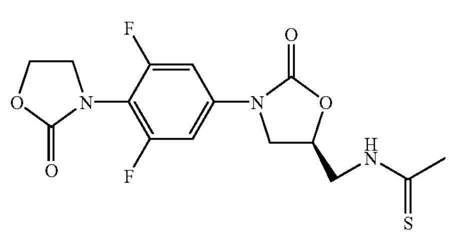 | ¹HNMR (CDCl₃+DMSO-d⁶, 200MHz): δ 10.37(bs, 1H), 7.50(d, J=10.8Hz, 2H), 4.98(bs, 1H), 4.55(t, J=7.8Hz, 2H), 4.23–3.78 (m, 6H), 2.50(s, 3H). Mp: 108° C. |

| Example No. | Structure | Analytical Data |
|---|---|---|
| 77 | 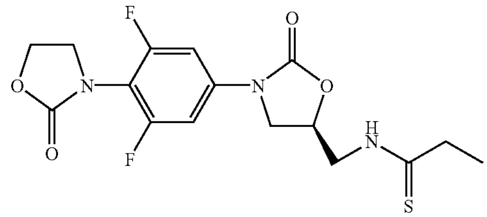 | ¹HNMR (CDCl₃, 200MHz): δ 7.86(bt, 1H), 7.28(d, J=9.6Hz, 2H), 5.02–4.99(m, 1H), 4.58(t, J=7.4Hz, 2H), 4.24–3.80 (m, 6H), 2.71(q, J=7.4Hz, 2H), 1.29(t, J=7.8Hz, 3H). Mp: 168° C. |
| 78 | 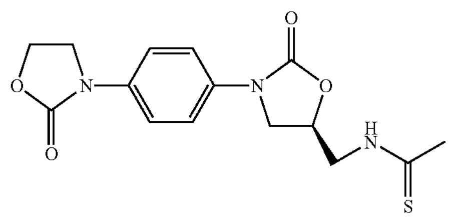 | ¹HNMR (CDCl₃, 200MHz): δ 7.86(hump, 1H), 7.25(d, J=9.6Hz, 2H), 5.02–4.99(m, 1H), 4.58(t, J=7.4Hz, 2H), 4.24–3.80(m, 6H), 2.71(q, J=7.4Hz, 2H), 1.29(t, J= 7.8Hz, 3H). Mp: 195° C. |
| 79 | 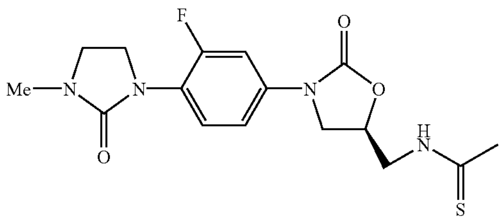 | ¹HNMR (CDCl₃, 200MHz): δ 8.4(1H), 7.5 (m, 2H), 7.0(d, J=8.8Hz, 2H), 4.9(m, 1H), 3.9(m, 6H), 3.5(t, J=8.8Hz, 2H), 2.9(s, 3H), 2.5(s, 3H). Mp: 168° C. |
| 80 | 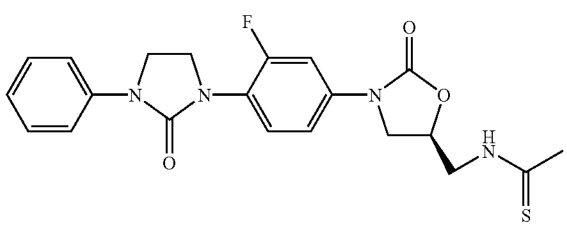 | ¹HNMR (CDCl₃, 200MHz): δ 7.6(m, 4H), 7.4(m, 2H), 7.2(d, J=8.8 Hz, 1H), 7.0(t, 1H), 5.0 (m, 1H), 4.0(m, 8H), 2.6 (s, 3H). Mp: 165° C. |

G. General procedure for the conversion of

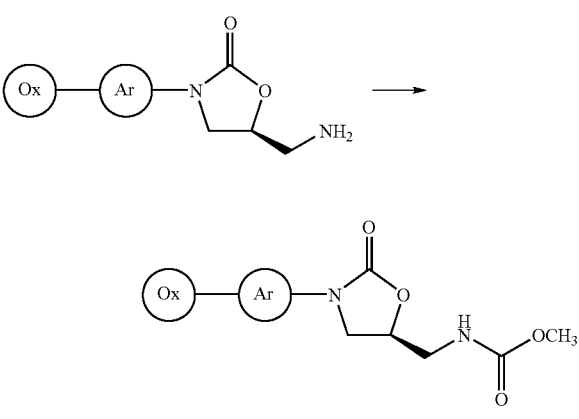

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring.

To a solution of the amine (1 eq), Et₃N (2.2 eq) in dry dichloromethane methyl chloroformate under argon was added at 0° C. (1.2 eq). The reaction mixture was stirred at room temperature overnight and worked up by diluting with dichloromethane followed by washing with water and brine. The residue obtained after evaporation of the dried organic layer was passed through column to afford the carbamate.

Examples 81–85 have been prepared according to the general procedure G

| Example No. | Structure | Analytical Data |
|---|---|---|
| 81 | 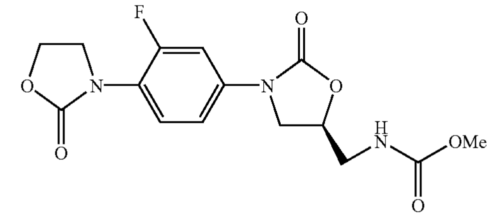 | ¹HNMR (CDCl₃, 200MHz): δ 7.68–7.49(m, 2H), 7.16(d, J=8.4Hz, 1H), 5.16(bs, 1H), 4.78(bs, 1H), 4.52(t, J=7.2Hz, 2H), 4.09–4.0(m, 3H), 3.84–3.55(m, 6H). Mp: 153° C. |
| 82 | 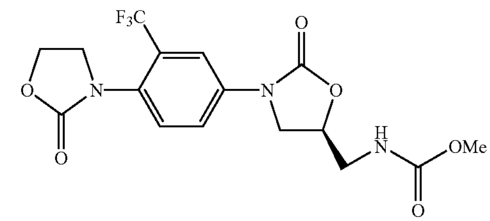 | ¹HNMR (CDCl₃, 200MHz): δ 7.9(m, 2H), 7.4(d, J=8.3 Hz, 1H), 5.2(s, 1H), 4.8(s, 1H), 4.5(t, 1H), 4.0(m, 9H). Mp: 148° C. |
| 83 | 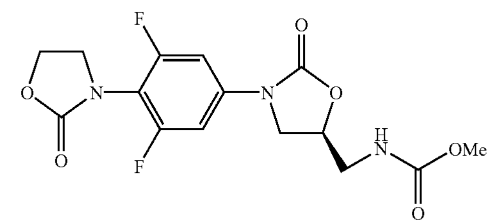 | ¹HNMR (CDCl₃, 200MHz): δ 7.27(d, J=6.8Hz, 2H), 5.16(bs, 1H), 4.84–4.80(m, 1H), 4.58(t, J=7.2Hz, 2H), 4.07–3.60(m, 9H). Mp: 157° C. |
| 84 | 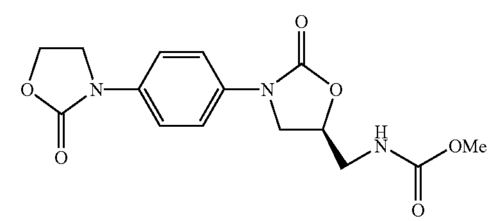 | ¹HNMR (CDCl₃+DMSO-d⁶, 200MHz): δ 7.57(s, 4H), 6.98(bs, 1H), 4.96–4.76(m, 1H), 4.51(t, J=7.4Hz, 2H), 4.47(m, 3H), 3.91–3.84(m, 1H), 3.65(s, 1H), 3.51(bs, 3H). Mp: 195° C. |
| 85 | 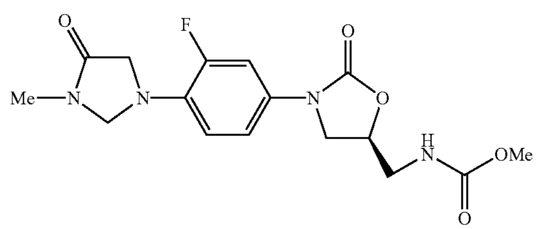 | ¹HNMR (CDCl₃, 200MHz): δ 3.0(s, 3H), 3.8(m, 6H), 4.8(m, 1H), 4.9(s, 2H), 5.1 (m, 1H), 6.6(t, 1H). Mp: 226° C. |

H. General procedure for the conversion of

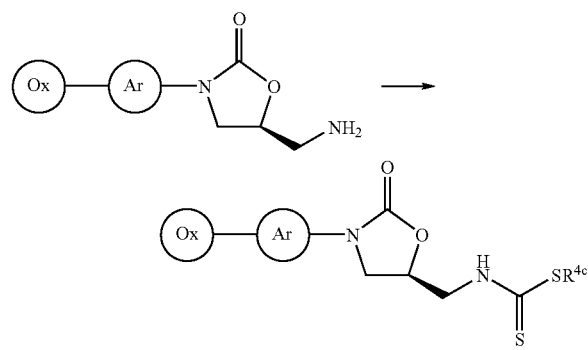

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring and $R^{4c}$ represents $(C_1-C_6)$alkyl group.

To an ice cold mixture of amine (1 eq), Et₃N (2 eq) and water (few drops) in EtOH CS₂ (1 eq) was added under argon. Stirred overnight at room temperature, Methyl iodide (MeI) (1.1 eq) in EtOH was added and the stirring was continued for 12 h. The volatiles were removed and the residue was taken up in ethyl acetate. The organic mixture was washed with saturated NaHCO$_3$, water, brine and dried. The residue obtained was passed through column to afford the product.

Examples 86 and 87 have been prepared according to the general procedure H.

| Example No. | Structure | Analytical Data |
|---|---|---|
| 86 | 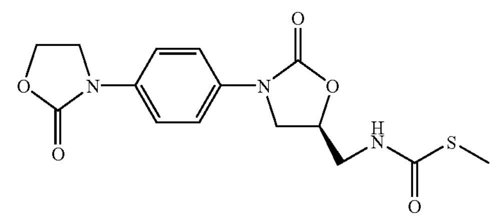 | $^1$HNMR (CDCl$_3$+DMSO-d6, 200MHz): δ 9.98(bt, 1H), 7.55(s, 4H), 5.05–5.02(m, 1H), 4.50(t, J=7.8Hz, 2H), 4.12–3.87(m, 6H), 2.60(s, 3H). Mp: 161° C. |
| 87 | 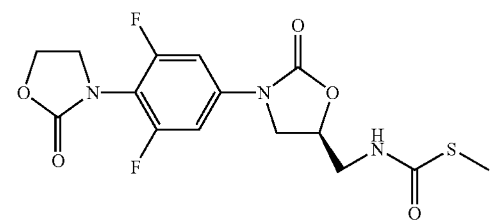 | $^1$HNMR (DMSO-d6, 200MHz): δ 7.26(s, 1H), 6.15 (d, J=10.2Hz, 2H), 4.56–4.49(m, 3H), 4.27–3.83(m, 5H), 3.26–3.15(m, 1H), 2.54 (s, 3H). Mp: 147° C. |

I. General procedure for the conversion of
Step (i):

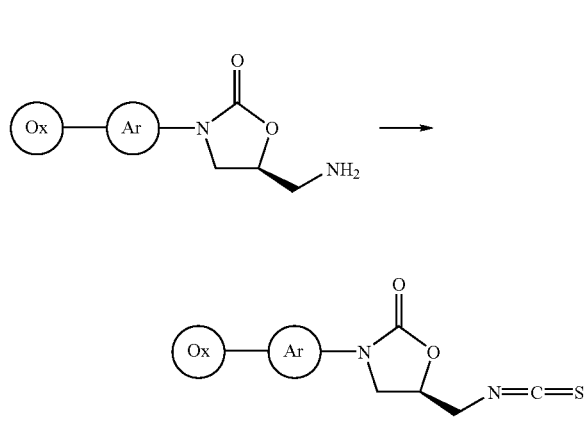

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring.

Thiophosgene (1.2 eq) was added drop wise to a solution of the amine (1 eq), Et$_3$N (2.4 eq) in dry dichloromethane at ice bath temperature under argon. The reaction mixture was warmed to room temperature over 3 h and then the volatiles were removed. The residue obtained was directly charged on to a column of silica gel to afford the product.

Step (ii):

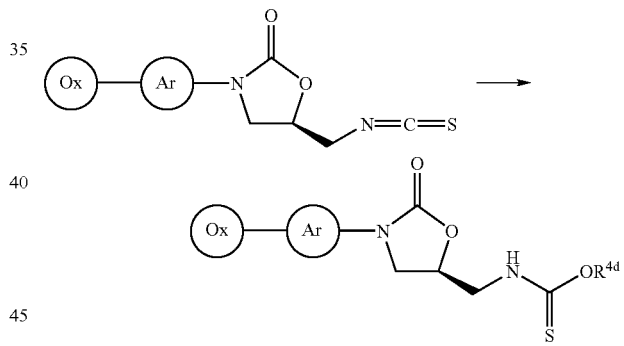

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring and R$^{4d}$ represents (C$_1$–C$_6$)alkyl, cyclo(C$_3$–C$_6$)alkyl, —(C=O)—(C$_1$–C$_6$)alkyl group substituted with fluorine; aryl, halo (C$_1$–C$_6$)alkyl, hydroxy(C$_1$–C$_6$)alkyl, (C$_1$–C$_6$)alkoxy (C$_1$–C$_6$)alkyl or (C$_2$–C$_6$)alkenyl.

A solution of the isothiocyanate in the respective alcohol was heated to 80 to 100° C. while monitoring by TLC. At the complete consumption of starting material, the reaction mixture was allowed to cool to room temperature. The crystals formed were separated, washed with ether and dried at vacuum to yield the pure product.

Examples 88–124 have been prepared according to the general procedure I

| Example No. | Structure | Analytical Data |
|---|---|---|
| 88 | 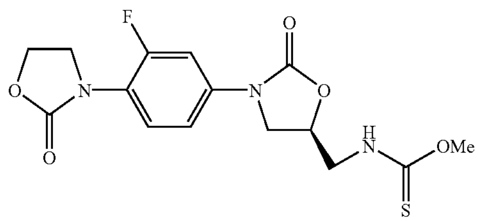 | ¹HNMR (CDCl₃, 200MHz): δ 7.67–7.56(m, 2H), 7.16(d, J=2.0Hz, 1H), 6.72(bs, 1H), 4.94(bs, 1H), 4.52(t, J=7.8 Hz, 2H), 4.12–3.83(m, 9H). Mp: 137° C. |
| 89 | 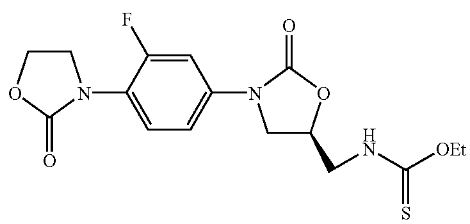 | ¹HNMR (CDCl₃, 200MHz): δ 7.66–7.50(m, 2H), 7.15(d, J=7.4Hz, 1H), 6.66(hump, 1H), 4.94(bs, 1H), 4.56–4.43(m, 4H), 4.12–3.84(m, 6H), 1.32 (t, J=6.8Hz, 3H). Mp: 208° C. |
| 90 | 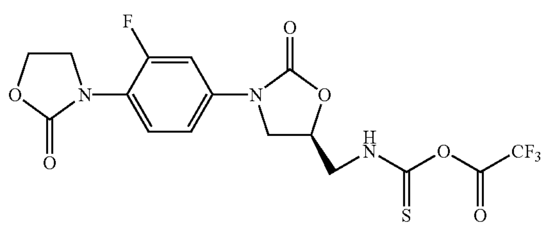 | ¹HNMR (CDCl₃+DMSO-d⁶, 200MHz): δ 8.45(bs, 1H), 7.65–7.46(m, 2H), 7.17(d, J=8.8Hz, 1H), 4.81(bs, 1H), 4.53(t, J=7.4Hz, 2H), 4.09–3.99(m, 3H), 3.84–3.55(m, 3H), 3.13(q, J=10.4Hz, 2H). Mp: 184° C. |
| 91 | 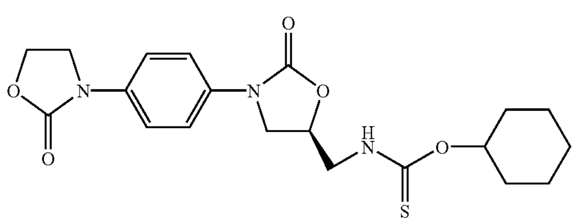 | ¹HNMR (DMSO-d⁶, 200MHz): δ 9.54(m, 1H), 7.57(s, 4H), 4.90–4.80(m, 2H), 4.44(t, J=7.4Hz, 2H), 4.21–4.01(m, 4H), 3.88–3.77 (m, 3H), 3.56–3.53(m, 1H), 1.23–0.97(m, 6H). Mp: 153° C. |
| 92 | 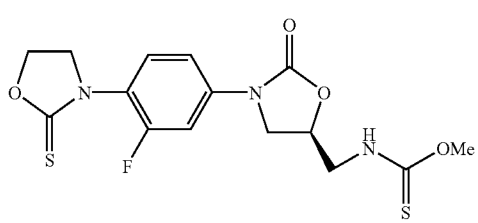 | ¹HNMR (CDCl₃, 200MHz): δ 8.2(m, 1H), 7.7(d, J=10.74 Hz, 1H), 7.5(t, 1H), 7.3(d, J=8.79Hz, 1H), 5.0(m, 1H), 4.70(t, 2H), 4.1(m, 9H). Mp: 197° C. |
| 93 | 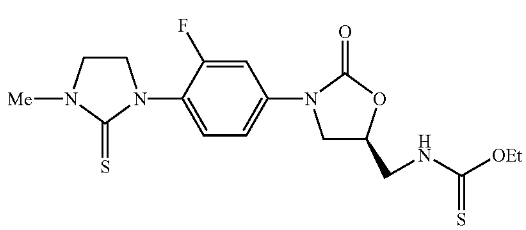 | ¹HNMR (CDCl₃, 200MHz): δ 7.02(dd, J=2.4Hz and 12.8 Hz, 1H), 7.49(t, J=8.8Hz and 12.8Hz, 1H), 7.20(dd, J=2.4Hz and 12.8Hz, 1H), 6.63(bs, 1H), 4.93(m, 1H), 4.54–4.44(q, J=7.4Hz, 2H), 4.13–3.72(m, 8H), 3.24(s, 3H), 1.32(t, J=7.0Hz, 3H). Mp: 197° C. |

-continued

| Example No. | Structure | Analytical Data |
|---|---|---|
| 94 | 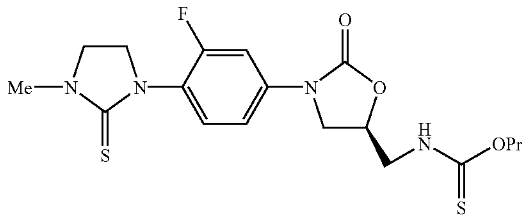 | ¹HNMR (CDCl₃, 200MHz): δ 7.62(dd, J=2.4Hz and 12.6 Hz, 1H), 7.49(t, J=8.8Hz, 1H), 7.20(dd, J=2.4Hz and 12.6Hz, 1H), 6.65(bs, 1H), 4.94(m, 1H), 4.38(t, J=8.8 Hz, 2H), 4.13–3.73(m, 8H), 3.24(s, 3H), 1.78–1.63(m, 2H), 0.99(t, 3H). Mp: >200° C. |
| 95 | 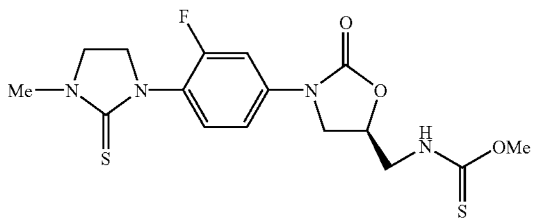 | ¹HNMR (CDCl₃, 200MHz): δ 7.62(dd, J=2.4Hz and 12.7 Hz, 1H), 7.49(t, J=8.8Hz, 1H), 7.20(dd, J=2.4Hz and 12.7Hz, 1H), 6.70(bs, 1H), 4.94(m, 1H), 4.13–3.72(m, 11H), 3.24(s, 3H). Mp: 179° C. |
| 96 | 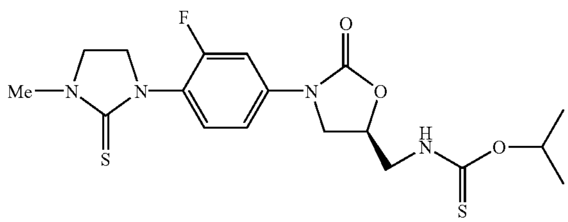 | ¹HNMR (CDCl₃, 200MHz): δ 7.62(dd, J=2.4Hz and 12.7 Hz, 1H), 7.49(t, J=8.8Hz, 1H), 7.20(dd, J=2.4Hz and 13.0Hz, 1H), 6.55(bs, 1H), 5.58–5.49(heptet, 1H), 4.92 (m, 1H), 4.13–3.73(m, 8H), 3.24(s, 3H), 1.39–1.25(m, 6H). Mp: 183° C. |
| 97 | 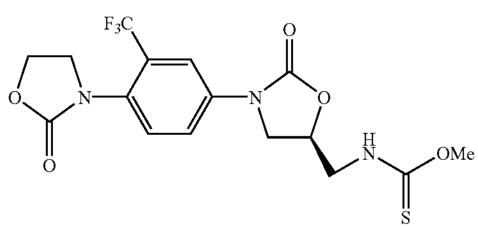 | ¹HNMR (CDCl₃, 200MHz): δ 7.9(m, 2H), 7.5(d, J=8.79 Hz, 1H), 6.7(s, 1H), 5.0(s, 1H), 4.5(t, 2H), 4.0(m, 9H). Mp: 146° C. |
| 98 | 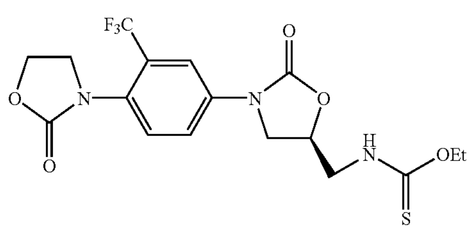 | ¹HNMR (CDCl₃, 200MHz): δ 7.8(m, 2H), 7.4(d, J=8.79 Hz, 1H), 6.7(s, 1H), 5.0(s, 1H), 4.5(m, 4H), 4.0(m, 6H), 1.3(m, 3H). Mp: 157° C. |
| 99 | 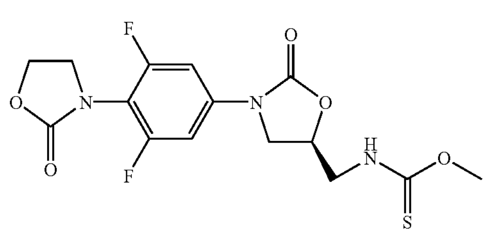 | ¹HNMR (CDCl₃, 200MHz): δ 7.29–7.24(m, 2H), 6.73 (hump, 1H), 4.96(huimp, 1H), 4.58(t, J=7.4Hz, 2H), 4.08–3.83(m, 9H). Mp: 182° C. |

| Example No. | Structure | Analytical Data |
|---|---|---|
| 100 | 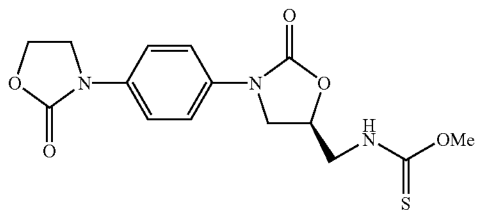 | $^1$HNMR (CDCl$_3$, 200MHz): δ 7.52(s, 4H), 6.81(bs, 1H), 4.91(hump, 1H), 4.49(t, J=7.8Hz, 2H), 4.13–3.82(m, 9H). Mp: 153° C. |
| 101 | 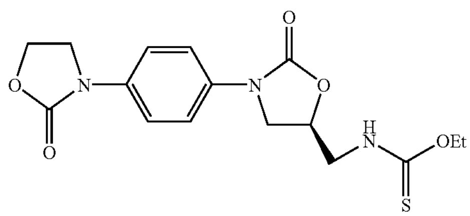 | $^1$HNMR (CDCl$_3$, 200MHz): δ 7.5(s, 4H), 6.7(s, 1H), 4.9(s, 1H), 4.5(m, 4H), 4.0(m, 6H), 1.3(t, J=6.8Hz, 3H). Mp: 168° C. |
| 102 | 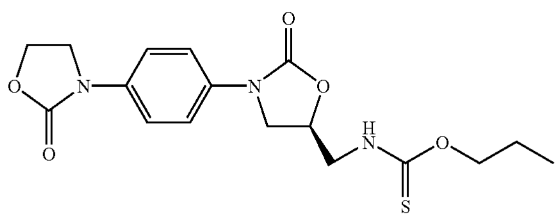 | $^1$HNMR (CDCl$_3$, 200MHz): δ 7.54(s, 4H), 6.7(s, 1H), 4.9 (m, 1H), 4.4(m, 4H), 4.0(m, 6H), 1.7(m, 2H), 0.95(t, J=7.4Hz, 3H). Mp: 176° C. |
| 103 | 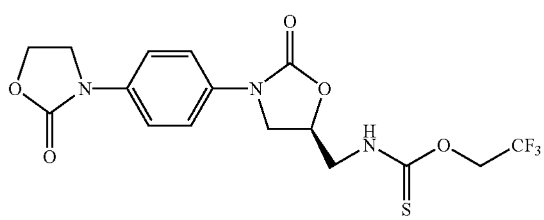 | $^1$HNMR (CDCl$_3$, 200MHz): δ 7.52(s, 4H), 7.26(bs, 1H), 4.96–4.77(m, 3H), 4.50(t, J=7.2Hz, 2H), 4.15–3.80(m, 6H). Melting Point (° C.): 181° C. |
| 104 | 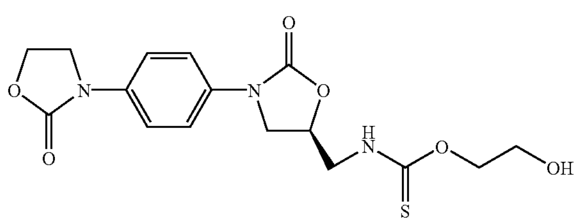 | $^1$HNMR (CDCl$_3$, 200MHz): δ 9.2–8.9(m, 1H), 7.5(s, 4H), 5.0–4.8(m, 1H), 4.6–4.4(m, 4H), 4.2–3.5(m, 8H). Mp: 141° C. |
| 105 | 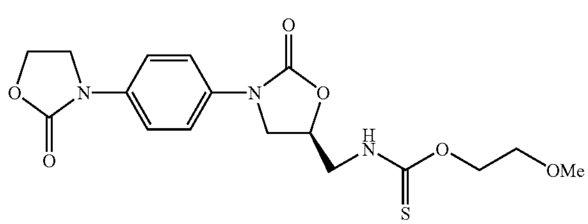 | $^1$HNMR (CDCl$_3$, 200MHz): δ 7.54(s, 4H), 6.81(bt, 1H), 4.91(m, 1H), 4.67–4.58(m, 2H), 4.50(t, J=7.2Hz, 2H), 4.13–3.82(m, 6H), 3.68–3.63 (m, 2H), 3.38(s, 3H). Mp: 149° C. |
| 106 | 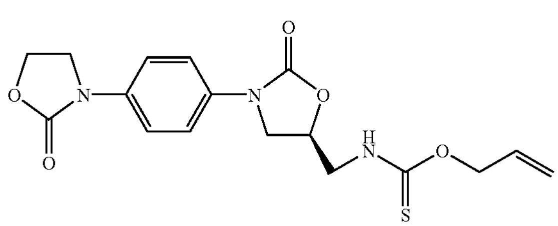 | $^1$HNMR (CDCl$_3$, 200MHz): δ 7.55(s, 4H), 7.26(s, 2H), 6.7 (s, 1H), 5.93(m, 1H), 5.29(m, 2H), 4.9(m, 3H), 4.5(t, J=7.4Hz, 2H), 4.0(m, 6H). Mp: 150° C. |

| Example No. | Structure | Analytical Data |
|---|---|---|
| 107 | 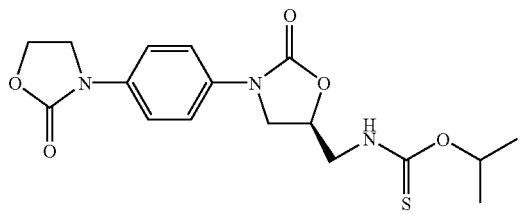 | ¹HNMR (CDCl₃, 200MHz): δ 7.54(s, 4H), 6.57(s, 1H), 5.5 (m, 1H), 4.92(m, 1H), 4.5(t, J=7.4Hz, 2H), 4.0(m, 6H), 1.31(dd, J=10.2Hz and 13.8 Hz, 6H).<br>Mp: 140° C. |
| 108 | 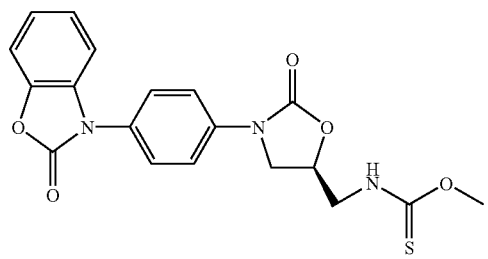 | ¹HNMR (CDCl₃, 200MHz): δ 7.72(d, J=9.2Hz, 2H), 7.57 (d, J=9.2Hz, 2H), 7.31–7.01 (m, 4H), 6.77(bs, 1H), 4.97–4.96(m, 1H), 4.19–3.91(m, 7H).<br>Mp: 141° C. |
| 109 | 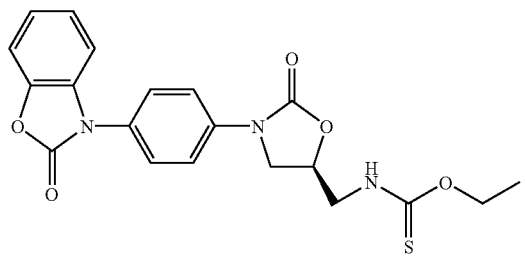 | ¹HNMR (CDCl₃, 200MHz): δ 7.73(d, J=8.8Hz, 2H), 7.56 (d, J=8.8Hz, 2H), 7.31–7.01 (m, 4H), 6.70(bs, 1H), 4.97 (m, 1H), 4.55–4.44(q, J=6.8 Hz, 2H), 4.19–3.92(m, 4H), 1.32(t, J=7.0Hz, 3H).<br>Mp: 147° C. |
| 110 | 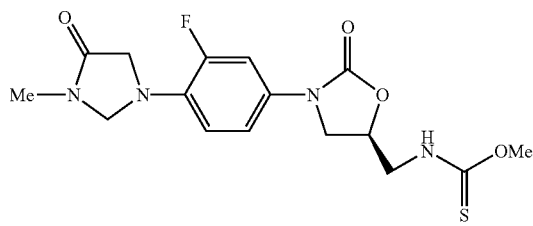 | ¹HNMR (CDCl₃, 200MHz): δ 2.8(s, 3H), 4.8(t, 1H), 3.6(m, 8H), 6.8(t, 1H), 7.2(d, 1H), 7.5(dd, 1H).<br>Mp: 218° C. |
| 111 | 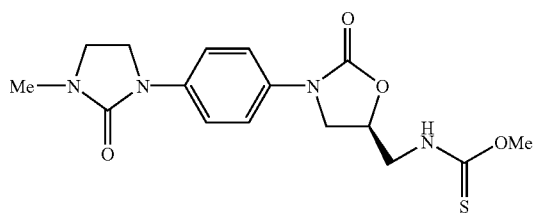 | ¹HNMR (CDCl₃, 200MHz): δ 1.5(s, 3H), 2.9(s, 3H), 3.6(t, 2H), 4.9(m, 1H), 6.8(m, 1H), 7.8(d, 2H).<br>Mp: 209° C. |
| 112 | 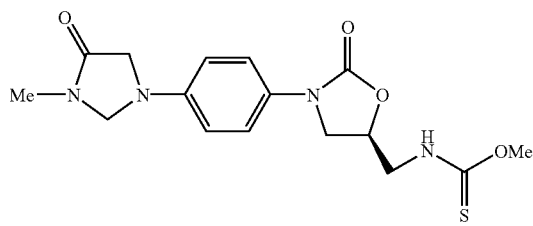 | ¹HNMR (DMSO-d⁶, 200MHz): 9.5(br, 1H), 7.4(d, J=8.8Hz, 2H), 6.6(d, J=8.8 Hz, 2H), 4.90–4.80(m, 1H), 4.7(s, 2H), 4.2–3.4(m, 9H), 2.9(s, 3H).<br>Mp: 205° C. |

| Example No. | Structure | Analytical Data |
|---|---|---|
| 113 | 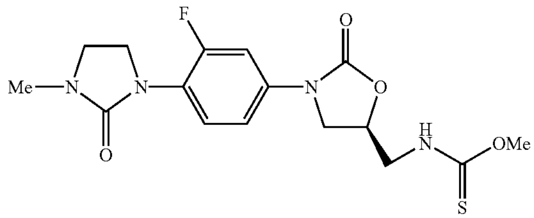 | ¹HNMR (CDCl₃, 200MHz): δ 7.5(m, 2H), 7.1(m, 1H), 6.9 (s, 1H), 4.9(m, 1H), 3.8(m, 9H), 3.4(t, J=8.8Hz, 2H), 2.9(s, 3H).<br>Mp: 146° C. |
| 114 | 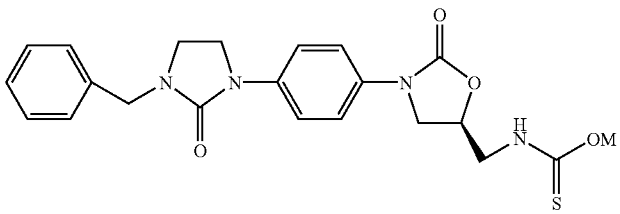 | ¹HNMR (CDCl₃, 200MHz): δ 7.6–7.2(m, 9H), 6.7(bt, 1H), 5.0–4.8(m, 1H), 4.5(s, 2H), 4.2–3.6(m, 9H), 3.4(t, J=8.8 Hz, 2H).<br>Mp: 170° C. |
| 115 | 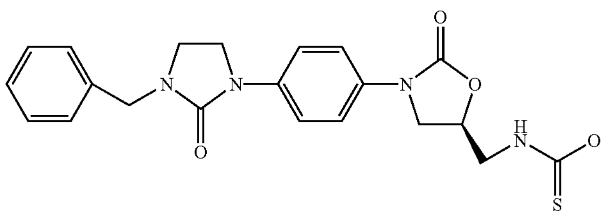 | ¹HNMR (CDCl₃, 200MHz): δ 7.6–7.2(m, 9H), 6.7(bt, 1H), 5.0–4.8(m, 1H), 4.6–4.4(m, 4H), 4.2–3.6(m, 6H), 3.7(t, J=8.3Hz, 2H), 1.3(t, J=6.8 Hz, 3H).<br>Mp: 160° C. |
| 116 | 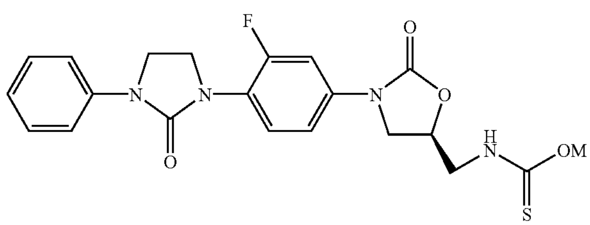 | ¹HNMR (CDCl₃, 200MHz): δ 9.5(m, 1H), 7.6(m, 4H), 7.4 (m, 3H), 7.0(m, 1H), 4.9(m, 1H), 4.2(m, 1H), 3.8–4.0(m, 7H), 3.3(s, 3H).<br>Mp: 174° C. |
| 117 | 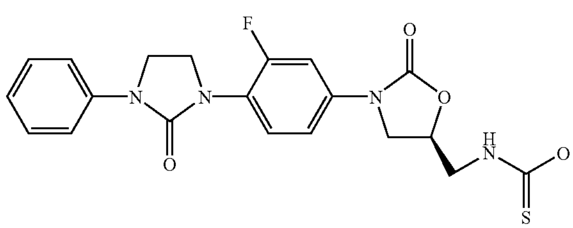 | ¹HNMR (CDCl₃, 200MHz): δ 9.5(m, 1H), 7.6(m, 4H), 7.3 (m, 3H), 7.1(t, 1H), 4.8(m, (1H), 4.4(m, 2H), 4.2(m, 1H), 3.7–4.1(m, 5H), 3.5(m, 2H), 1.2(t, 3H).<br>Mp: 195° C. |
| 118 | 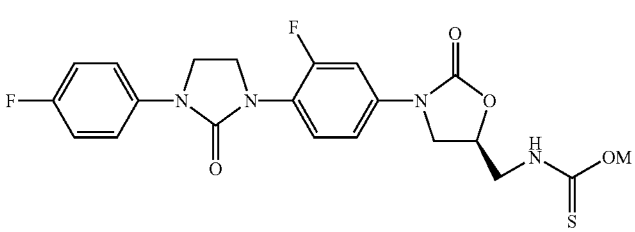 | ¹HNMR (CDCl₃, 200MHz): δ 7.5(m, 4H), 7.0(m, 4H), 4.9 (m, 1H), 4.0(11H).<br>Mp: 208° C. |

| Example No. | Structure | Analytical Data |
|---|---|---|
| 119 | 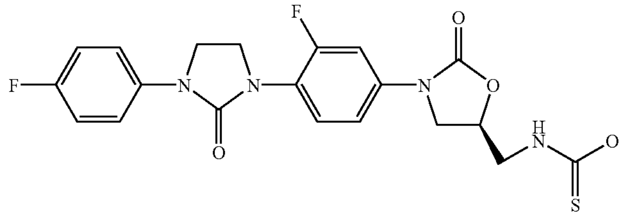 | ¹HNMR (CDCl₃, 200MHz): δ 7.6(m, 4H), 7.0–7.2(m, 3H), 4.9(m, 2H), 4.5(m, 2H), 4.0 (m, 8H), 1.3(t, 3H). Mp: 215° C. |
| 120 | 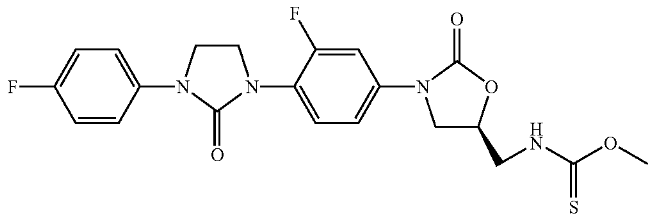 | ¹HNMR (CDCl₃, 200MHz): δ 7.5(m, 4H), 7.0(m, 3H), 5.5 (m, 1H), 4.9(m, 1H), 4.0(m, 8H), 1.3(t, 6H). Mp: 220° C. |
| 121 | 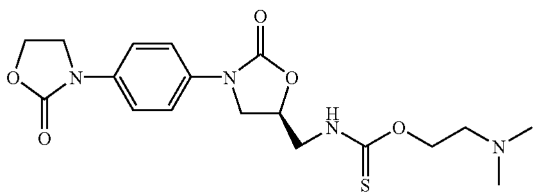 | ¹HNMR (DMSO-d⁶, 200 MHz): δ 9.60–9.40(m, 1H), 7.57(s, 4H), 5.00–4.75(m, 1H), 4.44–3.40(m, 12H), 2.16 (s, 6H). Mp: 161° C. |
| 122 | 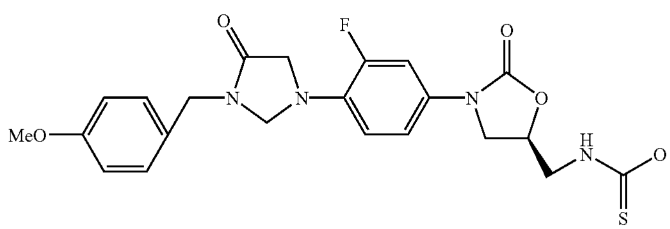 | ¹HNMR (CDCl₃, 200 MHz): δ 7.40(dd, J=17.6, 2.4Hz, 1H), 7.24(d, J=9.7Hz, 2H), 7.04(d, J=8.8Hz, 1H), 6.89 (d, J=8.8Hz, 2H), 6.78(bt, 1H), 6.58–6.49(m, 1H), 5.00–4.80(m, 1H), 4.75(s, 2H), 4.54(s, 2H), 4.20–3.60(m, 9H), 3.81(s, 3H). Mp: 158° C. |
| 123 | 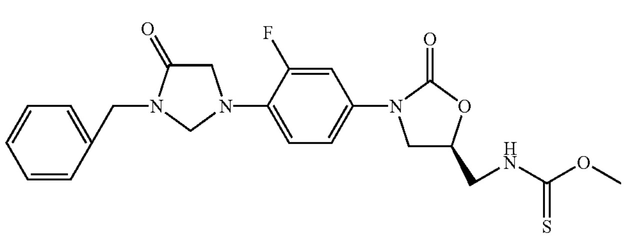 | ¹HNMR (DMSO-d⁶, 200 MHz): δ 9.50–9.35(m, 1H), 7.60–6.60(m, 8H), 5.50–5.30 (m, 1H), 4.95–4.70(m, 1H), 4.74(s, 2H), 4.55(s, 2H), 4.20–3.25(m, 6H), 1.40–1.10 (bd, 6H). Mp: 192° C. |
| 124 | 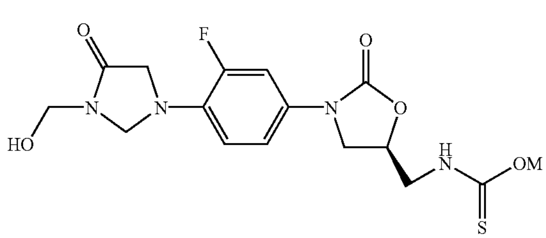 | ¹HNMR (DMSO-d⁶, 200 MHz): δ 9.55–9.35(m, 1H), 7.45(d, J=18.1Hz, 1H), 7.15 (d, J=8.8Hz, 1H), 6.90–6.80 (m, 1H), 6.09(t, J=6.8Hz, 1H), 4.87(s, 2H), 4.90–4.75 (m, 1H), 4.71(d, J=6.8Hz, 2H), 4.20–3.10(m, 9H). Mp: 184° C. |

J. General procedure for the conversion of

K. General procedure for the conversion of

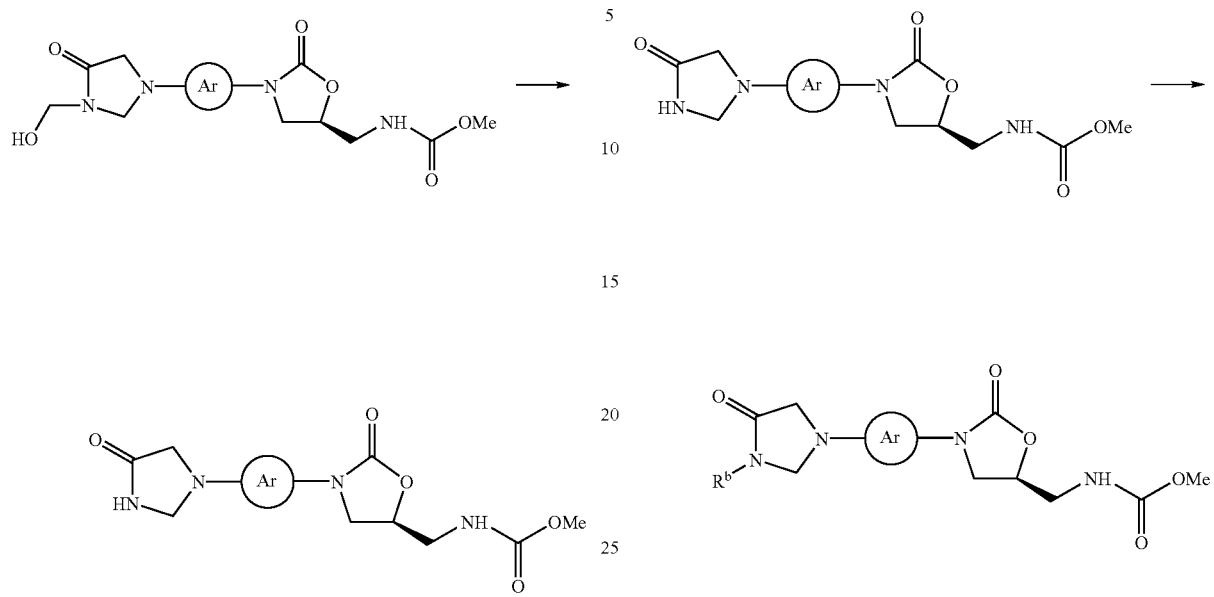

where

Ar=Substituted or unsubstituted phenyl ring.

Sodium hydride (360 mg, 7.5 mmol) was added to a solution of starting material (300 mg, 0.75 mmol) in dry THF (30 mL) and the resultant suspension was stirred at room temperature overnight. The reaction mixture was diluted with ethyl acetate (150 mL) and washed with water, brine and dried. The residue obtained upon evaporation of solvent was passed through a column of silica gel to afford the product as a colorless solid (150 mg, 54% yield).

Example 125 has been been prepared according to the general procedure J.

where

Ar=Substituted phenyl ring and $R^b$ represents $(C_1–C_6)$ alkyl or aralkyl.

To a solution of starting material (1 eq) in dry DMF was added NaH (1.2 eq) at 0° C. under argon followed by appropriate alkyl halide or aralkyl halide (1.2 eq). The reaction mixture was stirred for 2–6 h while monitoring by TLC. After the consumption of starting material, the reaction mixture was diluted with ethyl acetate and washed with water, brine and dried. The residue obtained upon evaporation of solvent was passed through a column of silica gel to afford the product.

Example 126–129 have been been prepared according to the general procedure K.

| Example No. | Structure | Analytical Data |
|---|---|---|
| 125 | 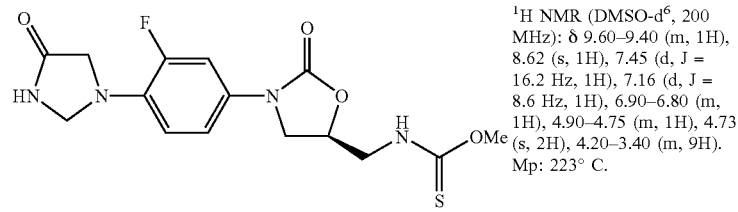 | $^1$H NMR (DMSO-$d^6$, 200 MHz): δ 9.60–9.40 (m, 1H), 8.62 (s, 1H), 7.45 (d, J = 16.2 Hz, 1H), 7.16 (d, J = 8.6 Hz, 1H), 6.90–6.80 (m, 1H), 4.90–4.75 (m, 1H), 4.73 (s, 2H), 4.20–3.40 (m, 9H). Mp: 223° C. |

| Example No. | Structure | Analytical Data |
|---|---|---|
| 126 | 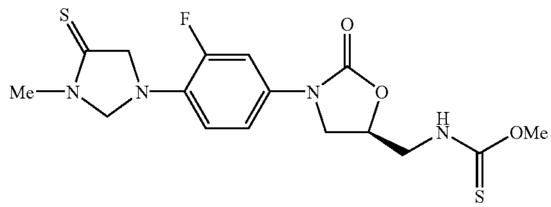 | $^1$H NMR (DMSO-d$^6$, 200 MHz): δ 9.60–9.40 (m, 1H), 7.49 (dd, J = 15.6, 2.4 Hz, 1H), 7.18 (d, J = 9.1 Hz, 1H), 6.95–6.80 (m, 1H), 5.17 (s, 2H), 4.95–4.70 (m, 1H), 4.42 (s, 2H), 4.20–3.40 (m, 7H). Mp: 195° C. |
| 127 | 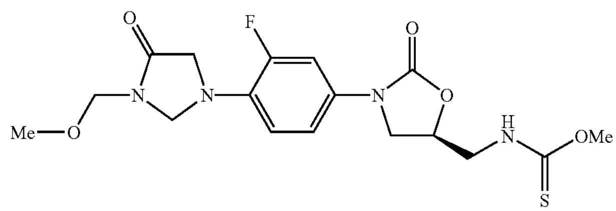 | $^1$H NMR (CDCl$_3$, 200 MHz): δ 7.46 (dd, J = 15.1, 2.4 Hz, 1H), 7.10 (d, J = 8.8 Hz, 1H), 6.77 (bt, 1H), 6.65–6.56 (m, 1H), 4.97 (s, 2H), 4.97–4.80 (m, 1H), 4.84 (s, 2H), 4.20–3.55 (m, 9H), 3.37 (s, 3H). Mp: 160° C. |
| 128 | 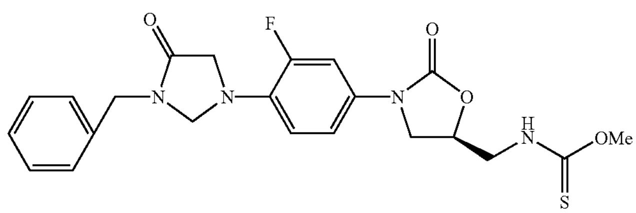 | $^1$H NMR (CDCl$_3$ + DMSO-d$^6$, 200 MHz): δ 9.95–9.25 (m, 1H), 7.55–7.25 (m, 6H), 7.45 (d, J = 15.4 Hz, 1H), 6.63–6.54 (m, 1H), 5.00–4.80 (m, 1H), 4.77 (s, 2H), 4.60 (s, 2H), 4.20–3.75 (m, 9H). Mp: 176° C. |
| 129 | 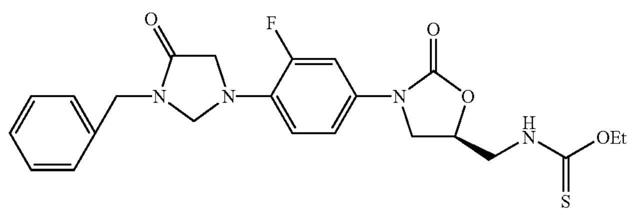 | $^1$H NMR (CDCl$_3$, 200 MHz): δ 7.50–7.20 (m, 6H), 7.04 (d, J = 8.6 Hz, 1H), 6.78 (bt, 1H), 6.58–6.49 (m, 1H), 5.00–4.35 (m, 7H), 4.20–3.60 (m, 6H), 1.31 (t, J = 7.0 Hz, 3H). Mp: 184° C. |

L. General procedure for the conversion of

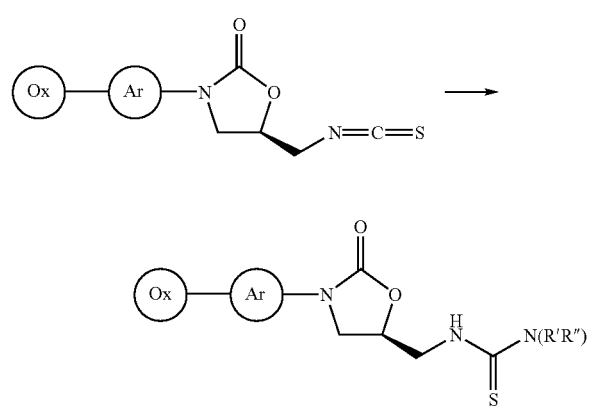

where

Ox=2-Oxazolidinone or its equivalent derivatives. An equivalent derivative of 2-oxazolidinone is a five membered heterocyclic group containing two heteroatoms selected from oxygen, nitrogen and sulfur; and substituted by an =O or =S group, the heterocycle may be fused with substituted or unsubstituted phenyl group.

Ar=Substituted or unsubstituted phenyl ring and R' represents hydrogen, (C$_1$–C$_6$)alkyl, (C$_2$–C$_6$)alkenyl, substituted or unsubstituted aralkyl, heteroaralkyl, hydroxy(C$_1$–C$_6$) alkyl, R" represents hydrogen or alkyl or the two R' and R" groups together form a 5 or 6 membered cyclic structures containing one or two hetero atoms.

Ammonia gas (or appropriate amine) was bubbled to a solution of isothiocyanate in THF at −10° C. over 20 min. The resultant mixture was stirred at room temperature for 1 h and then diluted with ethyl acetate. The organic layer was washed with water (2 times), brine and dried. The residue obtained upon evaporation of the solvent was passed through a column of silica gel to afford the product.

Examples 130–143 have been prepared according to the general procedure L

| Example No. | Structure | Analytical Data |
|---|---|---|
| 130 | 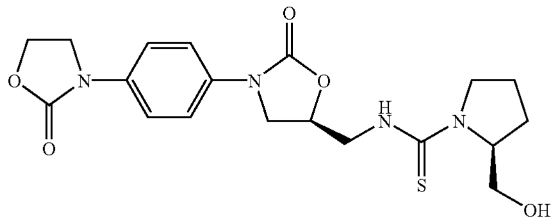 | ¹HNMR (CDCl₃, 200 MHz): δ 7.51 (s, 4H), 4.98–4.95 (m, 1H), 4.49 (t, J = 7.8 HZ, 2H), 4.17–3.88 (m, 8H), 3.71–3.69 (m, 3H), 1.93–1.78 (m, 4H). Mp: 159° C. |
| 131 | 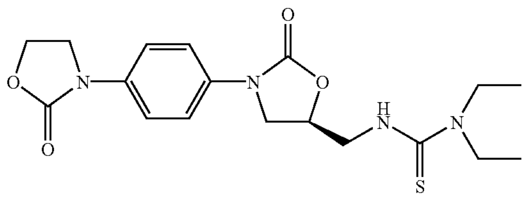 | ¹HNMR (DMSO-d⁶, 200 MHz): δ 7.63 (s, 1H), 7.57 (s, 4H), 4.94–4.91 (m, 1H), 4.44 (t, J = 7.4 Hz, 2H), 4.17–3.75 (m, 6H), 3.66–3.56 (q, J = 6.8 Hz, 4H), 1.07 (t, J = 6.8 Hz, 6H). Mp: 103° C. |
| 132 | 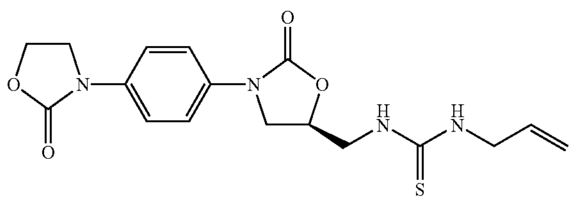 | ¹HNMR (DMSO-d⁶, 200 MHz): δ 7.79 (bs, 1H), 7.57 (s, 4H), 5.80–5.75 (m, 1H), 5.15–5.01 (m, 2H), 4.86 (m, 1H), 4.44 (t, J = 7.4 Hz, 2H), 4.17–4.01 (m, 5H), 3.85 (m, 2H). Mp: 171° C. |
| 133 | 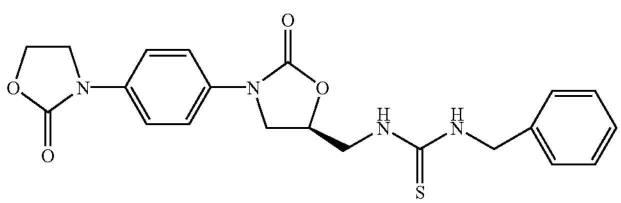 | ¹HNMR (DMSO-d⁶, 200 MHz): δ 8.05 (bs, 1H), 7.86 (bs, 1H), 7.57 (s, 4H), 7.25 (s, 5H), 4.88–4.84 (m, 1H), 4.67 (s, 2H), 4.44 (t, J = 7.8 Hz, 2H), 4.16–4.01 (m, 3H), 3.89–3.86 (m, 3H). Mp: 181° C. |
| 134 | 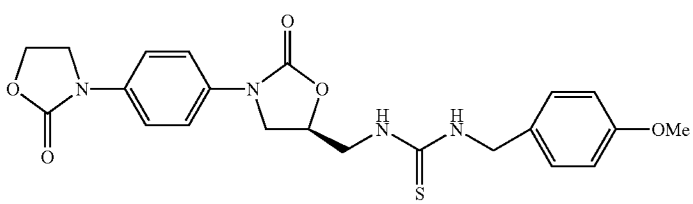 | ¹HNMR (DMSO-d⁶, 200 MHz): δ 8.00 (bs, 1H), 7.80 (bs, 1H), 7.57 (s, 4H), 7.19–7.15 (d, J = 8.4 Hz, 2H), 6.84–6.80 (d, J = 8.2 Hz, 2H), 4.86 (bs, 1H), 4.57 (bs, 2H), 4.44 (t, J = 7.4 Hz, 2H), 4.08–4.01 (m, 3H), 3.88–3.85 (m, 3H), 3.70 (s, 3H). Mp: 169° C. |
| 135 | 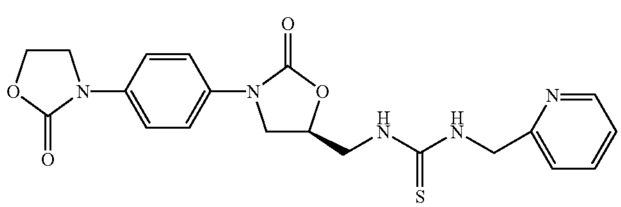 | ¹HNMR (DMSO-d⁶, 200 MHz): δ 8.50–8.48 (d, J = 3.8 Hz, 1H), 8.16 (m, 2H), 7.69 (t, J = 7.8 Hz, 1H), 7.57 (s, 4H), 7.26–7.22 (d, J = 7.8 Hz, 2H), 4.88 (m, 1H), 4.75 (bs, 2H), 4.44 (t, J = 7.2 Hz, 2H), 4.18–4.01 (m, 3H), 3.89–3.82 (m, 3H). Mp: 165° C. |
| 136 | 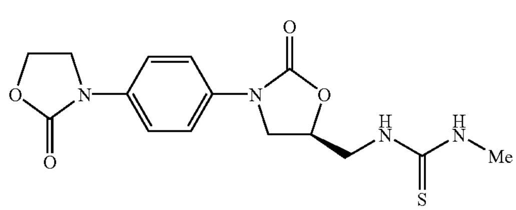 | ¹HNMR (DMSO-d⁶, 200 MHz): δ 7.77 (bs, 1H), 7.57 (s, 5H), 4.86 (m, 1H), 4.44 (t, J = 7.8 Hz, 2H), 4.17–4.01 (m, 3H), 3.81–3.33 (m, 3H), 2.83 (bs, 3H). Mp: 175° C. |

-continued

| Example No. | Structure | Analytical Data |
|---|---|---|
| 137 | 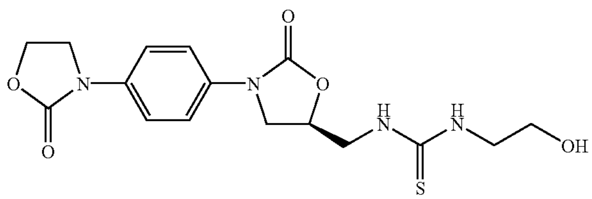 | ¹HNMR (DMSO-d⁶, 200 MHz): δ 7.86 (hump, 1H), 7.66 (hump, 1H), 7.57 (s, 4H), 4.78–4.68 (m, 2H), 4.43 (t, J = 7.2 Hz, 2H), 4.12–4.01 (m, 3H), 3.83 (bs, 3H), 3.46–3.33 (m, 4H). Mp: 161° C. |
| 138 | 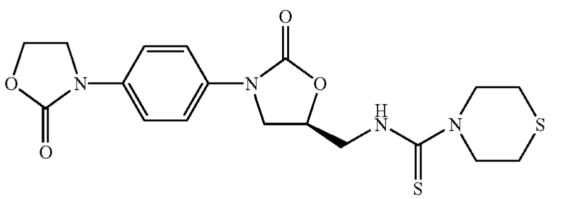 | ¹HNMR (DMSO-d⁶, 200 MHz): δ 8.05 (hump, 1H), 7.57 (s, 4H), 4.95 (m, 1H), 4.43 (t, J = 7.2 Hz, 2H), 4.08–3.89 (m, 8H), 2.57 (s, 4H), 2.49 (s, 4H). Mp: 159° C. |
| 139 | 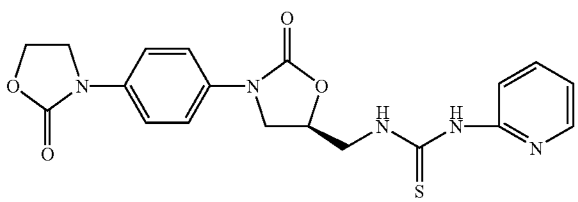 | ¹HNMR (DMSO-d⁶, 200 MHz): δ 12.06 (bs, 1H), 10.76 (s, 1H), 8.14–8.11 (d, J = 5.0 Hz, 1H), 7.77 (t, J = 8.2 Hz, 1H), 7.52 (s, 4H), 7.17–7.13 (d, J = 3.2 Hz, 1H), 7.04 (t, J = 5.8 Hz, 1H), 5.05–5.03 (m, 1H), 4.43 (t, J = 7.4 Hz, 2H), 4.22 (t, J = 9.2 Hz, 1H), 4.07–3.84 (m, 5H). Mp: 189° C. |
| 140 | 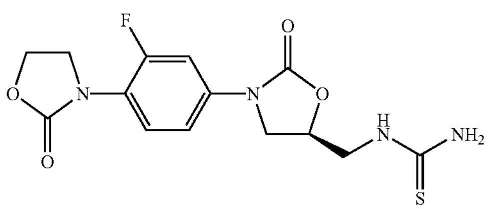 | ¹HNMR (CDCl₃ + DMSO-d⁶, 200 MHz): δ 8.07 (bs, 1H), 7.62–7.40 (m, 2H), 7.16 (d, J = 7.8 Hz, 1H), 6.65 (bs, 1H), 4.85 (bs, 1H), 4.48 (t, J = 8.0 Hz, 2H), 4.04–3.96 (m, 6H). Mp: 178° C. |
| 141 | 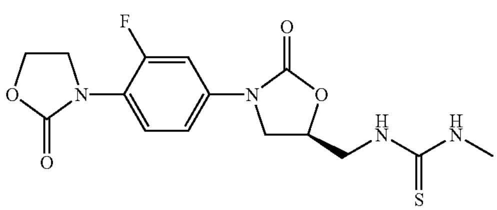 | ¹HNMR (CDCl₃ +DMSO-d⁶, 200 MHz): δ 7.68–7.19 (m, 5H), 4.92 (hump, 1H), 4.53 (t, J = 7.8 Hz, 2H), 4.08–3.98 (m, 6H), 3.10 (s, 3H). Mp: 144° C. |
| 142 | 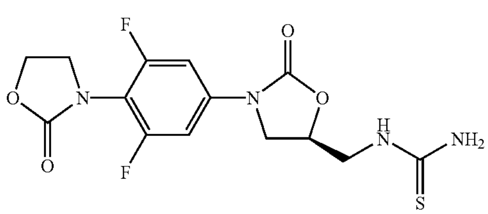 | ¹HNMR (CDCl + DMSO-d⁶, 200 MHz): δ 8.10 (bs, 1H), 7.35 (d, J = 8.4 Hz, 2H), 6.58 (bs, 1H), 4.91–4.89 (m, 1H), 4.58 (t, J = 7.8 Hz, 2H), 4.54–3.87 (m, 6H). Mp: 92° C. |
| 143 | 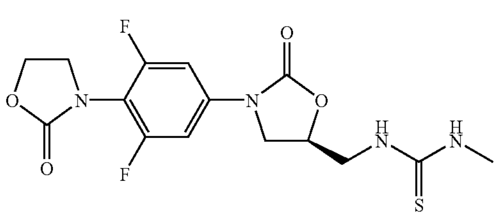 | ¹HNMR (CDCl₃, 200 MHz): δ 7.26 (s, 2H), 6.39 (hump, 2H), 4.93 (hump, 1H), 4.60 (t, J = 7.4 Hz, 2H), 4.21–3.93 (m, 6H), 2.99 (d, J = 4.8 Hz, 3H). Mp: 113° C. |

N1-((5S)-3-{4-[2-oxo-1,3-oxazolan-3yl]phenyl}-2-oxo-1,3-oxazolan-5-ylmethyl)-(N,N-dimethylamino)ethylthiocarbamate hydrochloride

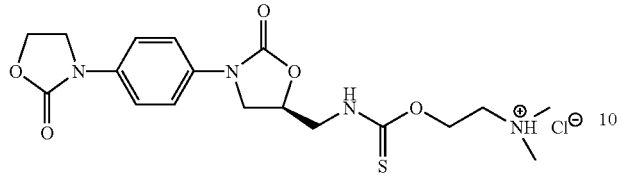

N1-((5S)-3-{4-2-oxo-1,3-oxazolan-3yl]phenyl}-2-oxo-1,3-oxazolan-5-ylmethyl)-(N,N-dimethylamino)ethylthiocarbamate (obtained in Example 121), was taken in methanol (100 mg) and was bubbled with HCl gas for 30 min. Then methanol was evaporated from the resultant mixture and washed with ether twice to obtain the title compound (Yield: 100%). Mp: 100° C. (hygroscopic).

$^1$H NMR (DMSO-d$^6$, 200 MHz): δ 10.60 (bs, 1H), 9.85–9.65 (m, 1H), 7.58 (s, 4H), 5.00–4.65 (m, 3H), 4.44 (t, J=7.6 Hz, 2H), 4.25–3.40 (m, 8H), 2.81 (s, 3H), 2.79 (s, 3H).

In vitro Data

Minimum Inhibiton Concentrations (MICs) were determined by broth microdilution technique as per the guidelines prescribed om the fifth edition of Approved Standards, NCCLS document M7-A5 Vol 20—No 2, 2000 Villinova, Pa.

Initial stock solution of the test compound was prepared in DMSO. Subsequent two fold dilutions were carried out in sterile Mueller Hinton Broth (Difco) (MHB).

Frozen cultures stocks were inoculated into 50 ml sterile MHB in 250 ml Erlyn Meyer flasks.

Composition of MHB is as follows:
Beef Extract Powder—2.0 g/liter
Acid Digest of Casein—17.5 g/liter
Soluble Starch—1.5 g/liter
Final pH 7.3±0.1

Flasks were incubated for 4 to 5 h at 35° C. on a rotary shaker at 150 rpm. Inoculum was prepared by diluting the culture in sterile MHB to obtain a turbidity of 0.5 McFarland standard. This corresponds to 1–2×10$^8$ CFU/ml. The stock was further diluted in sterile broth to obtain 1–2×10$^6$ CFU/ml. 50 µl of the above diluted inoculum was added from 1–10 wells. The plates were incubated overnight at 37° C.

MIC is read as the lowest concentration of the compound that completely inhibits growth of the organism in the microdilution wells as detected by the unaided eye.

| Organism | Culture No. | DRCC No. |
|---|---|---|
| Staphylococcus aureus | ATCC 33591 | 019 |
| Staphylococcus aureus | ATCC 49951 | 213 |
| Staphylococcus aureus | ATCC 29213 | 035 |
| Enterococcus faecalis | ATCC 29212 | 034 |
| Enterococcus faecalis | NCTC 12201 | 153 |
| Enterococcus faecium | NCTC 12202 | 154 |
| Escherichia coli | ATCC 25922 | 018 |

ATCC: American Type Culture Collection, USA
NCTC: National Collections of Type Cultures, Colindale, UK
DRCC: Dr. Reddy's Culture Collection, Hyderabad, India.

The in vitro antibacterial activity data is shown in TABLE 1.

TABLE 1

In vitro Activity of Compounds against Gram positive and Gram negative bacteria

Antimicrobial Screening (MIC) µg/ml

| | Staphylococcus aureus | | | Enterococcus sp | | | E coli |
|---|---|---|---|---|---|---|---|
| Example No. | 019 MRSA | 213 Smith S | 035 S | 034 S | 153 R | 154 R | 18 S |
| 40 | 8.0 | 4.0 | 8.0 | 16.0 | 8.0 | 8.0 | 32.0 |
| 62 | 2.0 | 1.0 | 4.0 | — | 8.0 | 8.0 | 32.0 |
| 76 | 2.0 | 2.0 | 4.0 | 4.0 | 4.0 | 4.0 | >32.0 |
| 79 | 2.0 | 2.0 | 4.0 | 4.0 | 8.0 | 8.0 | 32.0 |
| 88 | 1.0 | 1.0 | 2.0 | 2.0 | 2.0 | 2.0 | >32.0 |
| 89 | 4.0 | 4.0 | 4.0 | 8.0 | 8.0 | 8.0 | >32.0 |
| 99 | 2.0 | 2.0 | 2.0 | 2.0 | 2.0 | 2.0 | >32.0 |
| 100 | 0.5 | 0.5 | 0.5 | 1.0 | 1.0 | 1.0 | 32.0 |
| 107 | 2.0 | 4.0 | 4.0 | 8.0 | 4.0 | 4.0 | 32.0 |
| 110 | 0.5 | 0.5 | 0.5 | 1.0 | 1.0 | 1.0 | 32.0 |
| 113 | 2.0 | 4.0 | 4.0 | 4.0 | 4.0 | 8.0 | 32.0 |
| 124 | 0.25 | 0.25 | 0.5 | 0.5 | 0.25 | 0.5 | — |
| 125 | 0.25 | 0.25 | 0.5 | 0.5 | 0.25 | 0.5 | — |
| 127 | 0.5 | 1.0 | 1.0 | 1.0 | 1.0 | 1.0 | — |

What is claimed is:

1. A compound of the formula (I)

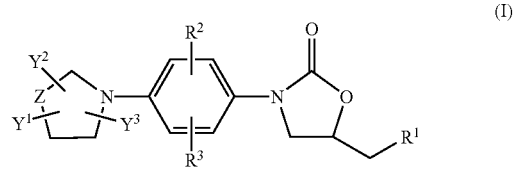

wherein
R$^1$ represents halo, azido, isothiocyanate, thioalcohol, OR$^4$, NHR$^4$ or N(R$^4$)$_2$, where R$^4$ represents substituted or unsubstituted groups selected from acyl, thioacyl, (C$_1$–C$_6$)alkoxycarbonyl, (C$_3$–C$_6$) ycloalkoxythiocarbonyl, (C$_2$–C$_6$) alkenyloxycarbonyl, (C$_2$–C$_6$) alkenylcarbonyl, aryloxycarbonyl, (C$_1$–C$_6$)alkoxythiocarbonyl, (C$_2$–C$_6$)alkenyloxythio-carbonyl, aryloxythiocarbonyl, —C(=O)—C(=O)-alkyl, —C(=O)—C(=O)-aryl, —C(=O)—C(=O)-alkoxy, —C(=O)—C(=O)-aryloxy, —(C=S)—S-alkyl, —(C=S)—NH$_2$, —(C=S)—NH-alkyl, —C(=S)—N-(alkyl)$_2$, —C(=S)—NH-alkenyl, (C=S)—(C=O)-alkoxy, —(C=S)—(C=O)-aryloxy, —C(=S)—O—(C=O)-alkyl, C(=S)—C(=S)-alkyl, —C(=S)—C(S)-aryl, thiomorpholinylthiocarbonyl or pyrrolidinylthiocarbonyl;
R$^2$ and R$^3$ are same or different and independently represent hydrogen, halogen atom, (C$_1$–C$_6$)alkyl group, halo(C$_1$–C$_6$)alkyl, cyano, nitro, SR$^a$, NR$^a$, OR$^a$ where R$^a$ represents substituted or unsubstituted (C$_1$–C$_6$)alkyl group, or halo(C$_1$–C$_6$)alkyl;
Z represents O,
Y$^1$ represents =O or =S group and Y$^2$ and Y$^3$ independently represent hydrogen, halogen, cyano, nitro, formyl, hydroxy, amino, =O, =S group, or substituted or unsubstituted groups selected from (C$_1$–C$_6$)alkyl, hydroxy($C_1$–$C_6$)alkyl, ($C_1$–$C_6$) alkoxy($C_1$–$C_6$) alkyl, ($C_1$–$C_6$)alkoxycarbonyl, carboxy($C_1$–$C_6$)alkyl, ($C_1$–$C_6$)alkylsulfonyl, ($C_1$–$C_6$)alkylcarbonyl-amino ($C_1$–$C_6$) lkyl, arylcarbonylamino($C_1$–$C_6$)alkyl, ($C_1$–$C_6$) alkylcarbonyloxy($C_1$–$C_6$)alkyl, amino ($C_1$–$C_6$)alkyl, mono($C_1$–$C_6$)alkylamino, di($C_1$–$C_6$) alkylamino, arylamino, ($C_1$–$C_6$)alkoxy, aryl, aryloxy, aralkyl, heteroaryl, heteroaralkyl, heterocyclyl or heterocycloalkyl;

$Y^2$ and $Y^3$ when present on adjacent carbon atoms together also form a substituted or unsubstituted 5 or 6 membered aromatic or non-aromatic cyclic structure, optionally containing one or two hetero atoms; its stereoisomers, its polymorphs, its pharmaceutically acceptable salts or its pharmaceutically acceptable solvates.

2. The compound according to claim 1, wherein the substituents on $R^4$ are selected from halogen, hydroxy, amino, monoalkylamino, dialkylamino, cyano, nitro, alkoxy, aryl, hydroxyaryl, pyridyl, hydroxyalkyl, alkoxyaryl or carboxyl and its derivatives.

3. The compound according to claim 1, wherein the substituents on $Y^2$ and $Y^3$ are selected from hydroxy, nitro, cyano, amino, tert-butyldimethylsilyloxy (TBSO), halogen, ($C_1$–$C_6$)alkyl, ($C_1$–$C_6$)alkoxy, ($C_3$–$C_6$)cycloalkyl, aryl, benzyloxy, acyl, carboxyl or acyloxy groups.

4. The compound according to claim 1, wherein the cyclic structure formed by $Y^2$ and $Y^3$ is selected from substituted or unsubstituted benzene, pyridine, pyrrolidine, furan, thiophene, morpholine, piperazine or pyrrole.

5. A compound of the formula (I) as defined according to claim 1, which is selected from:
- (5R)-3-[3-fluoro-4-(2-oxo-1,3-oxazolan-3-yl)phenyl]-5-hydroxymethyl-1,3-oxazolan-2-one or its salts;
- (5R)-3-[3-fluoro-4-(2-thioxo-1,3-oxazolan-3-yl)phenyl]-5-hydroxymethyl-1,3-oxazolan-2-one or its salts;
- 3-{2-fluoro-4-[(5R)-5-hydroxymethyl-2-oxo-1,3-oxazolan-3-yl]phenyl}-2,3-dihydrobenzo[d][1,3]oxazol-2-one or its salts;
- 3-{2-fluoro-4-[(5R)-5-hydroxymethyl-2-oxo-1,3-oxazolan-3-yl]phenyl}-6-methyl-2,3-dihydrobenzo[d][1,3]oxazol-2-one or its salts;
- 3-{2-fluoro-4-[(5R)-5-hydroxymethyl-2-oxo-1,3-oxazolan-3-yl]phenyl}-5-methyl-2,3-dihydrobenzo[d][1,3]oxazol-2-one or its salts;
- (5R)-5-hydroxymethyl-3-[4-(2-oxo-1,3-oxazolan-3-yl)-3-trifluoromethylphenyl]-1,3-oxazolan-2-one or its salts;
- (5R)-3-[2-fluoro-4-(2-oxo-1,3-oxazolan-3-yl)phenyl]-5-hydroxymethyl- 1,3-oxazolan-2-one or its salts;
- (5R)-3-[3,5-fluoro-4-(2-oxo-1,3-oxazolan-3-yl)phenyl]-5-hydroxymethyl-1,3-oxazolan-2-one or its salts;
- (5R)-5-hydroxymethyl-3-[4-(2-oxo-1,3-oxazolan-3-yl)phenyl]-1,3-oxazolan-2-one or its salts;
- 3-{4-[(5R)-5-hydroxymethyl-2-oxo-1,3-oxazolan-3-yl]phenyl}-2,3-dihydrobenzo[d][1,3]oxazol-2-one or its salts;
- (5R)-azidomethyl-3-[3-fluoro-4-(2-oxo-1,3-oxazolan-3-yl)phenyl]-1,3-oxazolan-2-one or its salts;
- 3-{4-[(5R)-5-azidomethyl-2-oxo-1,3-oxazolan-3-yl]-2-fluorophenyl}-6-methyl-2,3-dihydrobenzo[d][1,3]oxazol-2-one or its salts;
- 3-{4-[(5R)-5-azidomethyl-2-oxo-1,3-oxazolan-3-yl]-2-fluorophenyl}-5-methyl-2,3-dihydrobenzo[d][1,3]oxazol-2-one or its salts;
- (5R)-5-azidomethyl-3-[4-(2-oxo-1,3-oxazolan-3-yl)-3-trifluoromethylphenyl]-1,3-oxazolan-2-one or its salts;
- (5R)-5-azidomethyl-3-[2-fluoro-4-(2-oxo-1,3-oxazolan-3-yl)phenyl]-1,3-oxazolan-2-one or its salts;
- (5R)-azidomethyl-3-[3,5-difluoro-4-(2-oxo-1,3-oxazolan-3-yl)phenyl]-1,3-oxazolan-2-one or its salts;
- (5R)-5-azidomethyl-3-[4-(2-oxo-1,3-oxazolan-3-yl)phenyl]-1,3-oxazolan-2-one or its salts;
- 3-{4-[(5R)-5-azidomethyl-2-oxo-1,3-oxazolan-3-yl]phenyl}-2,3-dihydrobenzo[d][1,3]oxazol-2-one or its salts;
- (5R)-aminomethyl-3-[3-fluoro-4-(2-oxo-1,3-oxazolan-3-yl)phenyl]-1,3-oxazolan-2-one or its salts;
- (5R)-5-aminomethyl-3-[4-(2-oxo-1,3-oxazolan-3-yl)-3-trifluoromethylphenyl]-1,3-oxazolan-2-one or its salts;
- (5R)-5-aminomethyl-3-[4-(2-oxo-1,3-oxazolan-3-yl)phenyl]-1,3-oxazolan-2-one or its salts;
- N-{(5S)-3-[3-fluoro-4-(2-oxo-1,3-oxazolan-3-yl)phenyl]-2-oxo-1,3-oxazolan-5-ylmethyl}methanamide or its salts;
- N-{(5S)-3-[3,5-difluoro-4-(2-oxo-1,3-oxazolan-3-yl)phenyl]-2-oxo-1,3-oxazolan-5-ylmethyl}methanamide or its salts;
- N1-{(5S)-3-[3-fluoro-4-(2-oxo-1,3-oxazolan-3-yl)phenyl]-2-oxo-1,3-oxazolan-5-ylmethyl}acetamide or its salts;
- N1-{(5S)-3-[3-fluoro-4-(2-oxo-1,3-oxazolan-3-yl)phenyl]-2-oxo-1,3-oxazolan-5-ylmethyl}propanamide or its salts;
- N1-{(5S)-3-[3-fluoro-4-(2-oxo-1,3-oxazolan-3-yl)phenyl]-2-oxo-1,3-oxazolan-5-ylmethyl}butanamide or its salts;
- N1-{(5S)-3-[3-fluoro-4-(2-oxo-1,3-oxazolan-3-yl)phenyl]-2-oxo-1,3-oxazolan-5-ylmethyl}pentanamide or its salts;
- N1-{(5S)-3-[3-fluoro-4-(2-oxo-1,3-oxazolan-3-yl)phenyl]-2-oxo-1,3-oxazolan-5-ylmethyl}heptanamide or its salts;
- N1-{(5S)-3-[3-fluoro-4-(2-oxo-1,3-oxazolan-3-yl)phenyl]-2-oxo-1,3-oxazolan-5-ylmethyl}acrylamide or its salts;
- N1-{(5S)-3-[3-fluoro-4-(2-oxo-1,3-oxazolan-3-yl)phenyl]-2-oxo-1,3-oxazolan-5-ylmethyl}-2,2,2-trifluoroacetamide or its salts;
- Ethyl(5S)-3-[3-fluoro-4-(2-oxo-1,3-oxazolan-3-yl)phenyl]-2-oxo-1,3-oxazolan-5-ylmethyl carbamoylmethanoate or its salts;
- N1-{(5S)-3-[3-fluoro-4-(2-thioxo-1,3-oxazolan-3-yl)phenyl]-2-oxo-1,3-oxazolan-5-ylmethyl}acetamide or its salts;
- N1-{(5S)-2-oxo-3-[4-(2-thioxo-1,3-oxazolan-3-yl)phenyl]-1,3-oxazolan-5-ylmethyl}acetamide or its salts;
- N1-{(5S)-3-[3-fluoro-4-(2-oxo-2,3-dihydrobenzo[d][1,3]oxazol-3-yl)phenyl]-2-oxo-1,3-oxazolan-5-ylmethyl}acetamide or its salts;
- N1-{(5S)-3-[3-fluoro-4-(6-methyl-2-oxo-2,3-dihydrobenzo[d][1,3]oxazol-3-yl)phenyl]-2-oxo-1,3-oxazolan-5-ylmethyl}acetamide or its salts;
- N1-{(5S)-3-[3-fluoro-4-(5-methyl-2-oxo-2,3-dihydrobenzo[d][1,3]oxazol-3-yl)phenyl]-2-oxo-1,3-oxazolan-5-ylmethyl}acetamide or its salts;
- N1-{(5S)-2-oxo-3-[4-(2-oxo-1,3-oxazolan-3-yl)-3-trifluoromethylphenyl]-1,3-oxazolan-5-ylmethyl}acetamide or its salts;
- N1-{(5S)-2-oxo-3-[4-(2-oxo-1,3-oxazolan-3-yl)-3-trifluoromethylphenyl]-1,3-oxazolan-5-ylmethyl}propanamide or its salts;
- N1-{(5S)-2-oxo-3-[4-(2-oxo-1,3-oxazolan-3-yl)-3-trifluoromethylphenyl]-1,3-oxazolan-5-ylmethyl}heptanamide or its salts;

N1-{(5S)-2-oxo-3-[4-(2-oxo-1,3-oxazolan-3-yl)-3-trifluoromethylphenyl]-1,3-oxazolan-5-ylmethyl}acrylamide or its salts;
N1-{(5S)-3-[2-fluoro-4-(2-oxo-1,3-oxazolan-3-yl)phenyl]-2-oxo-1,3-oxazolan-5-ylmethyl}acetamide or its salts;
N1-{(5S)-3-[3,5-difluoro-4-(2-oxo-1,3-oxazolan-3-yl)phenyl]-2-oxo-1,3-oxazolan-5-ylmethyl}acetamide or its salts;
N1-{(5S)-3-[3,5-difluoro-4-(2-oxo-1,3-oxazolan-3-yl)phenyl]-2-oxo-1,3-oxazolan-5-ylmethyl}propanamide or its salts;
N1-{(5S)-2-oxo-3-[4-(2-oxo-1,3-oxazolan-3-yl)phenyl]-1,3-oxazolan-5-ylmethyl}acetamide or its salts;
N1-{(5S)-2-oxo-3-[4-(2-oxo-2,3-dihydrobenzo[d][1,3]oxazol-3-yl)phenyl]-1,3-oxazolan-5-ylmethyl}acetamide or its salts;
(5S)-3-[3-fluoro-4-(2-oxo-1,3-oxazolan-3-yl)phenyl]-5-(1-thioxoethylaminomethyl)-1,3-oxazolan-2-one or its salts;
(5S)-3-[3-fluoro-4-(2-oxo-1,3-oxazolan-3-yl)phenyl]-5-(3,3,3-trifluoro-1-thioxopropylaminomethyl)-1,3-oxazolan-2-one or its salts;
3-{2-fluoro-4-[(5S)-2-oxo-5-(1-thioxoethylaminomethyl)-1,3-oxazolan-3-yl]phenyl}-2,3-dihydrobenzo[d][1,3]oxazol-2-one or its salts;
(5S)-3-[4-(2-oxo-1,3-oxazolan-3-yl)-3-trifluoromethylphenyl]-5-(1-thioxoethylaminomethyl)-1,3-oxazolan-2-one or its salts;
(5S)-3-[3,5-difluoro-4-(2-oxo-1,3-oxazolan-3-yl)phenyl]-5-(1-thioxoethylaminomethyl)-1,3-oxazolan-2-one or its salts;
(5S)-3-[3,5-difluoro-4-(2-oxo-1,3-oxazolan-3-yl)phenyl]-5-(1-thioxopropylaminomethyl)-1,3-oxazolan-2-one or its salts;
(5S)-3-[4-(2-oxo-1,3-oxazolan-3-yl)phenyl]-5-(1-thioxoethylaminomethyl)-1,3-oxazolan-2-one or its salts;
N1-{(5S)-3-[3-fluoro-4-(2-oxo-1,3-oxazolan-3-yl)phenyl]-2-oxo-1,3-oxazolan-5-ylmethyl}methylcarbamate or its salts;
N1-{(5S)-2-oxo-3-[4-(2-oxo-1,3-oxazolan-3-yl)-3-trifluoromethylphenyl]-1,3-oxazolan-5-ylmethyl}methylcarbamate or its salts;
N1-{(5S)-3-[3,5-difluoro-4-(2-oxo-1,3-oxazolan-3-yl)phenyl]-2-oxo-1,3-oxazolan-5-ylmethyl}methylcarbamate or its salts;
N1-{(5S)-3-[4-(2-oxo-1,3-oxazolan-3-yl)phenyl]-2-oxo-1,3-oxazolan-5-ylmethyl}methylcarbamate or its salts;
(5S)-5-methylthioxy(thioxo)methylaminomethyl-3-[4-(2-oxo-1,3-oxazolan-3-yl)phenyl]-1,3-oxazolan-2-one or its salts;
N1-{(5S)-3-[3,5-difluoro-4-(2-oxo-1,3-oxazolan-3-yl)phenyl]-2-oxo-1,3-oxazolan-5-ylmethyl}methyldithiocarbamate or its salts;
N1-{(5S)-3-[3-fluoro-4-(2-oxo-1,3-oxazolan-3-yl)phenyl]-2-oxo-1,3-oxazolan-5-ylmethyl}methylthiocarbamate or its salts;
N1-{(5S)-3-[3-fluoro-4-(2-oxo-1,3-oxazolan-3-yl)phenyl]-2-oxo-1,3-oxazolan-5-ylmethyl}ethylthiocarbamate or its salts;
N1-{(5S)-3-[3-fluoro-4-(2-oxo-1,3-oxazolan-3-yl)phenyl]-2-oxo-1,3-oxazolan-5-ylmethyl}trifluoroacetoxythiocarbamate or its salts;
(5S)-cyclohexyloxy(thioxo)methylaminomethyl-3-[4-(2-oxo-1,3-oxazolan-3-yl)phenyl]-1,3-oxazolan-2-one or its salts;
N1-{(5S)-3-[3-fluoro-4-(2-thioxo-1,3-oxazolan-3-yl)phenyl]-2-oxo-1,3-oxazolan-5-ylmethyl}methylthiocarbamate or its salts;
N1-{(5S)-2-oxo-3-[4-(2-oxo-1,3-oxazolan-3-yl)-3-trifluoromethylphenyl]-1,3-oxazolan-5-ylmethyl}methylthiocarbamate or its salts;
N1-{(5S)-2-oxo-3-[4-(2-oxo-1,3-oxazolan-3-yl)-3-trifluoromethylphenyl]-1,3-oxazolan-5-ylmethyl}ethylthiocarbamate or its salts;
N1-{(5S)-3-[3,5-difluoro-4-(2-oxo-1,3-oxazolan-3-yl)phenyl]-2-oxo-1,3-oxazolan-5-ylmethyl}methylthiocarbamate or its salts;
N1-{(5S)-3-[4-(2-oxo-1,3-oxazolan-3-yl)phenyl]-2-oxo-1,3-oxazolan-5-ylmethyl}methylthiocarbamate or its salts;
N1-{(5S)-3-[4-(2-oxo-1,3-oxazolan-3-yl)phenyl]-2-oxo-1,3-oxazolan-5-ylmethyl}ethylthiocarbamate or its salts;
N1-{(5S)-3-[4-(2-oxo-1,3-oxazolan-3-yl)phenyl]-2-oxo-1,3-oxazolan-5-ylmethyl}-1-propylthiocarbamate or its salts;
(5S)-5-[2,2,2-trifluoroethyloxy(thioxo)methylaminomethyl]-3-[4-(2-oxo-1,3-oxazolan-3-yl)phenyl]-1,3-oxazolan-2-one or its salts;
(5S)-5-[2-hydroxyethyloxy (thioxo)methylaminomethyl]-3-[4-(2-oxo-1,3-oxazolan-3-yl)phenyl]-1,3-oxazolan-2-one or its salts;
(5S)-5-[2-methoxyethyloxy (thioxo)methylaminomethyl]-3-[4-(2-oxo-1,3-oxazolan-3-yl)phenyl]-1,3-oxazolan-2-one or its salts;
N1-{(5S)-3-[4-(2-oxo-1,3-oxazolan-3-yl)phenyl]-2-oxo-1,3-oxazolan-5-ylmethyl}allylthiocarbamate or its salts;
N1-{(5S)-3-[4-(2-oxo-1,3-oxazolan-3-yl)phenyl]-2-oxo-1,3-oxazolan-5-ylmethyl}-2-propylthiocarbamate or its salts;
N1-{(5S)-2-oxo-3-[4-(2-oxo-2,3-dihydrobenzol[d][1,3]oxazol-3-yl)phenyl]-1,3-oxazolan-5-ylmethyl}methylthiocarbamate or its salts;
N1-{(5S)-2-oxo-3-[4-(2-oxo-2,3-dihydrobenzo[d][1,3]oxazol-3-yl)phenyl]-1,3-oxazolan-5-ylmethyl}ethylthiocarbamate or its salts;
N1-((5S)-3-{4-[2-oxo-1,3-oxazolan-3yl]phenyl}-2-oxo-1,3-oxazolan-5-ylmethyl)-(N,N-dimethylamino)ethylthiocarbamate or its salts;
(5S)-5-[(2S)-2-hydroxymethylazolan-1-yl(thioxo)methylaminomethyl]-3-[4-(2-oxo-1,3-oxazolan-3-yl)phenyl]-1,3-oxazolan-2-one or its salts;
(5S)-5-diethylamino (thioxo)methylaminomethyl-3-[4-(2-oxo-1,3-oxazolan-3-yl)phenyl]-1,3-oxazolan-2-one or its salts;
(5S)-5-allylamino (thioxo)methylaminomethyl-3-[4-(2-oxo-1,3-oxazolan-3-yl)phenyl]-1,3-oxazolan-2-one or its salts;
(5S)-5-benzylamino(thioxo)methylaminomethyl-3-[4-(2-oxo-1,3-oxazolan-3-yl)phenyl]-1,3-oxazolan-2-one or its salts;
(5S)-5-[4-methoxybenzylamino(thioxo)methylaminomethyl]-3-[4-(2-oxo-1,3-oxazolan-3-yl)phenyl]-1,3-oxazolan-2-one or its salts;
(5S)-3-[4-(2-oxo-1,3-oxazolan-3-yl)phenyl]-5-[2-pyridylmethylamino (thioxo)methylaminomethyl]-1,3-oxazolan-2-one or its salts;
(5S)-5-methylamino(thioxo)methylaminomethyl-3-[4-(2-oxo-1,3-oxazolan-3-yl)phenyl]-1,3-oxazolan-2-one or its salts;

(5S)-5-[2-hydroxyethylamino (thioxo)methylaminomethyl]-3-[4-(2-oxo-1,3-oxazolan-3-yl)phenyl]-1,3-oxazolan-2-one or its salts;

(5S)-3-[4-(2-oxo-1,3-oxazolan-3-yl)phenyl]-5-[1,4-thiazinan-4-yl(thioxo)methylaminomethyl]-1,3-oxazolan-2-one or its salts;

(5S)-3-[4-(2-oxo-1,3-oxazolan-3-yl)phenyl]-5-[2-pyridylamino(thioxo)methylaminomethyl]-1,3-oxazolan-2-one or its salts;

(5S)-5-amino(thioxo)methylaminomethyl-3-[3-fluoro-4-(2-oxo-1,3-oxazolan-3-yl)phenyl]-1,3-oxazolan-2-one or its salts;

(5S)-3-[3-fluoro-4-(2-oxo-1,3-oxazolan-3-yl)phenyl]-5-methylamino (thioxo)methylaminomethyl-1,3-oxazolan-2-one or its salts;

(5S)-5-amino(thioxo)methylaminomethyl-3-[3,5-difluoro-4-(2-oxo-1,3-oxazolan-3-yl)phenyl]-1,3-oxazolan-2-one or its salts;

(5S)-3-[3,5-difluoro-4-(2-oxo-1,3-oxazolan-3-yl)phenyl]-5-methylamino(thioxo)methylaminomethyl-1,3-oxazolan-2-one or its salts and N1-((5S)-3-{4-[2-oxo-1,3-oxazolan-3y]phenyl}-2-oxo-1,3-oxazolan-5-ylmethyl)-(N,N-dimethylamino)ethylthiocarbamate hydrochloride.

6. A compound according to claim 1, wherein the pharmaceutically acceptable salt is selected from Li, Na, K, Ca, Mg, Fe, Cu, Zn, or Mn or salts of organic bases, chiral bases, natural amino acids, unnatural amino acids, substituted amino acids, guanidine, substituted guanidine salts; ammonium, substituted ammonium salts, aluminum salts and acid addition salts.

7. A pharmaceutical composition comprising a compound of formula (I)

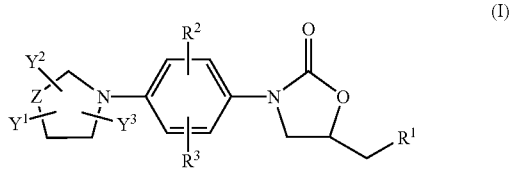

as claimed in claim 1 and a pharmaceutically acceptable carrier, diluent, excipient or solvate.

8. A pharmaceutical composition as claimed in claim 7, in the form of a tablet, capsule, powder, syrup, solution or suspension.

9. A method for treating a bacterial infection comprising administering an effective amount of a compound of formula (I) as claimed in claim 1 to a patient in need thereof.

10. A method for treating a bacterial infection comprising administering an effective amount of a pharmaceutical composition as claimed in claim 7 to a patient in need thereof.

11. A pharmaceutical composition comprising a compound as claimed in claim 5 and a pharmaceutically acceptable carrier, diluent, excipient or solvate.

12. A pharmaceutical composition as claimed in claim 11, in the form of a tablet, capsule, powder, syrup, solution or suspension.

13. A method for treating a bacterial infection comprising administering an effective amount of a compound as claimed in claim 5 to a patient in need thereof.

14. A method for treating a bacterial infection comprising administering an effective amount of a pharmaceutical composition as claimed in claim 11 to a patient in need thereof.

15. The compound according to claim 1, wherein the substituents on $R^a$ are selected from hydroxy, halogen, nitro, amino, alkoxy, carboxy or cyano.

16. A compound according to claim 6, wherein the salts of organic bases are selected from N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, anilnopyridine, purine, or spermidine.

17. A compound according to claim 6, wherein the salts of chiral bases are selected from alkylphenylamine, glycinol, phenyl glycinol.

18. A compound according to claim 6, wherein the salts of natural amino acids are selected from glycine, alanine, valine, leucine, isoleucine, norleucine, tyrosine, cystine, cysteine, methionine, proline, hydroxy proline, histidine, ornithine, lysine, arginine, serine, threonine, or phenylalanine.

19. A compound according to claim 6, wherein the salts of unnatural amino acid, substituted amino acids are selected from D-isomers, guanidine, substituted guanidine wherein the substituents are selected from nitro, amino, alkyl selected from methyl, ethyl, and propyl; alkenyl selected from ethenyl, propenyl, or butenyl; alkynyl selected from ethynyl, or propynyl.

20. A compound according to claim 6, wherein the addition salts are selected from sulphates, nitrates, phosphates, perchlorates, borates, halides, acetates, tartrates, maleates, citrates, succinates, palmoates, methanesulphonates, benzoates, salicylates, hydroxynaphthoates, benzenesulfonates, ascorbates, glycerophosphates, or ketoglutarates.

21. A compound according to claim 5, wherein the pharmaceutically acceptable salt is selected from Li, Na, K, Ca, Mg, Fe, Cu, Zn, or Mn or salts of organic bases, chiral bases, natural amino acids, unnatural amino acids, substituted amino acids, guanidine, substituted guanidine salts; ammonium, substituted ammonium salts, aluminum salts and acid addition salts.

22. A method for treating a bacterial infection comprising administering an effective amount of a pharmaceutical composition as claimed in claim 8 to a patient in need thereof.

23. A method for treating a bacterial infection comprising administering a pharmaceutical composition as claimed in claim 12 to a patient in need thereof.

* * * * *